US011318190B2

(12) United States Patent
Alpini et al.

(10) Patent No.: US 11,318,190 B2
(45) Date of Patent: May 3, 2022

(54) METHODS AND COMPOSITIONS FOR TREATING LIVER DISEASE

(71) Applicant: UNITED STATES GOVERNMENT AS REPRESENTED BY THE DEPARTMENT OF VETERANS AFFAIRS, Washington, DC (US)

(72) Inventors: Gianfranco Alpini, Washington, DC (US); Shannon Glaser, Washington, DC (US); Fanyin Meng, Washington, DC (US)

(73) Assignee: UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 16/611,147

(22) PCT Filed: Apr. 5, 2018

(86) PCT No.: PCT/US2018/031261
§ 371 (c)(1),
(2) Date: Nov. 5, 2019

(87) PCT Pub. No.: WO2018/204893
PCT Pub. Date: Nov. 8, 2018

(65) Prior Publication Data
US 2020/0078445 A1    Mar. 12, 2020

Related U.S. Application Data

(60) Provisional application No. 62/502,374, filed on May 5, 2017.

(51) Int. Cl.
*A61K 38/00* (2006.01)
*A61K 38/22* (2006.01)
*A61P 1/16* (2006.01)

(52) U.S. Cl.
CPC ............ *A61K 38/2235* (2013.01); *A61P 1/16* (2018.01)

(58) Field of Classification Search
CPC ...... A61K 38/2235; A61P 1/16; C07K 14/645
See application file for complete search history.

(56) References Cited

U.S. PATENT DOCUMENTS

| | | |
|---|---|---|
| 4,083,368 A | 4/1978 | Freezer |
| 4,351,337 A | 9/1982 | Sidman |
| 4,849,224 A | 7/1989 | Chang et al. |
| 4,906,169 A | 3/1990 | Chien et al. |
| 4,911,916 A | 3/1990 | Cleary |
| 4,925,673 A | 5/1990 | Steiner et al. |
| 4,925,677 A | 5/1990 | Feijen |
| 4,983,395 A | 1/1991 | Chang et al. |
| 4,994,439 A | 2/1991 | Longenecker et al. |
| 5,013,556 A | 5/1991 | Woodie et al. |
| 5,023,084 A | 6/1991 | Chien et al. |
| 5,284,656 A | 2/1994 | Platz et al. |
| 5,346,701 A | 9/1994 | Heiber et al. |
| 5,460,820 A | 10/1995 | Ebert et al. |
| 5,516,523 A | 5/1996 | Heiber et al. |
| 5,605,702 A | 2/1997 | Teillaud et al. |
| 5,662,925 A | 9/1997 | Ebert et al. |
| 5,783,208 A | 7/1998 | Venkateshwaran et al. |
| 5,792,451 A | 8/1998 | Sarubbi et al. |
| 6,245,740 B1 | 6/2001 | Goldenberg et al. |
| 6,273,086 B1 | 8/2001 | Ohki et al. |
| 6,892,728 B2 | 5/2005 | Helgesson et al. |
| 6,900,317 B2 | 5/2005 | Trunk et al. |
| 6,932,962 B1 | 8/2005 | Backstrom et al. |
| 2001/0049353 A1 | 12/2001 | Beck et al. |
| 2005/0201998 A1 | 9/2005 | Welch et al. |
| 2009/0286270 A1 | 11/2009 | Fallon |
| 2010/0197586 A1* | 8/2010 | Bevec ................... A61P 3/02 514/1.2 |

(Continued)

FOREIGN PATENT DOCUMENTS

| | | |
|---|---|---|
| EP | 3618846 | 3/2020 |
| JP | 2015149907 A * | 8/2015 |

(Continued)

OTHER PUBLICATIONS

Wu et al. The Secretin/Secretin Receptor Axis Modulates Liver Fibrosis Through Changes in Transforming Growth Factor-b1 Biliary Secretion in Mice. 2016. Hepatology, vol. 64, No. 3, 2016 (Year: 2016).*

Glaser et al. The secretin receptor antagonist (SCT 5-27) reduces biliary hyperplasia and liver fibrosis in an animal model of primary sclerosing cholangitis. (Faseb Journal Apr. 2016) (Year: 2016).*

Database Biosis [Online] Biosciences Information Service, Philadelphia, PA, US; Apr. 2015; Glaser, et al. "Inhibition of the Secretin/Secretin Receptor Axis Attenuates Biliary Fibrosis During Cholestasis," XP002801324, Database accession No. PREV201500715968, & Gastroenterology, 148(4): Suppl. 1, Apr. 2015, p. S980, 46th Annual Digestive Disease Week (DDW); Washington, DC, USA; May 16-19, 2015.

(Continued)

*Primary Examiner* — Aradhana Sasan
*Assistant Examiner* — Mercy H Sabila
(74) *Attorney, Agent, or Firm* — Ballard Spahr LLP

(57) ABSTRACT

Disclosed is a method of modulating the Sct/SR axis in a mammalian subject in need thereof, including in a subject suffering from a liver disease, such as but not limited to, Early Stage PBC, Primary Sclerosing Cholangitis, Primary Biliary Cholangitis, Biliary Altresia, NASH, NAFLD, or Alcohol induced liver injury. A method of treating Late Stage PBC in a mammalian subject in need thereof is also disclosed; further disclosed is a method of ameliorating PBC-induced biliary damage in a mammalian subject in need thereof. Pharmaceutical compositions for modulating the Sct/SR axis, comprising a SR antagonist or a SR agonist, and a pharmaceutically acceptable carrier or excipient are also disclosed.

15 Claims, 10 Drawing Sheets
Specification includes a Sequence Listing.

(56) References Cited

U.S. PATENT DOCUMENTS

| | | | |
|---|---|---|---|
| 2011/0039759 A1* | 2/2011 | Davis | A61P 43/00 |
| | | | 514/1.8 |
| 2013/0096050 A1* | 4/2013 | Shandler | C07K 14/57563 |
| | | | 514/1.7 |

FOREIGN PATENT DOCUMENTS

| | | |
|---|---|---|
| WO | WO 2000/038651 A1 | 7/2000 |
| WO | WO 2000/038652 | 7/2000 |
| WO | WO 2002/011801 | 2/2002 |
| WO | WO 2004/017918 | 3/2004 |
| WO | WO 2017/202851 A1 | 11/2017 |
| WO | WO 2018/204893 | 11/2018 |

OTHER PUBLICATIONS

Database Embase [Online] Elsevier Science Publishers, Amsterdam, NL; Oct. 1, 2017, Francis et al. "Secretin receptor antagonist treatment reduces biliary damage and liver fibrosis in a mouse model of early stage primary biliary cholangitis (PBC), but not advanced PBC," XP002801325, Database accession No. EMB-618936666, & Hepatology Jan. 2017 John Wiley and Sons Inc. NLD 66: Supplement 1, Oct. 1, 2017, p. 161A, Conf Oct. 20, 2017 to Oct. 24, 2017 Washington, DC—68th Annu, ISSN: 1527-3350.
Glaser, et al. (2016) "The secretin receptor antagonist (SCT 5-27) reduces biliary hyperplasia and liver fibrosis in an animal model of primary sclerosing cholangitis," The FASEB Journal XP055755967, Retrieved from the Internet: URL: https://faseb.onlinelibrary.wiley.com/doi/10.1096/fasebj.30.1.supplement.56.7 [retrieved on Dec. 2, 2020].
Supplementary European Search Report dated Dec. 18, 2020 by the European Search Authority for EP Application No. 18795253.6, filed on May 4, 2018 and published as EP 3618846 dated Mar. 11, 2020 (Applicant—The United States Government as represented by the Department of Veterans Affairs) (11 pages).
Abuchowski and Davis (1981), Soluble Polymer—Enzyme Adducts, Enzymes as Drugs (Hocenberg and Roberts, eds.), Wiley-Interscience, New York, NY, pp. 367-383.
Alpini, G et al., Large but not small intrahepatic bile ducts are involved in secretin-regulated ductal bile secretion, Am J Physiol 272:G1064-1074 (1997).
Alpini, G et al., Morphological, molecular, and functional heterogeneity of cholangiocytes from normal rat liver, Gastroenterology 110:1636-1643 (1996).
Alpini, G et al., Upregulation of secretin receptor gene expression in rat cholangiocytes after bile duct ligation, Am J Physiol 1994;266:G922-928 (1994).
Alvaro, D et al., Effect of secretion on intracellular pH regulation in isolated rat bile duct epithelial cells, J Clin Invest 92:1314-1325 (1993).
Alvaro, D et al., Proliferating cholangiocytes: a neuroendocrine compartment in the diseased liver, Gastroenterology 132(1):415-431 (2007).
Barnes, BH et al., Cholangiocytes as immune modulators in rotavirus-induced murine biliary atresia, Liver Int 29:1253-1261 (2009).
Bodansky, M et al., Synthesis and some pharmacological properties of the 23-peptide 15-lysine-secretin-(5-27). Special role of the residue in position 15 in biological activity of the vasoactive intestinal polypeptide, J. Med. Chem. 21(11):1171-73 (1978).
Boissart, C et al., miR-125 potentiates early neural specification of human embryonic stem cells. Development 139(7):1247-1257 (2012).
Boonstra, K et al., Rising incidence and prevalence of primary biliary cirrhosis: a large population-based study, Liver Int 34:e31-38 (2014).
Braquet et al. Effect of endothelin-1 on blood pressure and bronchopulmonary system of the guinea pig (1989), J. Cardiovasc. Pharmacol. 13 (suppl.5): s.143-146.

Campisi, J et al., Cellular senescence: when bad things happen to good cells, Nat Rev Mol Cell Biol 8:729-740 (2007).
Debs et al. Lung-specific delivery of cytokines induces sustained pulmonary and systemic immunomodulation in rats (1988), J. Immunol. 140: 3482-8.
European Association for the Study of the L. EASL Clinical Practice Guidelines: management of cholestatic liver diseases, J Hepatol 51:237-267 (2009).
Gaudio E et al., Vascular endothelial growth factor stimulates rat cholangiocyte proliferation via an autocrine mechanism, Gastroenterology 130(4):1270-1282 (2006).
Gaudio, E et al., Administration of r-VEGF-A prevents hepatic artery ligation-induced bile duct damage in bile duct ligated rats, Am J Physiol Gastrointest Liver Physiol 291(2):G307-31 (2006).
Glaser, S et al., Knockout of secretin receptor reduces large cholangiocyte hyperplasia in mice with extrahepatic cholestasis induced by bile duct ligation, Hepatology 52:204-214 (2010).
Glaser, S et al., Secretin stimulates biliary cell proliferation by regulating expression of microRNA 125b and microRNA let7a in mice, Gastroenterology 146(7):1795-1808 e1712(2014).
Gong, Y et al., Ursodeoxycholic acid for primary biliary cirrhosis. Cochrane Database Syst Rev CD000551 (2008).
Gourlet, et al. Interaction of amino acid residues at positions 8-15 of secretin with the N-terminal domain of the secretin receptor, Eur J Biochem 239: 349-355 (1996).
Guerrier, M et al., Prolonged administration of secretin to normal rats increases biliary proliferation and secretin-induced ductal secretory activity, Hepatobiliary Surg Nutr 3(3):118-125 (2014).
Han, Y et al., Prolonged exposure of cholestatic rats to complete dark inhibits biliary hyperplasia and liver fibrosis, Am J Physiol Gastrointest Liver Physiol 2014;307:G894-904 (2014).
Heathcote, EJ, Management of primary biliary cirrhosis. The American Association for the Study of Liver Diseases practice guidelines, Hepatology 31:1005-1013 (2000).
Hirschfield, GM et al., Efficacy of obeticholic acid in patients with primary biliary cirrhosis and inadequate response to ursodeoxycholic acid, Gastroenterology 2015;148:751-761 e758.
Hohenester, S et al., A biliary HCO3—umbrella constitutes a protective mechanism against bile acid-induced injury in human cholangiocytes, Hepatology 55:173-183 (2012).
Hohenester, S et al., Biliary bicarbonate secretion constitutes a protective mechanism against bile acid-induced injury in man, Dig Dis 29:62-65 (2011).
Hubbard et al. Anti-neutrophil-elastase defenses of the lower respiratory tract in alpha 1-antitrypsin deficiency directly augmented with an aerosol of alpha 1-antitrypsin (1989), Annals Int. Med. 3: 206-12.
Jones, H et al., Inhibition of mast cell-secreted histamine decreases biliary proliferation and fibrosis in primary sclerosing cholangitis Mdr2(-/-) mice, Hepatology 2016;64:1202-1216 (2016).
Kato, A et al., Secretin stimulates exocytosis in isolated bile duct epithelial cells by a cyclic AMP-mediated mechanism, J Biol Chem 267:15523-15529 (1992).
Kennedy, LL et al., Knockout of microRNA-21 reduces biliary hyperplasia and liver fibrosis in cholestatic bile duct ligated mice, Lab Invest 2016;96:1256-1267 (2016).
Kim, KH et al., CCN1 induces hepatic ductular reaction through integrin alphavbeta(5)-mediated activation of NF-kappaB, J Clin Invest 2015;125:1886-900 (2015).
LeSage, GD et al., Acute carbon tetrachloride feeding induces damage of large but not small cholangiocytes from BDL rat liver, Am J Physiol 276:G1289-301 (1999).
Lleo, A et al., Evolving Trends in Female to Male Incidence and Male Mortality of Primary Biliary Cholangitis, Sci Rep 2016;6:25906. 3-6 (2016).
Ludwig, J et al., Staging of chronic nonsuppurative destructive cholangitis (syndrome of primary biliary cirrhosis). Virchows Arch A Pathol Anat Histol 379:103-11223 (1978).
Mancinelli, R et al., After damage of large bile ducts by gamma-aminobutyric acid, small ducts replenish the biliary tree by amplification of calcium-dependent signaling and de novo acquisition of large cholangiocyte phenotypes, Am J Pathol 2010;176:1790-800 (2010).

(56) References Cited

OTHER PUBLICATIONS

Mancinelli, R et al., *GABA induces the differentiation of small into large cholangiocytes by activation of Ca(2+) /CaMK I-dependent adenylyl cyclase 8*. Hepatology 58:251-263 (2013).
Mancinelli, R et al., *Ischemia reperfusion of the hepatic artery induces the functional damage of large bile ducts by changes in the expression of angiogenic factors*. Am J Physiol Gastrointest Liver Physiol 2015;309:G865-873 (2015).
McDaniel, K et al., *Forkhead box A2 regulates biliary heterogeneity and senescence during cholestatic liver injury in micedouble dagger*, Hepatology 2017;65:544-559 (2017).
Mells, JE et al., *Saturated fat and cholesterol are critical to inducing murine metabolic syndrome with robust nonalcoholic steatohepatitis*, J Nutr Biochem 2015;26:285-9.
Moncsek, A et al., *Targeting senescent cholangiocytes and activated fibroblasts with Bcl-xL inhibitors ameliorates fibrosis in Mdr2(-/-) mice*, Hepatology (Baltimore, Md) 67(1): 247-259 (2018).
Myers, RP et al., *Epidemiology and natural history of primary biliary cirrhosis in a Canadian health region: a population-based study*, Hepatology 50:1884-1892 (2009).
Natarajan, SK et al., *Saturated free fatty acids induce cholangiocyte lipoapoptosis*, Hepatology 60:1942-56 (2014).
Nevens, F et al., *A Placebo-Controlled Trial of Obeticholic Acid in Primary Biliary Cholangitis*, N Engl J Med 2016;375:631-64313 (2016).
O'Hara, SP et al., *Cholangiocyte N-Ras protein mediates lipopolysaccharide-induced interleukin 6 secretion and proliferation*, J Biol Chem 286:30352-60 (2011).
O'Hara, SP et al., *TLR4 promotes Cryptosporidium parvum clearance in a mouse model of biliary cryptosporidiosis*, J Parasitol 2011;97:813-21 (2011).
Onori, P et al., *Caffeic acid phenethyl ester decreases cholangiocarcinoma growth by inhibition of NF-kappaB and induction of apoptosis*, Int J Cancer 2009;125:565-76 (2009).
Podda, M et al., *The limitations and hidden gems of the epidemiology of primary biliary cinhosis*, J Autoimmun 46:81-87 (2013).
Poupon, RE et al., *A multicenter, controlled trial of ursodiol for the treatment of primary biliary cirrhosis. UDCA-PBC Study Group*, N Engl J Med 324:1548-1554 (1991).
Rudic, JS et al., *Ursodeoxycholic acid for primary biliary cirrhosis*, Cochrane Database Syst Rev 12:CD000551 (2012).
Sasaki, M et al., *Activation of ATM signaling pathway is involved in oxidative stress-induced expression of mito-inhibitory p21WAF1/Cip1 in chronic non-suppurative destructive cholangitis in primary biliary cirrhosis: an immunohistochemical study*, J Autoimmun 31:73-78 (2008).
Sasaki, M et al., *Chemokine-chemokine receptor CCL2-CCR2 and CX3CL1-CX3CR1 axis may play a role in the aggravated inflammation in primary biliary cirrhosis*, Dig Dis Sci 59:358-364 (2014).
Scheuer P, *Primary biliary cirrhosis*, Proc R Soc Med 60:1257-1260 (1967).
Sekar, R and Chow, BK, *Secretin receptor-knockout mice are resistant to high-fat diet-induced obesity and exhibit impaired intestinal lipid absorption*, FASEB J 28:3494-505 (2014).

Shimizu, R et al., *Cholangiocyte senescence caused by lysophosphatidylcholine as a potential implication in carcinogenesis*, J Hepatobiliary Pancreat Sci 22(9):675-682 (2015).
Sood, S et al., *Epidemiology of primary biliary cirrhosis in Victoria, Australia: high prevalence in migrant populations*, Gastroenterology 2004;127:470-475 (2004).
Tabibian, JH et al., *Characterization of cultured cholangiocytes isolated from livers of patients with primary sclerosing cholangitis*, Lab Invest 94:1126-1133 (2014).
Tabibian, JH et al., *Cholangiocyte senescence by way of N-ras activation is a characteristic of primary sclerosing cholangitis*, Hepatology 59:2263-227530-32 (2014).
Taffetani S et al., *Prolactin stimulates the proliferation of normal female cholangiocytes by differential regulation of Ca2+-dependent PKC isoforms*, BMC Physiol 7:6 (2007).
Veterans Administration Merit Grant No. I01BX000574.
Vuoristo, M et al., *A placebo-controlled trial of primary biliary cirrhosis treatment with colchicine and ursodeoxycholic acid*, Gastroenterology 108:1470-1478 (1995).
Wu, N et al., *The secretin/secretin receptor axis modulates liver fibrosis through changes in transforming growth factor-beta1 biliary secretion in mice*, Hepatology 64:865-79 (2016).
Yan, C et al., *Characterization and identification of differentially expressed microRNAs during the process of the peribiliary fibrosis induced by Clonorchis sinensis*, Infect Genet Evol 43:321-328 (2016).
Yin, H et al., Progress on the relationship between miR-125 family and tumorigenesis, Exp Cell Res 2015;339(2):252-260 (2015).
Yoshiji, H et al., *Vascular endothelial growth factor and receptor interaction is a prerequisite for murine hepatic fibrogenesis*, Gut 52(9):1347-1354 (2003).
Zhao, Y et al., *Hepatic stellate cells produce vascular endothelial growth factor via phospho-p44/42 mitogen-activated protein kinase/cyclooxygenase-2 pathway*, Mol Cell Biochem 2012;359(1-2):217-22 (2012).Z.
International Search Report and Written Opinion dated Aug. 11, 2018 by the International Searching Authority for International Application No. PCT/US2018/031261, filed on May 5, 2018, and published as WO 2018/204893 dated Nov. 8, 2018 (Applicant—United States Government as Represented by the Department of Veterans Affairs) (10 Pages).
International Preliminary Report on Patentability dated May 11, 2019 by the International Searching Authority for International Application No. PCT/US2018/031261, filed on May 5, 2018, and published as WO 2018/204893 dated Nov. 8, 2018 (Applicant—United States Government as Represented by the Department of Veterans Affairs) (7 Pages).
Glaser et al., "Inhibition of the Secretin/Secretin Receptor Axis Attenuates Biliary Fibrosis During Cholestasis," Gastroenterology 148(4 Supplement 1):S-980, Abstract 459 (2015).†
Zollner et al., "Secretin and Cholestasis, Two Sidesof a Coin," Hepatology 64(3):714-6 (2016).†

\* cited by examiner
† cited by third party

```
                         SEQUENCE LISTING

<160> NUMBER OF SEQ ID NOS: 15

<210> SEQ ID NO 1
<211> LENGTH: 121
<212> TYPE: PRT
<213> ORGANISM: Homo sapiens

<400> SEQUENCE: 1

Met Ala Pro Arg Pro Leu Leu Leu Leu Leu Leu Leu Gly Gly Ser
1               5                   10                  15

Ala Ala Arg Pro Ala Pro Pro Arg Ala Arg Arg His Ser Asp Gly Thr
                20                  25                  30

Phe Thr Ser Glu Leu Ser Arg Leu Arg Glu Gly Ala Arg Leu Gln Arg
            35                  40                  45

Leu Leu Gln Gly Leu Val Gly Lys Arg Ser Glu Gln Asp Ala Glu Asn
    50                  55                  60

Ser Met Ala Trp Thr Arg Leu Ser Ala Gly Leu Leu Cys Pro Ser Gly
65                  70                  75                  80

Ser Asn Met Pro Ile Leu Gln Ala Trp Met Pro Leu Asp Gly Thr Trp
                85                  90                  95

Ser Pro Trp Leu Pro Pro Gly Pro Met Val Ser Glu Pro Ala Gly Ala
            100                 105                 110

Ala Ala Glu Gly Thr Leu Arg Pro Arg
            115                 120

<210> SEQ ID NO 2
<211> LENGTH: 27
<212> TYPE: PRT
<213> ORGANISM: Homo sapiens

<400> SEQUENCE: 2

His Ser Asp Gly Thr Phe Thr Ser Glu Leu Ser Arg Leu Arg Glu Gly
1               5                   10                  15

Ala Arg Leu Gln Arg Leu Leu Gln Gly Leu Val
            20                  25

<210> SEQ ID NO 3
<211> LENGTH: 23
<212> TYPE: PRT
<213> ORGANISM: Homo sapiens

<400> SEQUENCE: 3

Thr Phe Thr Ser Glu Leu Ser Arg Leu Arg Lys Gly Ala Arg Leu Gln
1               5                   10                  15

Arg Leu Leu Gln Gly Leu Val
            20

<210> SEQ ID NO 4
<211> LENGTH: 18
<212> TYPE: DNA
<213> ORGANISM: Artificial Sequence
<220> FEATURE:
<223> OTHER INFORMATION: primer
```

```
<400> SEQUENCE: 4
gagtgccacc ttgccctg                                              18

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gatttgagtt tcggtgctgg                                            20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
ggtttgggga gccagtatct                                            20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
caagcctgca ttcatcaaga                                            20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
gccagaggcc acttgtgtag                                            20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
tcatactcag gcccagttcc                                            20

<210> SEQ ID NO 10
<211> LENGTH: 17
<212> TYPE: DNA
<213> ORGANISM: Artificial Sequence
<220> FEATURE:
<223> OTHER INFORMATION: primer

<400> SEQUENCE: 10
cccatggctc aggcaag                                               17

<210> SEQ ID NO 11
```

```
<211> LENGTH: 22
<212> TYPE: DNA
<213> ORGANISM: Artificial Sequence
<220> FEATURE:
<223> OTHER INFORMATION: primer

<400> SEQUENCE: 11
gtgcctgagg tttcatactc ag                                             22

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
caacacgcgc tggaagttca                                                20

<210> SEQ ID NO 13
<211> LENGTH: 22
<212> TYPE: DNA
<213> ORGANISM: Artificial Sequence
<220> FEATURE:
<223> OTHER INFORMATION: primer

<400> SEQUENCE: 13
gatgctgcct agttcaaagt cg                                             22

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
tgtcaagacc gacctgtccg                                                20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
tattcggcaa gcaggcatcg                                                20
```

METHODS AND COMPOSITIONS FOR TREATING LIVER DISEASE

CROSS REFERENCE TO RELATED APPLICATIONS

This Application is a national stage filing under 35 U.S.C. § 371 of International Application No. PCT/US2018/031261, filed May 5, 2018, which claims the benefit of U.S. Provisional Application No. 62/502,374, filed May 5, 2017, the contents of which are incorporated herein by reference in their entireties.

GOVERNMENT SUPPORT

This invention was made with Government support under Veterans Administration Merit Grant I01BX000574 and NIH grants R01DK054811, R01DK107310, and R21AA025157. The Government has certain rights in the invention.

REFERENCE TO SEQUENCE LISTING

A Sequence Listing submitted as in ASCII text file via EFS-Web is hereby incorporated by reference in accordance with MPEP 2422.03 and 37 CFR 1.821(c). The name of the ASCII text file for the Sequence Listing is "DVA_040WO1_ST25", the date of creation of the ASCII text file is May 4, 2018, and the size of the ASCII text file is 4.06 KB.

BACKGROUND OF THE INVENTION

1. Field of the Invention

The present invention is related to the treatment of liver diseases in mammalian subjects, including humans.

2. Related Art

Cholangiocytes are epithelial cells that line the intrahepatic and extrahepatic bile ducts and are the target of cholangiopathies, including Primary Sclerosing Cholangitis (PSC) and Primary Biliary Cholangitis (PBC). PBC is a chronic autoimmune disease that is characterized by damage of intrahepatic small bile ducts leading to ductopenia, cholestasis, fibrosis and eventually cirrhosis. PBC is a rare disease that primarily affects middle-aged women. (See, e.g., Podda, M et al, *The limitations and hidden gems of the epidemiology of primary biliary cirrhosis*, J Autoimmun 46:81-87 (2013)). Early stage PBC is generally characterized by ductular reaction and mild fibrosis, while late stage PBC is characterized ductopenia of intrahepatic small bile ducts and bridging fibrosis. (Scheuer P, *Primary biliary cirrhosis*, Proc R Soc Med 60:1257-1260 (1967)).

Recent reports have indicated that incidence and prevalence of PBC are rising. (Sood, S et al., *Epidemiology of primary biliary cirrhosis in Victoria, Australia: high prevalence in migrant populations*, Gastroenterology 2004; 127:470-475 (2004); Boonstra, K et al., *Rising incidence and prevalence of primary biliary cirrhosis: a large population-based study*, Liver Int 34:e31-38 (2014); Myers, R P et al., *Epidemiology and natural history of primary biliary cirrhosis in a Canadian health region: a population-based study*, Hepatology 50:1884-1892 (2009); Lleo, A et al., *Evolving Trends in Female to Male Incidence and Male Mortality of Primary Biliary Cholangitis*, Sci Rep 2016; 6:25906.3-6 (2016)).

For the past 20 years, ursodeoxycholic acid (UDCA) has been the preferred treatment for PBC (European Association for the Study of the L. EASL *Clinical Practice Guidelines: management of cholestatic liver diseases*, J Hepatol 51:237-267 (2009); Poupon, R E et al., *A multicenter, controlled trial of ursodiol for the treatment of primary biliary cirrhosis. UDCA-PBC Study Group*, N Engl J Med 324:1548-1554 (1991); Vuoristo, M et al., *A placebo-controlled trial of primary biliary cirrhosis treatment with colchicine and ursodeoxycholic acid*, Gastroenterology 108:1470-1478 (1995)); however, up to 40% of PBC patients are unresponsive to this treatment, and UDCA has been shown to have little benefit on mortality and liver transplantation rates. (Gong, Y et al., *Ursodeoxycholic acid for primary biliary cirrhosis*. Cochrane Database Syst Rev CD000551 (2008); Rudic, J S et al., *Ursodeoxycholic acid for primary biliary cirrhosis,* Cochrane Database Syst Rev 12:CD000551 (2012)).

Recently, obeticholic acid (OCA) was approved for the treatment of PBC after showing favorable biochemical responses (Hirschfield, G M et al., *Efficacy of obeticholic acid in patients with primary biliary cirrhosis and inadequate response to ursodeoxycholic acid*, Gastroenterology 2015; 148:751-761 e758; Nevens, F et al., *A Placebo-Controlled Trial of Obeticholic Acid in Primary Biliary Cholangitis*, N Engl J Med 2016; 375:631-64313 (2016)); however, these initial biochemical markers may not accurately predict long-term outcomes, and no information exists regarding the impact of OCA on mortality or liver transplantation rates in PBC patients.

Secretin (Sct) is a peptide hormone that exerts its effects through the secretin receptor (SR), which is expressed only by large cholangiocytes in the liver (Nevens, F et al., *A Placebo-Controlled Trial of Obeticholic Acid in Primary Biliary Cholangitis*, N Engl J Med 375:631-64313 (2016); Alpini, G et al., *Large but not small intrahepatic bile ducts are involved in secretin-regulated ductal bile secretion*, Am J Physiol 272:G1064-1074 (1997)).

Secretin is traditionally known for stimulating secretion of bicarbonate via cyclic adenosine monophosphate (cAMP)-mediated opening of cystic fibrosis transmembrane conductance regulator (CFTR) and activation of $Cl^-/HCO_3^-$ exchanger (AE2). (See, Alpini, G et al., *Large but not small intrahepatic bile ducts are involved in secretin-regulated ductal bile secretion*, Am J Physiol 1997; 272:G1064-1074 (1997); Alpini, G et al., *Morphological, molecular, and functional heterogeneity of cholangiocytes from normal rat liver*, Gastroenterology 110:1636-1643 (1996); Alvaro, D et al., *Effect of secretion on intracellular pH regulation in isolated rat bile duct epithelial cells*, J Clin Invest 92:1314-1325 (1993); Kato, A et al., *Secretin stimulates exocytosis in isolated bile duct epithelial cells by a cyclic AMP-mediated mechanism*, J Biol Chem 267:15523-15529 (1992)).

Reports have further identified that Sct stimulates cholangiocyte proliferation via SR activation, and following bile duct ligation (BDL, model of cholestasis) cholangiocytes begin to proliferate and increase their expression of SR. As well, knockout of Sct or SR decreases BDL-induced cholangiocyte proliferation (Glaser, S et al., *Secretin stimulates biliary cell proliferation by regulating expression of microRNA 125b and microRNA let7a in mice*, Gastroenterology 2014; 146:1795-1808 e1712 (2014); Glaser, S et al., *Knockout of secretin receptor reduces large cholangiocyte hyperplasia in mice with extrahepatic cholestasis induced by*

*bile duct ligation*, Hepatology 52:204-214 (2010); Alpini, G et al., *Upregulation of secretin receptor gene expression in rat cholangiocytes after bile duct ligation*, Am J Physiol 1994; 266:G922-928 (1994)).

Aside from cholangiocyte proliferation, increased Sct/SR signaling has been shown to promote hepatic fibrosis. Specifically, following BDL and in the multidrug resistance gene 2 knockout (Mdr2$^{-/-}$) mouse model of PSC increased Sct/SR signaling is associated with increased hepatic fibrosis and hepatic stellate cell (HSC) activation via upregulated transforming growth factor-β1 (TGF-β1) signaling; however, these parameters are reduced following treatment with an SR antagonist (Sec 5-27). It is apparent that Sct/SR signaling plays a prominent role in biliary homeostasis, and dysregulation of this signaling pathway influences biliary damage and hepatic fibrosis during injury. (See, Wu, N et al., *The secretin/secretin receptor axis modulates liver fibrosis through changes in transforming growth factor-beta1 biliary secretion in mice*, Hepatology 64:865-87921 (2016)).

Nonalcoholic fatty liver disease (NAFLD) is another alarming public health concern and is now considered the most common liver disease in the Western world. Patients with NAFLD may develop nonalcoholic steatohepatitis (NASH) of which many develop hepatic injury that may progress to cirrhosis. In chronic cholestatic liver diseases, cholangiocytes, through the products of their cellular activation such as secretin (SCT), are the key link between bile duct injury and the subepithelial fibrosis that characterizes chronic hepatobiliary injury. Recent evidence and our novel preliminary data indicate that cholangiocytes play a key role in the pathogenesis of NAFLD through activation of biliary damage/proliferation and subsequent liver fibrosis. (See, e.g., Natarajan, S K et al., *Saturated free fatty acids induce cholangiocyte lipoapoptosis*, Hepatology 60:1942-56 (2014)).

A recent study has shown that secretin receptor (SR) knockout mice are resistant to high-fat diet (HFD)-induced obesity and exhibit impaired intestinal lipid absorption. (Sekar, R and Chow, B K, *Secretin receptor-knockout mice are resistant to high-fat diet-induced obesity and exhibit impaired intestinal lipid absorption*, FASEB J 28:3494-505 (2014)). While this study evaluated intestinal lipid absorption, the autocrine/paracrine role of the SCT/SR axis in the liver was not evaluated.

Other studies have demonstrated that activation of the SCT/SR axis plays a key role in the progression of liver fibrosis and biliary damage during cholestatic liver diseases via secretion of transforming growth factor-β1 (TGF-β1) by cholangiocytes and subsequent activation of hepatic stellate cells (HSCs). (Glaser, S et al., *Secretin stimulates biliary cell proliferation by regulating expression of microRNA 125b and microRNA let7a in mice*, Gastroenterology 146:1795-808 e12 (2014); Wu, N et al., *The secretin/secretin receptor axis modulates liver fibrosis through changes in transforming growth factor-beta1 biliary secretion in mice*, Hepatology 64:865-79 (2016)).

Alcoholic liver disease (ALD) is a chronic disease that is widespread and culminates in cirrhosis and ultimately hepatocellular carcinoma. The role of cholangiocytes in ALD is unclear, but a hallmark of biliary damage/repair is ductular response in response to liver injury during ALD.

Effective treatment modalities are still greatly needed for PBC, NAFLD, NASH, and other liver diseases, such as but not limited to, Alcoholic Liver Disease (ALD), which the present invention provides.

SUMMARY OF THE INVENTION

The present inventive method of modulating a Sct/SR axis in a mammalian subject is based on our observations that, inter alia: (i) the SCT/SR axis is upregulated in cholangiocytes in an animal model of NAFLD/NASH and human liver samples with steatosis and steatohepatitis; (ii) increased biliary proliferation, cholangiocyte lipoapoptosis and hepatobiliary fibrosis are observed in animals treated with a high-fat diet (HFD); (iii) in vitro there is increased secretion of secretin and increased expression of the SCT/SR axis in mouse cholangiocytes stimulated with saturated free fatty acids (FFAs); (iv) there is decreased cholangiocyte proliferation and hepatic steatosis and fibrosis in SR knockout mice fed HFD compared to wild type (WT) fed HFD; (v) in isolated cholangiocytes from SR knockout mice fed HFD there is a significant increase in the expression of factors regulating lipid metabolism (PPAR-α, Cpt1a and Acsl1), and reduced lipoapoptosis compared to WT fed HFD; (vi) in isolated cholangiocytes and HSCs (mediated by paracrine release of profibrogenic factors such as TGF-β1, vascular endothelial growth factor (VEGF) and nerve growth factor (NGF) by cholangiocytes since SR is expressed only by cholangiocytes) and total liver from SR knockout mice fed HFD, there is a significant reduction in the expression of profibrotic markers (TGF-β1, collagen 1a1, Col1a1, α-smooth muscle actin, α-SMA and fibronectin 1, Fn1) compared to WT fed HFD; and (vii) there is a significant increase in the expression levels of the neuroendocrine (VEGF-A and NGF) and fibrogenic (TGF-β1) factors in cholangiocytes isolated from WT mice fed HFD, which was associated with decreased expression of miR-125b and Let-7a that target VEGF-A and NGF, respectively.

Provided herein is a method of modulating the Sct/SR axis in a mammalian subject in need thereof (including a human patient), comprising administering an effective amount of a SR antagonist to said subject. Such mammalian subjects, including humans, are typically in need of treatment for a liver disease, which can include Early Stage PBC, Primary Sclerosing Cholangitis, Primary Biliary Cholangitis, Biliary Atresia, NASH, NAFLD, and Alcohol induced liver injury.

Also provided is a method of treating Late Stage PBC in a mammalian subject in need thereof, comprising administering an effective amount of a SR agonist to said subject.

Also provided is a method of ameliorating PBC-induced biliary damage in a mammalian subject in need thereof, comprising modulating a Sct/SR axis of said subject. In one embodiment, this method further comprises ameliorating liver fibrosis. In a particular embodiment, the Sct/SR axis is modulated by administering an effective amount of an SR antagonist to said subject.

Another aspect of the invention is a pharmaceutical composition, comprising a SR antagonist or a SR agonist, and a pharmaceutically acceptable carrier or excipient.

The foregoing summary is not intended to define every aspect of the invention, and additional aspects are described in other sections, such as the Detailed Description of Embodiments. The entire document is intended to be related as a unified disclosure, and it should be understood that all combinations of features described herein are contemplated, even if the combination of features are not found together in the same sentence, or paragraph, or section of this document.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to claim subject matter described in the prior art work of others. Therefore, in the event that statutory prior art within the scope of a claim is brought to the attention of the applicants by a Patent Office or other entity or individual, the applicant(s) reserve the right to exercise amendment rights under applicable patent laws to redefine the subject matter of such a claim to specifically exclude such statutory prior art or obvious variations of statutory prior art from the scope of such a claim. Variations of the invention defined by such amended claims also are intended as aspects of the invention.

BRIEF DESCRIPTION OF THE DRAWINGS

FIG. 3A: There is a significant increase in hepatic fibrosis by Sirius red staining in human liver samples with steatohepatitis. FIG. 3B: The increase in hepatic fibrosis in steatohepatitis samples was confirmed by immunofluorescence for collagen 1 (green color) with containing for biliary epithelial cells with CK-19 (red color). FIG. 3C: There is an increase in CK-19 positive bile ducts in the human steatohepatitis liver samples compared to normal control. FIG. 3D By real-time PCR, The secretin/secretin receptor axis is significantly upregulated in steatohepatitis samples compared to normal human liver. Data are mean±SEM of 3 evaluations. $*p<0.05$ vs normal.

FIG. 4A: An increase in hepatic fibrosis (Sirus red staining) is observed in ethanol fed WT mice. The ethanol-induced increase in hepatic fibrosis was inhibited in ethanol fed $Sct^{-/-}$ knockout mice. FIG. 4B: An increase in the number of CK-19 positive bile ducts in observed in WT mice fed with alcohol. The ethanol-induced biliary proliferation was inhibited in ethanol fed $Sct^{-/-}$ knockout mice. FIG. 4C: Analysis of the percentage of IBDM in the liver sections. There was a significant increase in % IBDM in the ethanol-fed WT mice. There was a significant reduction in % IBDM in ethanol fed $Sct^{-/-}$ mice compared to the ethanol-fed WT mice. Data are mean±SEM of 3 evaluations. $*p<0.05$ vs normal. $\#p<0.05$ vs ethanol-fed WT mice.

In FIG. 7A, there was increased IBDM (red arrows) in Mdr2$^{-/-}$ mice compared to WT mice, which was reduced in SR$^{-/-}$/Mdr2$^{-/-}$ mice compared to Mdr2$^{-/-}$ mice; no significant changes in IBDM were noted in SR$^{-/-}$ compared to WT mice. Original magn., 40×. FIG. 7B shows there was increased mRNA expression of PCNA and Ki67 in cholangiocytes from Mdr2$^{-/-}$ mice, which was decreased in SR$^{-/-}$/Mdr2$^{-/-}$ compared to Mdr2$^{-/-}$ mice. Data are mean±SEM of n=3 from a cumulative preparation of cholangiocytes from 8 mice. *$p<0.05$ versus FVB mice; #$p<0.05$ versus Mdr2$^{-/-}$ mice.

FIGS. 8A-B and FIG. 8D show measurement of collagen deposition in liver sections. There was enhanced collagen deposition in Mdr2$^{-/-}$ mice compared to WT mice, which was significantly decreased in SR$^{-/-}$/Mdr2$^{-/-}$ compared to Mdr2$^{-/-}$ mice. Orig. magn., ×20. FIG. 8C shows immunofluorescence in liver sections, there was enhanced immunoreactivity for Col1a1 (green color, costained with CK-19 in red) in Mdr2$^{-/-}$ (compared to WT mice), which was reduced in SR$^{-/-}$/Mdr2$^{-/-}$ compared to Mdr2$^{-/-}$ mice. There was enhanced co-localization of α-SMA and desmin (α-SMA in green color, costained with desmin in red) in HSCs from Mdr2$^{-/-}$ compared to WT that was decreased in SR$^{-/-}$/Mdr2$^{-/-}$ compared to Mdr2$^{-/-}$ mice (FIG. 8C; scale bar=100 μm). FIG. 8B and FIG. 8D show there was enhanced expression of Col1a1 and FN-1 in isolated cholangiocytes and HSCs from Mdr2$^{-/-}$ mice compared to the corresponding WT mice, increase that was significantly reduced in SR$^{-/-}$/Mdr2$^{-/-}$ mice compared to Mdr2$^{-/-}$ mice. Data are mean±SEM of n=3 from one cumulative preparation of cholangiocytes from 8 mice, and 3 preparations of LCM-isolated HSCs from 3 mice. *$p<0.05$ vs. FVB mice; #$p<0.05$ vs. Mdr2$^{-/-}$ mice.

DETAILED DESCRIPTION OF EMBODIMENTS

Figure 1:
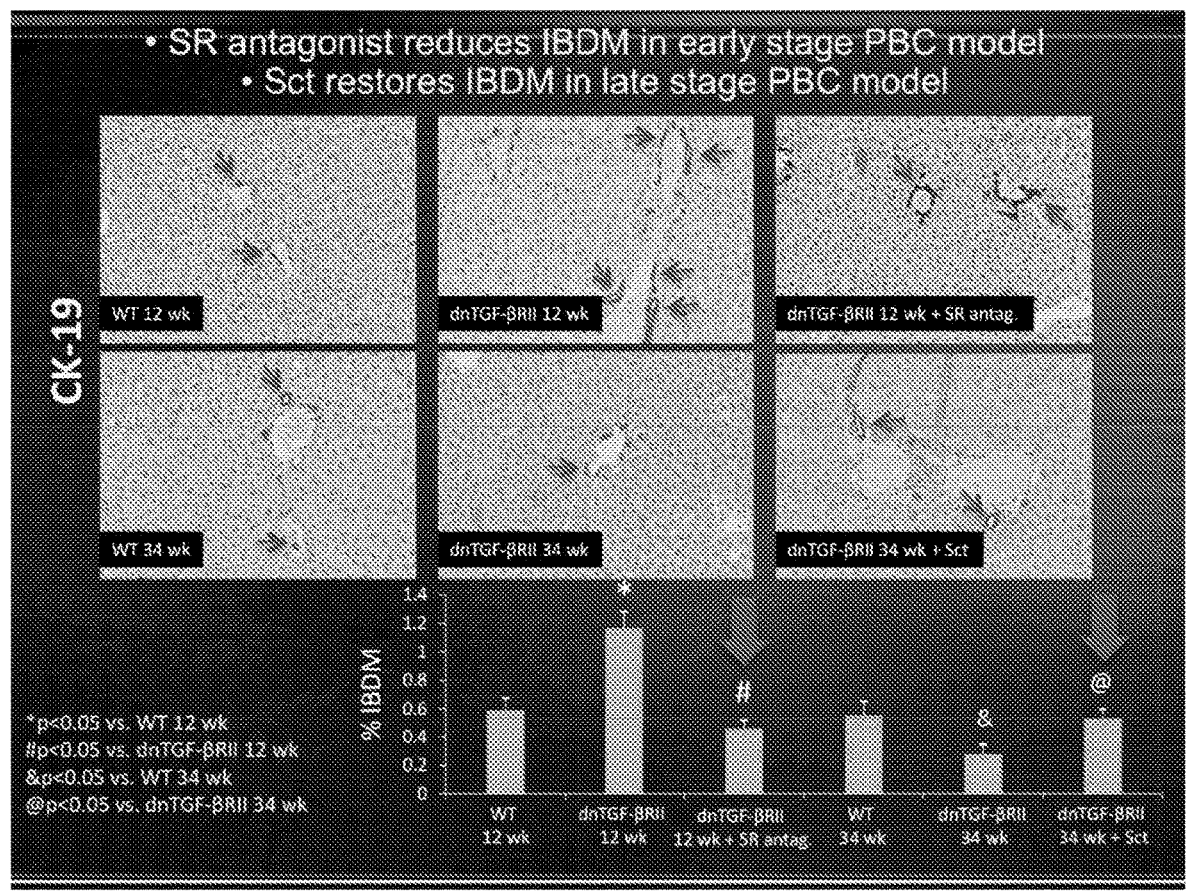
FIG. 1 shows that administration of SR antagonist (SCT 5-27) decreases biliary proliferation in early stage PBC mice (dnTGF-βRII 12 week), while secretin stimulates biliary proliferation in late stage PBC mice (dnTGF-βRII 34 week) returning bile duct mass to normal wild-type (WT) mouse levels. The top panel shows an increase in the number of cytokeratin-19 (CK-19) positive bile ducts in early stage PBC mice, which is reduced in early stage PBC mice treated with SR antagonist. There is an observed reduction in the number of CK-19 positive bile ducts in the late stage PBC mice compared to the normal WT mice (34 wk). Administration of a SR agonist (secretin) increased biliary mass in the late stage PBC mice back to normal levels. Orig. magn., ×40. Bottom histogram illustrates the quantification of the CK-19 expression as the percentage intrahepatic bile duct mass (% IBDM). There is a significant increase in IBDM in the early stage PBC mice, which is significantly reduced in the early stage PBC mice treated with SR antagonist. There is a significant reduction in the IBDM in late stage PBC mice, which is increased in late stage PBC mice treated with SR agonist (secretin). Data are mean±SEM of 3 evaluations from 3 individual mice. $*p<0.05$ vs. WT 12 wk. $\#p<0.05$ vs. dnTGF-βRII 12 wk. $^{\&}p<0.05$ vs WT 34 wk. $^{@}p<0.05$ vs dnTGF-βRII 34 wk.

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells.

Provided herein is a method of modulating a Sct/SR axis in a mammalian subject in need thereof, comprising administering an effective amount of a SR antagonist to said subject. In one embodiment, modulating the Sct/SR axis treats a liver disease in said subject. In certain embodiments, the liver disease is selected from the group of liver diseases consisting of: Early Stage PBC, Primary Sclerosing Cholangitis, Primary Biliary Cholangitis, Biliary Atresia, NASH, NAFLD, and Alcohol induced liver injury. In a particular embodiment, the liver disease is Early Stage PBC.

Also provide is a method of treating Late Stage PBC in a mammalian subject in need thereof, comprising administering an effective amount of a SR agonist to said subject.

Also provided is a method of ameliorating PBC-induced biliary damage in a mammalian subject in need thereof, comprising modulating a Sct/SR axis of said subject. In one embodiment, this method further comprises ameliorating liver fibrosis. In a particular embodiment, the Sct/SR axis is modulated by administering an effective amount of an SR antagonist to said subject.

The phrase "mammalian subject in need thereof" means a mammal, including a human patient, experiencing or suffering a diagnosable or diagnosed liver disease, disorder or dysfunction.

In some embodiments, modulating the Sct/SR axis treats a liver disease in a subject (including, e.g., a human patient). As used herein, the phrase "treats a liver disease in said subject" refers to ameliorating or eliminating at least one clinical symptom of the liver disease in the subject or patient.

As used herein, the phrase "modulating the Sct/SR axis" means: (i) down-regulating or decreasing one or more physiological activity(ies) of a SCT/SR signaling pathway in regulating cholangiocyte function, or alternatively, (ii) up-regulating or increasing the physiological activity one or more physiological activity(ies) of a SCT/SR signaling pathway in regulating cholangiocyte function.

As used herein, the phrase "effective amount" means a dose or quantity of an SR antagonist or SR agonist, as the case may be, that eliminates or ameliorates at least one symptom of a liver disease or disorder in a subject or patient.

As used herein, the phrase "SR antagonist" refers to a molecule, salt, or other ligand that specifically binds to SR and decreases its physiological activity in a SCT/SR signaling pathway. Examples of a SR antagonist is Sec 5-27 oligopeptide, a variant of Sec 5-27, a derivative of Sec 5-27, a Sec 5-27 peptide mimetic, an anti-SR antagonist antibody, or an SR-antagonist small molecule analog of Sec 5-27. Also included among SR antagonists are anti-SR antibody antagonists of SR.

As used herein, the phrase "SR agonist" refers to a molecule, salt, or other ligand that specifically binds to SR and increases its physiological activity in a SCT/SR signaling pathway. Examples of a SR agonist is secretin, a variant of secretin, a derivative of secretin, a secretin peptide mimetic, an anti-SR agonist antibody, an anti-secretin agonist antibody, or a SR-agonist small molecule analog of secretin.

The term "secretin" refers to a polypeptide hormone, commonly secreted by the duodenal and/or jejunal mucosa in mammals, when acid chyme enters the intestine; it stimulates secretion of pancreatic juice and, to a lesser extent, bile and intestinal secretion. Encompassed by "secretin" are any secretin of mammalian origin (e.g., human, rodent, canine, feline, rabbit, monkey, simian, bovine, etc.), variants or sequence modifications and derivatives of secretin, peptide mimetics and small molecule analogs of secretin with physiologically functional SR agonist activity. For example, human secretin is a 27-amino acid peptide (GenBank Accession No. S07443), which is synthesized naturally by the above-mentioned intestinal mucosal cells as a 121-amino acid residue secretin precursor (GenBank Accession No. NP_068739), comprising a signal peptide, short N-terminal peptide, secretin (bold underlined residues in SEQ ID NO:1, below), and a C-terminal peptide sequence:

```
                                            SEQ ID NO: 1
MAPRPLLLLL LLLGGSAARP APPRARR HSD GTFTSELSRL

REGARLQRLL QGLVGKRSEQ DAENSMAWTR LSAGLLCPSG

SNMPILQAWM PLDGTWSPWL PPGPMVSEPA GAAAEGTLRP R//.
```

The human secretin precursor gene, SCT, is located on chromosome 11p15.5; SCT consists of four exons, and the secretin coding region is exon 2.

"Sec 5-27" or interchangeably "SCT 5-27"—also known as 15-lysine-secretin-(5-27)—is a truncated oligopeptide in which the amino acid residue in position 15 of human secretin (HSDGTFTSEL SRLREGARLQ RLLQGLV//SEQ ID NO:2), is replaced by lysine; i.e., TFTSELSRLRKGARLQ RLLQGLV//SEQ ID NO:3 is the "Sec 5-27" or "SCT 5-27" amino acid sequence. (See, Bodansky, M. et al., *Synthesis and some pharmacological properties of the 23-peptide 15-lysine-secretin-(5-27). Special role of the residue in position 15 in biological activity of the vasoactive intestinal polypeptide*, J. Med. Chem. 21(11):1171-73 (1978)).

"Polypeptide" and "protein" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs (i.e., non-canonical or unnatural amino acids) are included as can be expressed recombinantly using known protein engineering techniques. In addition, fusion proteins can be derivatized as described herein by well-known organic chemistry techniques.

A "variant" of a polypeptide (e.g., a secretin, an immunoglobulin, or an antibody) comprises an amino acid sequence wherein one or more amino acid residues are inserted into, deleted from and/or substituted into the amino acid sequence relative to another polypeptide sequence. Insertion or substitution of non-canonical or non-natural amino acids is encompassed by "variant." Variants also include fusion proteins. The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with a nucleotide sequence encoding a polypeptide sequence from a different protein (optionally separated by a linker sequence between the two heterologous protein sequences). The fusion gene can then be expressed by a recombinant host cell as a single protein.

The term "modification" when used in connection with proteins of interest, include, but are not limited to, one or more amino acid changes (including substitutions, insertions or deletions); chemical modifications; covalent modification by conjugation to therapeutic or diagnostic agents; labeling (e.g., with radionuclides or various enzymes); covalent polymer attachment such as PEGylation (derivatization with polyethylene glycol) and insertion or substitution by chemical synthesis of non-natural amino acids. By methods known to the skilled artisan, proteins, can be "engineered" or modified for improved target affinity, selectivity, stability, and/or manufacturability before the protein is biochemically synthesized, or its coding sequence is "engineered" for inclusion in a recombinant expression cassette used to express the polypeptide by recombinant protein expression.

The term "derivative," when used in connection with proteins of interest, refers to proteins that are modified by covalent conjugation to other therapeutic or diagnostic agents or moieties, or to a label or marker (e.g., a radionuclide or one or more various enzymes), or are covalently conjugated to a polymer, such as polyethylene glycol (PEGylation) or biotin (biotinylation).

The term "recombinant protein" or "recombinant polypeptide" as used herein refers to a protein (or used interchangeably herein, a polypeptide or an oligopeptide) molecule which is expressed using a recombinant DNA molecule. A "recombinant host cell" is a cell that contains and/or expresses a recombinant nucleic acid.

The term "naturally occurring," where it occurs in the specification in connection with biological materials such as polypeptides, nucleic acids, host cells, and the like, refers to materials which are found in nature.

As used herein, the phrase "Early Stage PBC" (or early stage Primary Biliary Cholangitis) refers to stages I-II in which there is intense ductular reaction (proliferation of small ducts) along with periportal inflammation. In accordance with the present invention, it has been found that the Secretin Receptor antagonists are effective for treating early stage PBC since bile ducts cells are proliferating and it is beneficial at that point to inhibit proliferation.

As used herein, the phrase "Late Stage PBC" (or Advanced or late stage Primary Biliary Cholangitis) refers to stages in which you have apoptosis, duct loss and intense fibrogenesis and/or development of cirrhosis (stage IV). Late or Advanced stage PBC can also be characterized by periportal fibrosis with portal-portal bridging fibrosis and ductopenia (loss of small ducts) that can develop into cirrhosis. In one embodiment, Late Stage PBC (Advanced PBC) can identified clinically by detecting increases in liver stiffness (>9.6 kpa) or raises in bilirubin (>1 mg/dl). In accordance with the present invention, it has been found that Secretin, and other SR agonists that stimulate the secretin/SR axis, are effective for treating late stage PBC because there is no longer bile duct proliferation. In embodiments of the present invention where cirrhosis is treated, the reduction in platelet count, albumin serum levels and increases in INR can be used to clinically identify cirrhosis to be treated.

The term "peptide analog" refers to a peptide having a sequence that differs from a peptide sequence existing in nature by at least one amino acid residue substitution, internal addition, or internal deletion of at least one amino acid, and/or amino- or carboxy-terminal end truncations or additions, and/or carboxy-terminal amidation. An "internal deletion" refers to absence of an amino acid from a sequence existing in nature at a position other than the N- or C-terminus. Likewise, an "internal addition" refers to presence of an amino acid in a sequence existing in nature at a position other than the N- or C-terminus.

The terms "mimetic peptide," "peptide mimetic," and "agonist peptide" refer to a peptide or protein having biological activity comparable to a naturally occurring protein of interest, e.g., secretin. These terms further include peptides that indirectly mimic the activity of a naturally occurring peptide molecule, such as by potentiating the effects of the naturally occurring molecule.

The term "antagonist peptide," "peptide antagonist," and "inhibitor peptide" refer to a peptide that blocks or in some way interferes with the biological activity of a receptor of interest, e.g., the secretin receptor (SR), or has biological activity comparable to a known antagonist or inhibitor of a receptor of interest.

A "domain" of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

As used herein "soluble" when in reference to a protein produced by recombinant DNA technology in a host cell is a protein that exists in aqueous solution; if the protein contains a twin-arginine signal amino acid sequence the soluble protein is exported to the periplasmic space in gram negative bacterial hosts, or is secreted into the culture medium by eukaryotic host cells capable of secretion, or by bacterial host possessing the appropriate genes (e.g., the kill gene). Thus, a soluble protein is a protein which is not found in an inclusion body inside the host cell. Alternatively, depending on the context, a soluble protein is a protein which is not found integrated in cellular membranes. In contrast, an insoluble protein is one which exists in denatured form inside cytoplasmic granules (called an inclusion body) in the host cell, or again depending on the context, an insoluble protein is one which is present in cell membranes, including but not limited to, cytoplasmic membranes, mitochondrial membranes, chloroplast membranes, endoplasmic reticulum membranes, etc.

A distinction is also drawn between proteins which are "soluble" (i.e., dissolved or capable of being dissolved) in an aqueous solution devoid of significant amounts of ionic detergents (e.g., SDS) or denaturants (e.g., urea, guanidine hydrochloride) and proteins which exist as a suspension of insoluble protein molecules dispersed within the solution. A "soluble" protein will not be removed from a solution containing the protein by centrifugation using conditions sufficient to remove cells present in a liquid medium (e.g., centrifugation at 5,000×g for 4-5 minutes).

A "secreted" protein refers to those proteins capable of being directed to the ER, secretory vesicles, or the extracellular space as a result of a secretory signal peptide sequence, as well as those proteins released into the extracellular space without necessarily containing a signal sequence. If the secreted protein is released into the extracellular space, the secreted protein can undergo extracellular processing to produce a "mature" protein. Release into the extracellular space can occur by many mechanisms, including exocytosis and proteolytic cleavage.

Pharmaceutical Compositions

In General. The present invention also provides pharmaceutical compositions comprising the inventive composition of matter and a pharmaceutically acceptable carrier. Such pharmaceutical compositions can be configured for administration to a patient by a wide variety of delivery routes, e.g., an intravascular delivery route such as by injection or infusion, subcutaneous, intramuscular, intraperitoneal, epidural, or intrathecal delivery routes, or for oral, enteral, pulmonary (e.g., inhalant), intranasal, transmucosal (e.g., sublingual administration), transdermal or other delivery routes and/or forms of administration known in the art. The inventive pharmaceutical compositions may be prepared in liquid form, or may be in dried powder form, such as lyophilized form. For oral or enteral use, the pharmaceutical compositions can be configured, for example, as tablets, troches, lozenges, aqueous or oily suspensions, dispersible powders or granules, emulsions, hard or soft capsules, syrups, elixirs or enteral formulas.

In the practice of this invention the "pharmaceutically acceptable carrier" is any physiologically tolerated substance known to those of ordinary skill in the art useful in formulating pharmaceutical compositions, including, any pharmaceutically acceptable diluents, excipients, dispersants, binders, fillers, glidants, anti-frictional agents, compression aids, tablet-disintegrating agents (disintegrants), suspending agents, lubricants, flavorants, odorants, sweeteners, permeation or penetration enhancers, preservatives, surfactants, solubilizers, emulsifiers, thickeners, adjuvants, dyes, coatings, encapsulating material(s), and/or other additives singly or in combination. Such pharmaceutical compositions can include diluents of various buffer content (e.g., Tris-HCl, acetate, phosphate), pH and ionic strength; additives such as detergents and solubilizing agents (e.g., Tween® 80, Polysorbate 80), anti-oxidants (e.g., ascorbic acid, sodium metabisulfite), preservatives (e.g., Thimersol®, benzyl alcohol) and bulking substances (e.g., lactose, mannitol); incorporation of the material into particulate preparations of polymeric compounds such as polylactic acid, polyglycolic acid, etc. or into liposomes. Hyaluronic acid can also be used, and this can have the effect of promoting sustained duration in the circulation. Such compositions can influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435-1712, which are herein incorporated by reference in their entirety. The compositions can be prepared in liquid form, or can be in dried powder, such as lyophilized form. Implantable sustained release formulations are also useful, as are transdermal or transmucosal formulations. Additionally (or alternatively), the present invention provides compositions for use in any of the various slow or sustained release formulations or microparticle formulations known to the skilled artisan, for example, sustained release microparticle formulations, which can be administered via pulmonary, intranasal, or subcutaneous delivery routes. (See, e.g., Murthy et al, Injectable compositions for the controlled delivery of pharmacologically active compound, U.S. Pat. No. 6,887,487; Manning et al., Solubilization of pharmaceutical substances in an organic solvent and preparation of pharmaceutical powders using the same, U.S. Pat. Nos. 5,770,559 and 5,981,474; Lieberman et al, Lipophilic complexes of pharmacologically active inorganic mineral acid esters of organic compounds, U.S. Pat. No. 5,002,936; Gen, Formative agent of protein complex, US 2002/0119946 A1; Goldenberg et al, Sustained release formulations, WO 2005/105057 A1).

One can dilute the inventive compositions or increase the volume of the pharmaceutical compositions of the invention with an inert material. Such diluents can include carbohydrates, especially, mannitol, a-lactose, anhydrous lactose, cellulose, sucrose, modified dextrans and starch. Certain inorganic salts may also be used as fillers, including calcium triphosphate, magnesium carbonate and sodium chloride. Some commercially available diluents are Fast-Flo, Emdex, STA-Rx 1500, Emcompress and Avicell.

A variety of conventional thickeners are useful in creams, ointments, suppository and gel configurations of the pharmaceutical composition, such as, but not limited to, alginate, xanthan gum, or petrolatum, may also be employed in such configurations of the pharmaceutical composition of the present invention. A permeation or penetration enhancer, such as polyethylene glycol monolaurate, dimethyl sulfoxide, N-vinyl-2-pyrrolidone, N-(2-hydroxyethyl)-pyrrolidone, or 3-hydroxy-N-methyl-2-pyrrolidone can also be employed. Useful techniques for producing hydrogel matrices are known. (E.g., Feijen, Biodegradable hydrogel matrices for the controlled release of pharmacologically active agents, U.S. Pat. No. 4,925,677; Shah et al, Biodegradable pH/thermosensitive hydrogels for sustained delivery of biologically active agents, WO 00/38651 A1). Such biodegradable gel matrices can be formed, for example, by crosslinking a proteinaceous component and a polysaccharide or mucopolysaccharide component, then loading with the inventive composition of matter to be delivered.

Liquid pharmaceutical compositions of the present invention that are sterile solutions or suspensions can be administered to a patient by injection, for example, intramuscularly, intrathecally, epidurally, intravascularly (e.g., intravenously or intraarterially), intraperitoneally or subcutaneously. (See, e.g., Goldenberg et al, Suspensions for the sustained release of proteins, U.S. Pat. No. 6,245,740 and WO 00/38652 A1). Sterile solutions can also be administered by intravenous infusion. The inventive composition can be included in a sterile solid pharmaceutical composition, such as a lyophilized powder, which can be dissolved or suspended at a convenient time before administration to a patient using sterile water, saline, buffered saline or other appropriate sterile injectable medium.

Implantable sustained release formulations are also useful embodiments of the inventive pharmaceutical compositions. For example, the pharmaceutically acceptable carrier, being a biodegradable matrix implanted within the body or under the skin of a human or non-human vertebrate, can be a hydrogel similar to those described above. Alternatively, it may be formed from a poly-alpha-amino acid component. (Sidman, Biodegradable, implantable drug delivery device, and process for preparing and using same, U.S. Pat. No. 4,351,337). Other techniques for making implants for delivery of drugs are also known and useful in accordance with the present invention.

In powder forms, the pharmaceutically acceptable carrier is a finely divided solid, which is in admixture with finely divided active ingredient(s), including the inventive composition. For example, in some embodiments, a powder form is useful when the pharmaceutical composition is configured as an inhalant. (See, e.g., Zeng et al, Method of preparing dry powder inhalation compositions, WO 2004/017918; Trunk et al., Salts of the CGRP antagonist BIBN4096 and inhalable powdered medicaments containing them, U.S. Pat. No. 6,900,317).

One can dilute or increase the volume of the compound of the invention with an inert material. These diluents could include carbohydrates, especially mannitol, a-lactose, anhydrous lactose, cellulose, sucrose, modified dextrans and starch. Certain inorganic salts can also be used as fillers including calcium triphosphate, magnesium carbonate and sodium chloride. Some commercially available diluents are Fast-Flo™, Emdex™, STA-Rx™ 1500, Emcompress™ and Avicell™.

Disintegrants can be included in the formulation of the pharmaceutical composition into a solid dosage form. Materials used as disintegrants include but are not limited to starch including the commercial disintegrant based on starch, Explotab™. Sodium starch glycolate, Amberlite™, sodium carboxymethylcellulose, ultramylopectin, sodium alginate, gelatin, orange peel, acid carboxymethyl cellulose, natural sponge and bentonite can all be used. Insoluble cationic exchange resin is another form of disintegrant. Powdered gums can be used as disintegrants and as binders and these can include powdered gums such as agar, Karaya or tragacanth. Alginic acid and its sodium salt are also useful as disintegrants.

Binders can be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic. An antifrictional agent can be included in the formulation of the therapeutic to prevent sticking during the formulation process. Lubricants can be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants can also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants can include starch, talc, pyrogenic silica and hydrated silicoaluminate.

To aid dissolution of the compound of this invention into the aqueous environment a surfactant might be added as a wetting agent. Surfactants can include anionic detergents such as sodium lauryl sulfate, dioctyl sodium sulfosuccinate and dioctyl sodium sulfonate. Cationic detergents might be used and could include benzalkonium chloride or benzethonium chloride. The list of potential nonionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of the protein or derivative either alone or as a mixture in different ratios.

Oral dosage forms. Also useful are oral dosage forms of the inventive compositions. If necessary, the composition can be chemically modified so that oral delivery is efficacious. Generally, the chemical modification contemplated is the attachment of at least one moiety to the molecule itself, where said moiety permits (a) inhibition of proteolysis; and (b) uptake into the blood stream from the stomach or intestine. Also desired is the increase in overall stability of the compound and increase in circulation time in the body. Moieties useful as covalently attached half-life extending moieties in this invention can also be used for this purpose. Examples of such moieties include: PEG, copolymers of ethylene glycol and propylene glycol, carboxymethyl cellulose, dextran, polyvinyl alcohol, polyvinyl pyrrolidone and polyproline. See, for example, Abuchowski and Davis (1981), Soluble Polymer-Enzyme Adducts, Enzymes as Drugs (Hocenberg and Roberts, eds.), Wiley-Interscience, New York, N.Y., pp 367-83; Newmark, et al. (1982), J. Appl. Biochem. 4: 185-9. Other polymers that could be used are poly-1,3-dioxolane and poly-1,3,6-tioxocane. Preferred for pharmaceutical usage, as indicated above, are PEG moieties.

For oral delivery dosage forms, it is also possible to use a salt of a modified aliphatic amino acid, such as sodium N-(8-[2-hydroxybenzoyl] amino) caprylate (SNAC), as a carrier to enhance absorption of the therapeutic compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods."

In one embodiment, the pharmaceutically acceptable carrier can be a liquid and the pharmaceutical composition is prepared in the form of a solution, suspension, emulsion, syrup, elixir or pressurized composition. The active ingredient(s) (e.g., the inventive composition of matter) can be dissolved, diluted or suspended in a pharmaceutically acceptable liquid carrier such as water, an organic solvent, a mixture of both, or pharmaceutically acceptable oils or fats. The liquid carrier can contain other suitable pharmaceutical additives such as detergents and/or solubilizers (e.g., Tween 80, Polysorbate 80), emulsifiers, buffers at appropriate pH (e.g., Tris-HCl, acetate, phosphate), adjuvants, anti-oxidants (e.g., ascorbic acid, sodium metabisulfite), preservatives (e.g., Thimersol, benzyl alcohol), sweeteners, flavoring agents, suspending agents, thickening agents, bulking substances (e.g., lactose, mannitol), colors, viscosity regulators, stabilizers, electrolytes, osmolutes or osmo-regulators. Additives can also be included in the formulation to enhance uptake of the inventive composition. Additives potentially having this property are for instance the fatty acids oleic acid, linoleic acid and linolenic acid.

Useful are oral solid dosage forms, which are described generally in Remington's Pharmaceutical Sciences (1990), supra, in Chapter 89, which is hereby incorporated by reference in its entirety. Solid dosage forms include tablets, capsules, pills, troches or lozenges, cachets or pellets. Also, liposomal or proteinoid encapsulation can be used to formulate the present compositions (as, for example, proteinoid microspheres reported in U.S. Pat. No. 4,925,673). Liposomal encapsulation can be used and the liposomes can be derivatized with various polymers (e.g., U.S. Pat. No. 5,013,556). A description of possible solid dosage forms for the therapeutic is given in Marshall, K., Modern Pharmaceutics (1979), edited by G. S. Banker and C. T. Rhodes, in Chapter 10, which is hereby incorporated by reference in its entirety. In general, the formulation will include the inventive compound, and inert ingredients that allow for protection against the stomach environment, and release of the biologically active material in the intestine.

The composition of this invention can be included in the formulation as fine multiparticulates in the form of granules or pellets of particle size about 1 mm. The formulation of the material for capsule administration could also be as a powder, lightly compressed plugs or even as tablets. The therapeutic could be prepared by compression.

Colorants and flavoring agents can all be included. For example, the protein (or derivative) can be formulated (such as by liposome or microsphere encapsulation) and then further contained within an edible product, such as a refrigerated beverage containing colorants and flavoring agents.

In tablet form, the active ingredient(s) are mixed with a pharmaceutically acceptable carrier having the necessary compression properties in suitable proportions and compacted in the shape and size desired.

The powders and tablets preferably contain up to 99% of the active ingredient(s). Suitable solid carriers include, for example, calcium phosphate, magnesium stearate, talc, sugars, lactose, dextrin, starch, gelatin, cellulose, polyvinylpyrrolidine, low melting waxes and ion exchange resins.

Controlled release formulation can be desirable. The composition of this invention can be incorporated into an inert matrix that permits release by either diffusion or leaching mechanisms e.g., gums. Slowly degenerating matrices can also be incorporated into the formulation, e.g., alginates, polysaccharides. Another form of a controlled release of the compositions of this invention is by a method based on the Oros™ therapeutic system (Alza Corp.), i.e., the drug is enclosed in a semipermeable membrane which allows water to enter and push drug out through a single small opening due to osmotic effects. Some enteric coatings also have a delayed release effect.

Other coatings can be used for the formulation. These include a variety of sugars that could be applied in a coating pan. The therapeutic agent could also be given in a film-coated tablet and the materials used in this instance are divided into 2 groups. The first are the nonenteric materials and include methylcellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols. The second group consists of the enteric materials that are commonly esters of phthalic acid.

A mix of materials might be used to provide the optimum film coating. Film coating can be carried out in a pan coater or in a fluidized bed or by compression coating.

Pulmonary delivery forms. Pulmonary delivery of the inventive compositions is also useful. The protein (or derivative) is delivered to the lungs of a mammal while inhaling and traverses across the lung epithelial lining to the blood stream. (Other reports of this include Adjei et al., Pharma. Res. (1990) 7: 565-9; Adjei et al. (1990), Internatl. J. Pharmaceutics 63: 135-44 (leuprolide acetate); Braquet et al. (1989), J. Cardiovasc. Pharmacol. 13 (suppl.5): s.143-146 (endothelin-1); Hubbard et al. (1989), Annals Int. Med. 3: 206-12 (a 1-antitrypsin); Smith et al—(1989), J. Clin. Invest. 84: 1145-6 (a 1-proteinase); Oswein et al. (March 1990), "Aerosolization of Proteins," Proc. Svmp. Resp. Drug Delivery II, Keystone, Colo. (recombinant human growth hormone); Debs et al. (1988), J. Immunol. 140: 3482-8 (interferon-γ and tumor necrosis factor a) and Platz et al., U.S. Pat. No. 5,284,656 (granulocyte colony stimulating factor).

Useful in the practice of this invention are a wide range of mechanical devices designed for pulmonary delivery of therapeutic products, including but not limited to nebulizers, metered dose inhalers, and powder inhalers, all of which are familiar to those skilled in the art. Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; and the Spinhaler powder inhaler, manufactured by Fisons Corp., Bedford, Mass. (See, e.g., Helgesson et al, Inhalation device, U.S. Pat. No. 6,892,728; McDerment et al, Dry powder inhaler, WO 02/11801 A1; Ohki et al, Inhalant medicator, U.S. Pat. No. 6,273,086). All such devices require the use of formulations suitable for the dispensing of the inventive compound. Typically, each formulation is specific to the type of device employed and can involve the use of an appropriate propellant material, in addition to diluents, adjuvants and/or carriers useful in therapy.

The inventive compound should most advantageously be prepared in particulate form with an average particle size of less than 10μm (or microns), most preferably 0.5 to 5μm, for most effective delivery to the distal lung.

Pharmaceutically acceptable excipients include carbohydrates such as trehalose, mannitol, xylitol, sucrose, lactose, and sorbitol. Other ingredients for use in formulations can include DPPC, DOPE, DSPC and DOPC. Natural or synthetic surfactants can be used. PEG can be used (even apart from its use in derivatizing the protein or analog). Dextrans, such as cyclodextran, can be used. Bile salts and other related enhancers can be used. Cellulose and cellulose derivatives can be used. Amino acids can be used, such as use in a buffer formulation.

Also, the use of liposomes, microcapsules or microspheres, inclusion complexes, or other types of carriers is contemplated.

Formulations suitable for use with a nebulizer, either jet or ultrasonic, will typically comprise the inventive compound dissolved in water at a concentration of about 0.1 to 25 mg of biologically active protein per mL of solution. The formulation can also include a buffer and a simple sugar (e.g., for protein stabilization and regulation of osmotic pressure). The nebulizer formulation can also contain a surfactant, to reduce or prevent surface induced aggregation of the protein caused by atomization of the solution in forming the aerosol.

Formulations for use with a metered-dose inhaler device will generally comprise a finely divided powder containing the inventive compound suspended in a propellant with the aid of a surfactant. The propellant can be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid can also be useful as a surfactant. (See, e.g., Backstrom et al, Aerosol drug formulations containing hydrofluoroalkanes and alkyl saccharides, U.S. Pat. No. 6,932,962).

Formulations for dispensing from a powder inhaler device will comprise a finely divided dry powder containing the inventive compound and can also include a bulking agent, such as lactose, sorbitol, sucrose, mannitol, trehalose, or xylitol in amounts which facilitate dispersal of the powder from the device, e.g., 50 to 90% by weight of the formulation.

Nasal delivery forms. In accordance with the present invention, intranasal delivery of the inventive composition of matter and/or pharmaceutical compositions is also useful, which allows passage thereof to the blood stream directly after administration to the inside of the nose, without the necessity for deposition of the product in the lung. Formulations suitable for intransal administration include those with dextran or cyclodextran, and intranasal delivery devices are known. (See, e.g, Freezer, Inhaler, U.S. Pat. No. 4,083,368).

Transdermal and transmucosal (e.g., buccal) delivery forms). In some embodiments, the inventive composition is configured as a part of a pharmaceutically acceptable transdermal or transmucosal patch or a troche. Transdermal patch drug delivery systems, for example, matrix type transdermal patches, are known and useful for practicing some embodiments of the present pharmaceutical compositions. (E.g., Chien et al, Transdermal estrogen/progestin dosage unit, system and process, U.S. Pat. Nos. 4,906,169 and 5,023,084; Cleary et al., Diffusion matrix for transdermal drug administration and transdermal drug delivery devices including same, U.S. Pat. No. 4,911,916; Teillaud et al., EVA-based transdermal matrix system for the administration of an estrogen and/or a progestogen, U.S. Pat. No. 5,605,702; Venkateshwaran et al., Transdermal drug delivery matrix for coadministering estradiol and another steroid, U.S. Pat. No. 5,783,208; Ebert et al, Methods for providing testosterone and optionally estrogen replacement therapy to women, U.S. Pat. No. 5,460,820). A variety of pharmaceutically acceptable systems for transmucosal delivery of therapeutic agents are also known in the art and are compatible with the practice of the present invention. (E.g., Heiber et al., Transmucosal delivery of macromolecular drugs, U.S. Pat. Nos. 5,346,701 and 5,516,523; Longenecker et al, Transmembrane formulations for drug administration, U.S. Pat. No. 4,994,439).

Buccal delivery of the inventive compositions is also useful. Buccal delivery formulations are known in the art for use with peptides. For example, known tablet or patch systems configured for drug delivery through the oral mucosa (e.g., sublingual mucosa), include some embodiments that comprise an inner layer containing the drug, a permeation enhancer, such as a bile salt or fusidate, and a hydrophilic polymer, such as hydroxypropyl cellulose, hydroxypropyl methylcellulose, hydroxyethyl cellulose, dextran, pectin, polyvinyl pyrrolidone, starch, gelatin, or any number of other polymers known to be useful for this purpose. This inner layer can have one surface adapted to contact and adhere to the moist mucosal tissue of the oral cavity and can have an opposing surface adhering to an overlying non-adhesive inert layer. Optionally, such a transmucosal delivery system can be in the form of a bilayer tablet, in which the inner layer also contains additional binding agents, flavoring agents, or fillers. Some useful systems employ a non-ionic detergent along with a permeation enhancer. Transmucosal delivery devices may be in free form, such as a cream, gel, or ointment, or may comprise a determinate form such as a tablet, patch or troche. For example, delivery of the inventive composition can be via a transmucosal delivery system comprising a laminated composite of, for example, an adhesive layer, a backing layer, a permeable membrane defining a reservoir containing the inventive composition, a peel seal disc underlying the membrane, one or more heat seals, and a removable release liner. (E.g., Ebert et al, Transdermal delivery system with adhesive overlay and peel seal disc, U.S. Pat. No. 5,662,925; Chang et al., Device for administering an active agent to the skin or mucosa, U.S. Pat. Nos. 4,849,224 and 4,983,395). These examples are merely illustrative of available transmucosal drug delivery technology and are not limiting of the present invention.

Dosages.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.1-1000 micrograms of the inventive compound per kilogram of body weight, preferably 0.1-150 micrograms per kilogram.

By way of further illustration, the following numbered embodiments are encompassed by the present invention:

Embodiment 1

A method of modulating the Sct/SR axis in a mammalian subject in need thereof, comprising administering an effective amount of a SR antagonist to said subject.

Embodiment 2

The method of Embodiment 1, wherein modulating the Sct/SR axis treats a liver disease in said subject.

Embodiment 3

The method of Embodiments 1-2, wherein the mammalian subject is a human.

Embodiment 4

The use of a SR antagonist to treat a liver disease selected from the group consisting of Early Stage PBC, Primary Sclerosing Cholangitis, Primary Biliary Cholangitis, Biliary Atresia, NASH, NAFLD, and Alcohol induced liver injury.

Embodiment 5

The use of Embodiment 4, wherein the liver disease is Early Stage PBC.

Embodiment 6

The use of a SR agonist to treat Late Stage PBC.

Embodiment 7

The use of Embodiment 7, wherein the SR agonist is secretin or a variant or derivative thereof or a small molecule analog thereof.

Embodiment 8

The use Embodiments 4-7 to ameliorate PBC-induced biliary damage.

Embodiment 9

The use of Embodiments 4-8 to ameliorate liver fibrosis.

Embodiment 10

A pharmaceutical composition for modulating the Sct/SR axis, comprising a SR antagonist or a SR agonist, and a pharmaceutically acceptable carrier or excipient.

Embodiment 11

The pharmaceutical composition of Embodiment 10, comprising a SR antagonist.

Embodiment 12

The pharmaceutical composition of Embodiments 10-11, wherein the SR antagonist is selected from the group consisting of Sec 5-27, a variant of Sec 5-27, a derivative of Sec 5-27, a Sec 5-27 peptide mimetic, an anti-SR antagonist antibody, and a SR-antagonist small molecule analog of Sec 5-27.

Embodiment 13

The pharmaceutical composition of Embodiments 10-12, comprising Sec 5-27.

Embodiment 14

The pharmaceutical composition of Embodiment 10, comprising a SR agonist.

Embodiment 15

The pharmaceutical composition of Embodiments 10 and 14, wherein the SR agonist is selected from the group consisting of secretin, a variant of secretin, a derivative of secretin, a secretin peptide mimetic, an anti-SR agonist antibody, an anti-secretin agonist antibody, an SR-agonist small molecule analog of secretin.

Embodiment 16

The pharmaceutical composition of Embodiment 15, comprising secretin.

The following working examples are illustrative and not to be construed in any way as limiting the scope of the invention.

EXAMPLES

Example 1. Biliary Damage and Liver Fibrosis are Ameliorated Following Secretin Receptor Antagonist Treatment in a Mouse Model of Early Stage Primary Biliary Cholangitis (PBC), but Exacerbated During Late Stage PBC Background.

Early stage Primary Biliary Cholangitis (PBC) is evidenced by ductular reaction and mild fibrosis, whereas late stage PBC is characterized by ductopenia and bridging fibrosis. Secretin (Sec) is secreted by cholangiocytes and binds to its receptor (SR) to stimulate biliary proliferation and hepatic fibrosis. The dnTGFβRII mice at 12 wk of age mimic early stage PBC, but at 32-34 wk of age mimic late stage PBC. Previously, we have shown that Sec/SR signaling is upregulated during early stage PBC, but reduced during late stage PBC in mouse models and human PBC patients. Therefore, we aimed to evaluate the therapeutic potential of SR antagonist treatment in dnTGFβRII mice and human PBC.

Methods.

Briefly, we used wild-type (WT), dnTGFβRII 12 wk and dnTGFβRII 34 wk mice treated with control or SR antagonist (SCT 5-27) minipump (10 µg/kg/day) for 1 wk. Hepatic damage was shown by H&E. IBDM and cholangiocyte proliferation were measured by immunohistochemistry for CK-19 and Ki67, respectively. Biliary apoptosis was evaluated by TUNEL staining. Senescence was measured in cholangiocytes by immunofluorescence for CCL2 or p16 co-stained with CK-19 (to image bile ducts) and SA-β-Galactosidase activity. Hepatic fibrosis was assessed by qPCR for collagen-1a and α-SMA in total liver, and quantification of Sirius Red staining. Hepatic stellate cell (HSC) activation was evaluated by immunofluorescence (IF) for Syp-9. HSC senescence was evaluated by IF for CCL2 or p16 co-stained with desmin (to visualize HSCs). Secretin levels in serum and bile were measured by EIA. Bile and serum were obtained from human control, early PBC and advanced PBC patients, and secretin was evaluated by EIA.

All reagents were obtained from Sigma-Aldrich, Co (St. Louis, Mo.) unless otherwise indicated. Cell culture reagents and media were obtained from Invitrogen Corporation (Carlsbad, Calif.). Antibodies for immunohistochemistry and immunofluorescence were obtained from Abcam (Cambridge, Mass.) unless indicated otherwise. Total RNA was isolated from total liver tissues and purified cholangiocytes using the TRI Reagent from Sigma Life Science and reverse transcribed with the Reaction Ready First Strand cDNA Synthesis kit (SABiosciences, Frederick, Md.) as described. Total RNA was extract from formalin-fixed, paraffin-embedded liver sections obtained from 3 control, 3 early stage PBC and 3 advanced stage PBC patients using the RNeasy FFPE kit (Qiagen, Valencia, Calif.) and reverse transcribed with the Reaction Ready First Strand cDNA Synthesis kit (SABiosciences, Frederick, Md.).

The selected primers were purchased from Qiagen (Valencia, Calif.). The following primers were used: glyceraldehyde-3-phosphate dehydrogenase (GAPDH), mouse-PPM02946E-200; secretin (Sct), mouse-PPM25163A-200; Sct receptor (SR), mouse-PPM32676F-200; cystic fibrosis transmembrane conductance regulator (CFTR), mouse-PPM04105F-200; Cl$^-$/HCO$_3^-$ AE2 (AE2), mouse-PPM25131A-200; cyclin-dependent kinase inhibitor 2A (p16), mouse-PPM02906F-200; cyclin-dependent kinase inhibitor 2C (p18), mouse-PPM02893C-200; cyclin-dependent kinase inhibitor 1A (p21), mouse-PPM02901B-200; C—C motif chemokine ligand 2 (CCL2), mouse-PPM03151G-200; GAPDH, human-PPH00150E-200; Sct, human-PPH60555B-200; SR, human-PPH18173F-200; CFTR, human-PPH01387F-200; AE2, human-PPH01249A-200.

Animal Models.

All animal procedures were performed according to protocols approved by the Baylor Scott & White Health IACUC Committee. Transgenic mice expressing a dominant-negative form of the human transforming growth factor-beta receptor II (dnTGF-βRII) were obtained from Dr. M. Eric Gershwin at UC Davis Health (Sacramento, Calif.), and background-matched wild-type (WT, strain C57BL/6) mice were purchased from Charles River Laboratories (Wilmington, Mass.); the breeding colony is established in our animal facility. Animals were maintained in micro-isolator cages in a temperature-controlled environment with 12/12-hr light/dark cycles and fed ad libitum standard chow with free access to drinking water. Studies were performed in 12 wk-old WT mice, and 12 wk-old (mimic early stage PBC) and 32 wk-old (mimic late stage PBC) female and male dnTGF-βRII mice (25-30 gm) that were treated with either saline, secretin (Sct; 2.5 nmoles/kg body weight per day; Bachem, Torrance, Calif.) or the secretin receptor (SR) antagonist, Sec 5-27 (10 µg/kg body weight per day; Thermo Fisher Scientific, Waltham, Mass.) for 1 wk by intraperitoneally implanted osmotic minipump. Liver tissue samples and blocks (formalin-fixed, paraffin-embedded and OCT-embedded), serum, bile, cholangiocytes, and cholangiocyte supernatants (after incubation at 37° C. for 4 hr) were collected as described.

Human Samples.

Human serum, bile and liver blocks (formalin-fixed, paraffin-embedded) were collected from patients diagnosed with either early stage PBC, advanced stage PBC and non-diseased controls.

Staging of the PBC samples was determined as follows: Stage 1 was characterized by portal inflammation with destruction of bile ducts; Stage 2 was defined by periportal hepatitis and bile duct proliferation; Stage 3 was further identified by fibrous septa or bridging necrosis; and Stage 4 is further characterized by cirrhosis (Ludwig, J et al., *Staging of chronic nonsuppurative destructive cholangitis (syndrome of primary biliary cirrhosis)*. Virchows Arch A Pathol Anat Histol 379:103-11223 (1978)). All samples were obtained from Dr. Pietro Invernizzi (Humanitas Research Hospital, Rozzano, Italy) and were collected by need biopsy under a protocol approved by the ethics committee by the Humanitas Research Hospital; the protocol was approved by the Veterans' Administration IRB and R&D committee, and by the Texas A&M Health Science Center IRB.

Isolated Cholangiocytes and Cell Lines.

Cholangiocytes were obtained by immunoaffinity separation (See, Wu, N et al., *The secretin/secretin receptor axis modulates liver fibrosis through changes in transforming growth factor-beta*1 *biliary secretion in mice*, Hepatology 64:865-879 (2016)) by using a monoclonal antibody, rat IgG$_{2a}$ (a gift from Dr. R. Faris, Brown University, Providence, R.I.), against an unidentified antigen expressed by all mouse cholangiocytes. Following cholangiocyte isolation, supernatants were collected (after incubation at 37° C. for 4 hr) as described (Kennedy, L L et al., *Knockout of microRNA-21 reduces biliary hyperplasia and liver fibrosis in cholestatic bile duct ligated mice*, Lab Invest 96:1256-1267 (2016)).

In vitro experiments were performed in human hepatic stellate cells (hHSC) that were purchased from ScienCell Research Laboratories (Carlsbad, Calif.) that were maintained in standard conditions.

Assessment of Liver Morphology, Serum Chemistry, Hepatic Total Bile Acids, Intrahepatic Bile Duct Mass, and Cholangiocyte Proliferation.

Hematoxylin and eosin (H&E) staining was performed in formalin-fixed, paraffin-embedded liver sections (4-5 µm, 3 samples from 3 different animals) to determine liver morphology. H&E stained liver sections were evaluated by a board-certified pathologist to assess the degree of lobular damage, hepatic necrosis and portal inflammation. At least 10 different portal areas were evaluated for each parameter. Liver sections were examined in a coded fashion by BX-51 light microscopy (Olympus, Tokyo, Japan) equipped with a camera (See, Mancinelli, R et al., *Ischemia reperfusion of the hepatic artery induces the functional damage of large bile ducts by changes in the expression of angiogenic factors. Am J Physiol Gastrointest Liver Physiol* 2015;

309:G865-873 (2015); Taffetani S et al., *Prolactin stimulates the proliferation of normal female cholangiocytes by differential regulation of Ca2+-dependent PKC isoforms*, BMC Physiol 7:6 (2007)).

Serum levels of alkaline phosphatase (ALP) and γ-glutamyltransferase (γGT) are commonly used to diagnose PBC (Heathcote, E J, *Management of primary biliary cirrhosis. The American Association for the Study of Liver Diseases practice guidelines*, Hepatology 31:1005-1013 (2000)); therefore, were measured serum levels of ALP and γGT in mouse serum samples using the Alkaline Phosphatase Assay Kit and γ-Glutamyltransferase Activity Colorimetric Assay Kit, respectively (Abcam; Cambridge, Mass.).

Early stage PBC is identified by cholangiocyte proliferation, whereas late stage PBC is characterized by ductopenia. In our mouse samples, intrahepatic bile duct mass (IBDM) and cholangiocyte proliferation were measured in liver sections (4-5 μm, 10 fields analyzed from 3 samples from 3 different animals) by semi-quantitative immunohistochemistry for cytokeratin-19 (CK-19, a cholangiocyte specific marker) and Ki-67, respectively (Kennedy, L L et al., *Knockout of microRNA-21 reduces biliary hyperplasia and liver fibrosis in cholestatic bile duct ligated mice*. Lab Invest 96:1256-1267 (2016); Jones, H et al., *Inhibition of mast cell-secreted histamine decreases biliary proliferation and fibrosis in primary sclerosing cholangitis Mdr2(−/−) mice*, Hepatology 2016; 64:1202-1216 (2016)).

Measurement of Cholangiocyte Apoptosis and Senescence.

Cholangiocyte apoptosis was evaluated by terminal deoxynucleotidyl transferase dUTP nick-end labeling (TUNEL, to identify double-stranded DNA breaks) staining and semi-quantification (Mancinelli, R et al., *GABA induces the differentiation of small into large cholangiocytes by activation of Ca(2+)/CaMK I-dependent adenylyl cyclase 8*. Hepatology 58:251-263 (2013)). Cholangiocyte senescence was measured in our mouse models by: (i) qPCR in isolated cholangiocytes for the senescence markers cyclin-dependent kinase inhibitor 2A (p16), cyclin-dependent kinase inhibitor 4C (p18), cyclin-dependent kinase inhibitor 1 (p21), and C—C motif chemokine ligand 2 (CCL2); (ii) immunofluorescence for CCL2 in OCT-embedded liver sections (8 μm, 10 fields analyzed from 3 samples from 3 different animals) co-stained for CK-19 (to visualize bile ducts); and (iii) staining for senescence-associated beta galactosidase (SA-β-gal) using the Senescence β-Galactosidase Staining Kit (Cell Signaling Technology; Boston, Mass.) (Tabibian, J H et al., *Characterization of cultured cholangiocytes isolated from livers of patients with primary sclerosing cholangitis*, Lab Invest 94:1126-1133 (2014); Tabibian, J H et al., *Cholangiocyte senescence by way of N-ras activation is a characteristic of primary sclerosing cholangitis*, Hepatology 2014; 59:2263-227530-32).

Cholangiocyte Expression of Sct, SR, CFTR and Cl−/HCO3− AE2 and Levels of Sct in Serum, Bile and Cholangiocyte Supernatant.

Expression of Sct, SR, CFTR, and AE2 was evaluated by qPCR in isolated cholangiocytes and by immunofluorescence in OCT-embedded liver sections (8 μm, 10 fields analyzed from 3 samples from 3 different animals) co-stained for CK-19 (to visualize bile ducts) (McDaniel, K et al., *Forkhead box A2 regulates biliary heterogeneity and senescence during cholestatic liver injury in mice double dagger*, Hepatology 2017; 65:544-559 (2017)). To recapitulate these experiments in human samples, expression of Sct, SR, CFTR, and AE2 was determined in liver sections (4-5 μm, 10 fields analyzed from 3 samples from 3 different animals) by immunohistochemistry. Semiquantitative analysis was performed using our published grading system (34): 0%-5%=negative; 6%-10%=+/−; 11%-30%=+; 31%-60%=++; >61%=+++. As well, levels of Sct in serum, bile and cholangiocyte supernatants from mice and/or patients were measured using the Secretin EIA Kit (Phoenix Pharmaceuticals; Burlingame, Calif.) (Glaser, S et al., *Secretin stimulates biliary cell proliferation by regulating expression of microRNA 125b and microRNA let7a in mice*, Gastroenterology 146:1795-1808 e1712 (2014); (Wu, N et al., *The secretin/secretin receptor axis modulates liver fibrosis through changes in transforming growth factor-beta1 biliary secretion in mice*, Hepatology 64:865-879 (2016)).

Measurement of Liver Fibrosis and Hepatic Stellate Cell Activation.

In our mouse models, liver fibrosis was evaluated by: (i) Sirius Red staining and semi-quantification in formalin-fixed, paraffin-embedded liver sections (4-5 μm, 10 fields analyzed from 3 samples from 3 different animals); and (ii) immunohistochemistry for alpha-smooth muscle actin (α-SMA) in formalin-fixed, paraffin-embedded liver sections (4-5 μm, 10 fields analyzed from 3 samples from 3 different animals) (Han, Y et al., *Prolonged exposure of cholestatic rats to complete dark inhibits biliary hyperplasia and liver fibrosis*, Am J Physiol Gastrointest Liver Physiol 2014; 307:G894-904 (2014)).

Hepatic stellate cells (HSCs) are the key contributors to liver fibrosis (36); therefore, we determined the number of activated HSCs in liver sections (8 μm, 10 fields analyzed from 3 samples from 3 different animals) by immunofluorescence for synaptophysin-9 (SYP-9, a marker of activated HSCs (Kennedy, L L et al., *Knockout of microRNA-21 reduces biliary hyperplasia and liver fibrosis in cholestatic bile duct ligated mice*, Lab Invest 2016; 96:1256-1267 (2016)) co-stained for CK-19 (to visualize bile ducts) (Jones, H et al., *Inhibition of mast cell-secreted histamine decreases biliary proliferation and fibrosis in primary sclerosing cholangitis Mdr2(−/−) mice*, Hepatology 2016; 64:1202-1216 (2016)).

To evaluate the role of cholangiocyte-derived factors on hHSC activation, in vitro hHSCs were incubated with in vivo isolated cholangiocyte supernatants (following incubation at 37° C. for 4 hr) from WT mice and dnTGF-βRII mice at 12 wks and 32 wks of age treated with either saline, Sct or SR antagonist. Activation of hHSCs was determined by qPCR for FN-1, TGF-β1, α-SMA, and collagen type-1a (Kennedy, L L et al., *Knockout of microRNA-21 reduces biliary hyperplasia and liver fibrosis in cholestatic bile duct ligated mice*, Lab Invest 96:1256-1267 (2016)).

Statistical Analysis.

Data are expressed as mean±SEM. Differences between groups were analyzed by Student unpaired t test when two groups were analyzed and by two-way ANOVA when more than two groups were analyzed.

Results.

Assessment of Liver Morphology, Serum Chemistry, IBDM and Cholangiocyte Proliferation.

Figure 2:
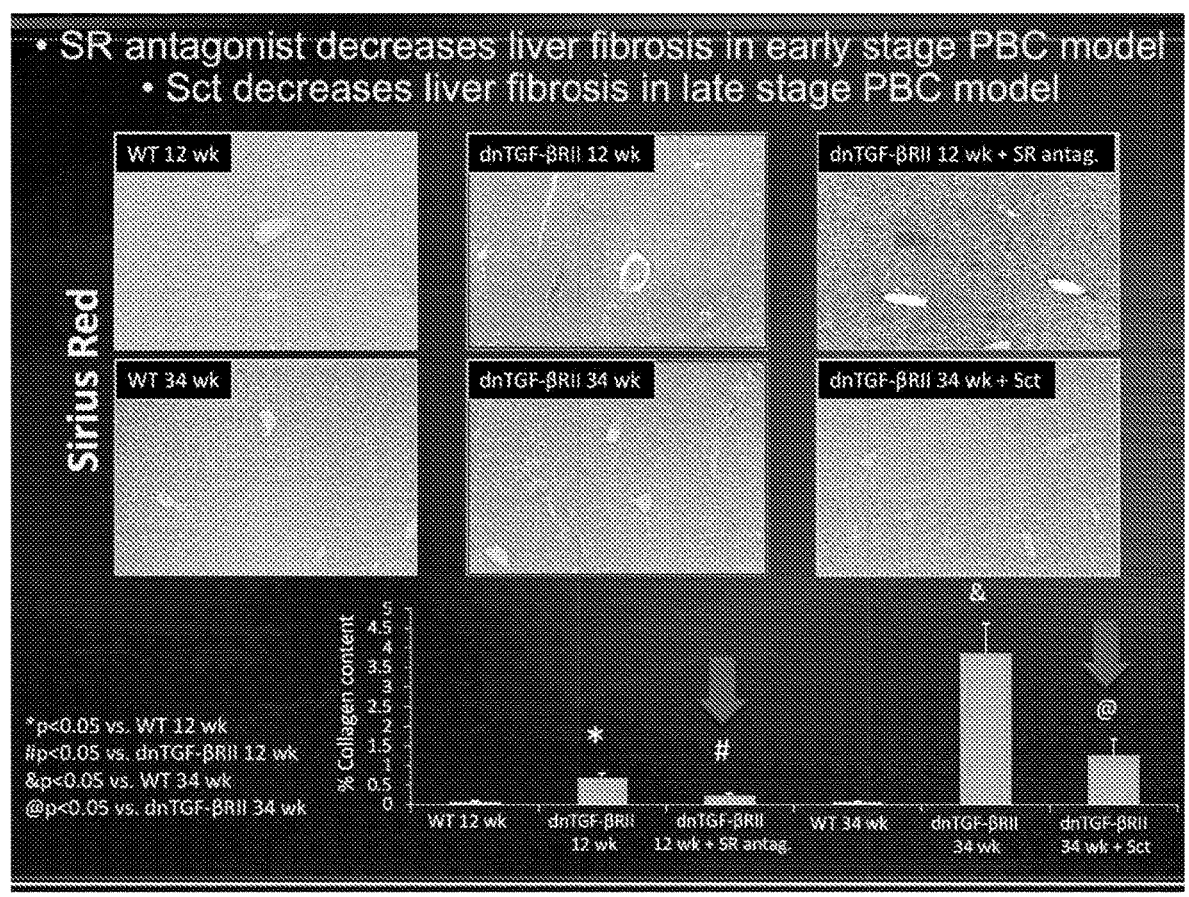
FIG. 2 demonstrates that administration of SR antagonist (SCT 5-27) decreases hepatic fibrosis in early stage PBC mice (dnTGF-βRII 12 week). Administration of secretin inhibits hepatic fibrosis in late stage PBC mice (dnTGF-βRII 34 week). The top panel shows an increase in the amount of Sirius red staining (indication of hepatic fibrosis) in early stage PBC mice around portal areas compared to WT 12 wk mice. Sirius red staining was reduced in early stage PBC mice treated with SR antagonist. There was an increase in Sirius red staining in late stage PBC mice, which was reduced by treatment with SR agonist. Orig. magn., ×40. Bottom histogram illustrates the quantification of the Sirius red staining as a percentage (% collagen content) of liver area. There is a significant increase in collagen content in the early stage PBC mice, which is significantly reduced in the early stage PBC mice treated with SR antagonist. There was a significant increase in collagen content in late stage PBC mice, which is significantly reduced in late stage PBC mice treated with SR agonist. Data are mean±SEM of 3 evaluations from 3 individual mice. $*p<0.05$ vs. WT 12 wk. $\#p<0.05$ vs. dnTGF-βRII 12 wk. $^{\&}p<0.05$ vs WT 34 wk. $^{@}p<0.05$ vs dnTGF-βRII 34 wk.
Figure 3:
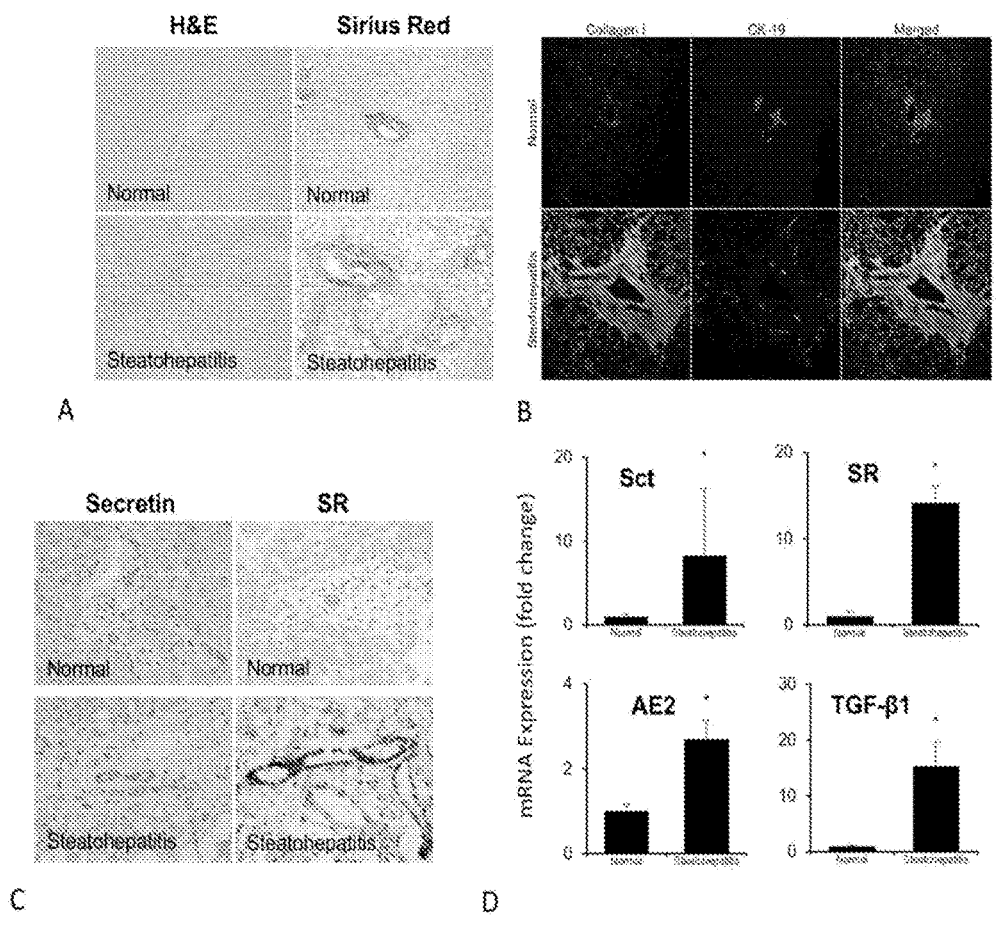
FIG. 3A-D demonstrates that the secretin/secretin receptor axis is upregulated in human patients with steatohepatitis due to alcohol-induced liver injury.

In humans, early stages of PBC (Stage I/II) are characterized by portal and/or periportal hepatitis with bile duct proliferation, and late stages of PBC (Stage III/IV) present with portal and/or periportal hepatitis, bridging fibrosis, bile duct loss and potentially cirrhosis. We evaluated liver architecture in our mouse model of PBC and noticed that 12 wk old dnTGF-βRII mice had portal inflammation, scattered foci of lymphocytic inflammatory infiltration with little lobular necrosis when compared to age-matched WT, which were further increased following treatment with Sct but ameliorated following treatment with the SR antagonist. In the 34 wk old dnTGF-βRII mice, there was portal and lobular inflammation, heavy lymphocytic inflammatory infiltration and lobular necrosis when compared to age-matched WT. Liver damage was ameliorate 34 wk old dnTGF-βRII mice treated with Sct, but exacerbated following SR antagonist treatment (See, FIG. 1 and FIG. 2).

PBC patients present with increased serum levels of ALP and γGT which are used diagnostically, whereas serum aspartate aminotransferase and alanine aminotransferase are only mildly increased and are not used for diagnosis. To identify whether modulation of the Sct/SR axis has an impact on serum levels of ALP and γGT we evaluated these factors in our mouse models. We found that serum levels of ALP and γGT are increased in 12 wk old dnTGF-βRII mice compared to WT, and are even further increased in 34 wk old dnTGF-βRII mice. However, 12 wk old dnTGF-βRII mice treated with Sct had even further increased levels of ALP and γGT compared to saline treated, but levels were reduced following SR antagonist treatment compared to saline treated (data not shown).

During the progression of PBC, early stage patients tend to have increased ductular reaction, whereas late stage patients present with small duct obliteration. Therefore, we analyzed IBDM and biliary proliferation within our models. As identified by immunohistochemical staining for CK-19 (cholangiocyte-specific marker), we noted that dnTGF-βRII mice at 12 wks of age had increased IBDM, but this was significantly reduced at 34 wks of age. Furthermore, dnTGF-βRII mice at 12 wks of age that were treated with Sct had a further increase in IBDM when compared to saline treated mice, but treatment with SR antagonist reduced IBDM compared to saline treated mice. Comparatively, dnTGF-βRII mice at 32 wks of age treated with Sct showed increased IBDM compared to saline treated, and conversely treatment with SR antagonist lead to decreased IBDM compared to saline treated mice (data not shown). Similar trends were noted in biliary proliferation as determined by Ki-67 immunohistochemistry and semi-quantitative analysis (data not shown).

These results demonstrate that: (i) dnTGF-βRII mice at 12 wks of age model characteristics associated with early stage PBC, but dnTGF-βRII mice at 32 wks of age mimic characteristics of late stage PBC and (ii) differential Sct/SR signaling at these different time points influences IBDM and biliary proliferation. These findings highlight the role of the Sct/SR axis in biliary response during PBC progression.

Cholangiocyte Expression of Sct, SR, CFTR and AE2 and Levels of Sct in Serum, Bile and Cholangiocyte Supernatant.

AE2 participates in Sct-stimulated biliary bicarbonate secretion and maintenance of biliary homeostasis, and previously it has been shown that AE2 biliary expression is decreased in late stage PBC patients. However, biliary expression of the Sct/SR axis and subsequent activation of CFTR and AE2 in early and late stage PBC is currently unknown. As identified by immunohistochemical staining it was noted that dnTGF-βRII mice at 12 wks of age had increased Sct, SR, CFTR, and AE2, but the expression of these markers was significantly reduced at 34 wks of age. Furthermore, dnTGF-βRII mice at 12 wks of age that were treated with Sct had a further increase in Sct, SR, CFTR, and AE2 expression when compared to saline treated mice, but treatment with SR antagonist reduced these factors when compared to saline treated mice. Comparatively, dnTGF-βRII mice at 32 wks of age that were treated with Sct showed increased expression of the aforementioned factors when compared to saline treated, and conversely treatment with SR antagonist lead to a further decrease in these factors when compared to saline treated mice (data not shown). Similar findings were noted in Sct secretion as demonstrated by serum Sct levels (data not shown). As well, in liver sections from early stage PBC patients we saw enhanced expression of Sct, SR, CFTR, and AE2 when compared to control livers, but the expression of these factors was reduced in late stage PBC when compared to early stage (data not shown). Similar findings were noted for Sct, SR, CFTR, and AE2 expression in total liver and for serum Sct levels in early and late stage PBC patients (data not shown). These findings are the first to demonstrate that the Sct/SR axis is differentially regulated between early and late stage PBC, and manipulation of this axis may regulate biliary homeostasis during PBC progression.

Measurement of Cholangiocyte Apoptosis and Senescence.

It has been demonstrated that PBC patients present with increased cholangiocyte apoptosis that may contribute to the subsequent damage and hepatic inflammation. By TUNEL staining, we noted that dnTGF-βRII mice at 12 wks of age had decreased TUNEL-positive cholangiocytes compared to WT mice; however, this was further reduced following treatment with Sct, but increased following treatment with the SR antagonist. In dnTGF-βRII mice at 32 wks of age the percentage of TUNEL-positive cholangiocytes significantly increased compared to 12 wk old mice; however, treatment with Sct reduced apoptosis, but treatment with the SR antagonist exacerbated it (data not shown). These findings support the concept that the Sct/SR axis modulates biliary proliferation/apoptosis during the progression of PBC.

Aside from apoptosis, the role of cholangiocyte senescence during PBC is becoming more recognized. It has been noted that patients with PBC have increased cellular senescence during the course of disease, which may lead to progressive bile duct loss. As demonstrated by qPCR, cholangiocytes isolated from 12 wk old dnTGF-βRII mice had increased expression of senescence markers p16, p18, p21, and CCL2, which were further enhanced in 32 wk old dnTGF-βRII mice. However, 12 wk old dnTGF-βRII mice treated with Sct had a further increased senescence, whereas treatment with the SR antagonist decreased the expression of these markers. Conversely, 32 wk old dnTGF-βRII mice treated with Sct had reduced expression of these senescence markers, whereas treatment with the SR antagonist increased the levels of these markers (data not shown). Similar trends were noted in the immunofluorescence for CCL2 and in the staining for SA-β-gal (data not shown). Based on these findings it is evident that the Sct/SR axis regulates biliary senescence during PBC.

Measurement of Liver Fibrosis and HSC Activation.

Previously, it has been shown that early stage PBC is characterized by extensive fibrosis, which is further exacerbated in late stage PBC resulting in bridging fibrosis; therefore, we analyzed hepatic fibrosis in our mice. As indicated by Sirius Red staining and semi-quantification, dnTGF-βRII mice at 12 wks of age have increased collagen deposition, which is further enhanced following Sct treatment but is ameliorated with SR antagonist treatment. Collagen deposition is further enhanced in dnTGF-βRII at 32 wks of age when compared to 12 wks of age; however, this is decreased with Sct treatment but further increased with SR antagonist treatment (data not shown). A similar trend was noted for α-SMA expression (data not shown). It is evident that changes in biliary function, dependent on Sct or SR antagonist treatment, influence hepatic fibrosis during PBC progression.

HSCs are the primary contributors of collagen in the liver during fibrosis and have been shown to be activated during human PBC progression; therefore, we analyzed the degree of HSC activation in our animals. By immunofluorescent staining for SYP-9 (marker of activated HSCs) we determined that HSC activation was increased in dnTGF-βRII mice at 12 wks of age and 34 wks of age. However, dnTGF-βRII mice at 12 wks of age that were treated with Sct showed even further enhanced SYP-9 staining, but this was reduced in 12 wk old mice treated with the SR antagonist. Oppositely, dnTGF-βRII at 34 wks of age that were treated with Sct had reduced SYP-9 expression, but this was enhanced in the 34 wk old mice that were treated with the SR antagonist (data not shown). These findings suggest that changes in HSC activation contribute to the changes noted in hepatic fibrosis following treatment with Sct or the SR antagonist.

We next evaluated the effect of biliary-derived factors on HSC activation. In vitro, hHSCs were incubated with supernatants from cholangiocytes isolated from WT mice and dnTGF-βRII mice at 12 wks and 32 wks of age treated with either saline, Sct or SR antagonist. There was increased expression of FN-1, TGF-β1, α-SMA, and collagen type-1a in hHSCs treated with cholangiocyte supernatants from dnTGF-βRII mice at 12 wks of age and 34 wks of age when compared to age matched controls. However, hHSCs treated with cholangiocyte supernatants from dnTGF-βRII mice at 12 wks of age treated with Sct showed even further enhanced expression of these markers, but expression was reduced in 12 wk old mice treated with the SR antagonist. Furthermore, hHSCs treated with cholangiocyte supernatants from dnTGF-βRII at 34 wks of age treated with Sct had reduced expression of these markers, but expression was enhanced in the 34 wk old mice that were treated with the SR antagonist (data not shown). These data imply that the Sct/SR axis regulates the secretion of biliary factors that can influence HSC activation during PBC.

In summary, liver damage increased in dnTGFβRII mice but was reduced by Sct. IBDM and biliary growth were increased in dnTGFβRII mice at 12 wk but reduced at 34 wk indicating ductopenia. Sct treatment to dnTGFβRII 34 wk increased these parameters. Biliary apoptosis was reduced in dnTGFβRII 12 wk, increased at 34 wk but reduced by Sct. Biliary senescence was increased in dnTGFβRII 12 wk, further increased at 34 wk but reduced by Sct. Liver inflammation, Kupffer cell number, liver fibrosis and HSC activation were increased in dnTGFβRII 12 and 34 wk and reduced by Sct. TBA levels increased in dnTGFβRII 12 wk, further increased at 34 wk but were reduced by Sct. Serum Sct levels were increased in dnTGFβRII 12 wk and human early PBC, but were decreased at 34 wk and advanced PBC. Sct treatment increased serum Sct levels in dnTGFβRII 34 wk. Sct, SR, CFTR and AE2 expression increased in dnTGFβRII 12 wk and human early PBC, but decreased in dnTGFβRII 34 wk and advanced PBC, showing loss of biliary function. Sct treatment increased these parameters in dnTGFβRII 34 wk.

Hepatic damage was increased in dnTGFβRII 12 wk, but reduced following SCT 5-27 treatment. Hepatic damage was further increased dnTGFβRII 34 wk, but was exacerbated by SCT 5-27 treatment. IBDM and cholangiocyte proliferation were increased in dnTGFβRII 12 wk but reduced by SCT 5-27 treatment. dnTGFβRII 34 wk had reduced IBDM and biliary proliferation, indicating ductopenia that was further reduced by SCT 5-27 treatment. Conversely, cholangiocyte apoptosis was reduced in dnTGFβRII 12 wk that was enhanced by SCT 5-27 treatment. dnTGFβRII 34 wk had increased biliary apoptosis that was further increased following SCT 5-27 treatment. Biliary senescence was increased in dnTGFβRII 12 wk but reduced following SCT 5-27 treatment. Biliary senescence was increased in dnTGFβRII 34 wk and further increased following SCT 5-27 treatment. Hepatic fibrosis and HSC activation were increased in dnTGFβRII 12 wk and 34 wk which was reduced following SCT 5-27 treatment at 12 wk; however, SCT 5-27 treatment at 34 wk increased these parameters. Conversely, HSC senescence was reduced in dnTGFβRII 12 wk and 34 wk, but was increased at 12 wk following SCT 5-27 treatment. Serum and bile secretin levels were increased in both dnTGFβRII 12 wk and human early PBC; however, this was decreased at 34 wk and in advanced PBC. Treatment with SCT 5-27 reduced secretin levels in dnTGFβRII 12 wk and 34 wk.

Discussion.

In our study, we found that the Sct/SR axis is a key regulator of liver damage, biliary proliferation, HSC activation and liver fibrosis during PBC progression. In dnTGF-βRII mice at 12 wks of age (model of early stage PBC) there was increased Sct/SR signaling alongside enhanced liver damage, ductular reaction, mild fibrosis, and increased HSC activation. Administration of an SR antagonist to dnTGF-βRII mice at 12 wks of age reduced Sct/SR signaling, leading to a reduction in liver damage. However, treatment with Sct increased Sct/SR signaling, thereby exacerbating these parameters. In dnTGF-βRII mice at 34 wks of age (model of late stage PBC) there was reduced Sct/SR signaling, which was accompanied by increased liver damage, bile duct loss, bridging fibrosis, and increased HSC activation. Opposite of our early stage PBC model, we found that administration of Sct restored Sct/SR signaling in dnTGF-βRII mice at 34 wks of age leading to amelioration of liver damage; however, treatment with an SR antagonist further reduced the Sct/SR signaling axis which exacerbated liver damage. In human samples, there was increased Sct, SR, CFTR, and AE2 expression and Sct serum and bile levels in human early stage PBC patients, but all of these factors were greatly reduced in human late stage PBC patients. These findings elude to the role of Sct/SR signaling during PBC progression.

In humans, early stages of PBC (Stage I/II) are characterized by portal and/or periportal hepatitis with bile duct proliferation, and late stages of PBC (Stage III/IV) present with portal and/or periportal hepatitis, bridging fibrosis, bile duct loss and potentially cirrhosis. The early stage PBC mouse model had liver damage which closely mimicked human early stage PBC, while the late stage PBC mouse model more closely represented human late stage PBC. However, treatment with an SR antagonist reduced liver damage in the early stage PBC mouse model, while treatment with Sct decreased liver damage in the late stage PBC mouse model. These findings indicate that increased Sct/SR signaling during early stage PBC, but reduced signaling during late stage PBC, may drive liver damage associated with this disease. ALP and γGT have been shown to be upregulated in the serum of PBC patients and are markers of liver disease. When analyzing serum ALP and γGT levels we found that the expression of these markers was increased in both the early stage and late stage PBC models. Similar to the above data, we found that administration of an SR antagonist to the early stage PBC mouse model, and treatment with Sct in the late stage PBC model, reduced the serum levels of both of these markers. This data further confirms that modulation of the Sct/SR axis during early and late stage PBC may ameliorate liver damage associated with this disease.

Dysregulation in the balance of biliary growth/loss is noted in multiple cholangiopathies, including PBC. Early stage PBC patients show increased ductular reaction, whereas late stage PBC patients are characterized by small duct obliteration. Our mouse model of early stage PBC showed ductular reaction, which was reduced by SR antagonist treatment but increased by treatment with Sct. Conversely, our mouse model of late stage PBC showed bile duct loss, which was recovered by Sct treatment but even further reduced by SR antagonist treatment. Previous work from our group has shown that Sct treatment stimulates biliary cell proliferation, whereas knockout of SR reduces BDL-induced biliary cell proliferation. During early stage PBC, increased Sct signaling may contribute to ductular reaction through increased PKA activity and ERK1/2 phosphorylation, whereas loss of Sct signaling during late stage PBC leads to bile duct loss through downregulation of these mechanisms. Further work analyzing downstream mechanisms is necessary to fully identify the pathway by which changes in biliary growth/loss are regulated during PBC progression.

Sct/SR signaling is largely known for maintaining biliary homeostasis, as well as stimulating secretion of bicarbonate via cyclic cAMP-mediated opening of CFTR and activation of AE2. Previously, it was shown that PBC patients have reduced AE2 expression, indicating a role for the bicarbonate umbrella during PBC (Hisamoto, S et al., Hydrophobic bile acids suppress expression of AE2 in biliary epithelial cells and induce bile duct inflammation in primary biliary cholangitis, J Autoimmun 75:150-160 (2016)). However, discretion in expression/activation of the bicarbonate umbrella during early versus late stage PBC have yet to be elucidated. The early stage PBC mouse model had increased Sct, SR, CFTR, and AE2 expression, as well as increased Sct secretion in bile and serum. Administration of SR antagonist to the early stage PBC mouse model reduced all of these parameters, but treatment with Sct further increased them. Conversely, the late stage PBC mouse model had decreased Sct, SR, CFTR, and AE2 expression, as well as reduced Sct secretion in bile and serum. In the late stage PBC mouse model, treatment with Sct increased all of these parameters, but treatment with SR antagonist further decreased them. Similar to our mouse findings, human early stage PBC patients showed enhanced expression of Sct, SR, CFTR, and AE2, alongside increased Sct levels in serum and bile; however, human late stage PBC patients had a reduction in all of these parameters. This overactivation of the Sct/SR axis during early stage PBC contributes to enhanced biliary proliferation, which in turn leads to increased hepatic damage and subsequent liver damage. During late stage PBC, loss of the Sct/SR axis leads to reduced CFTR opening and AE2 activation, subsequently decreasing bicarbonate secretion (14-17). This decreased bicarbonate secretion may make cholangiocytes more susceptible to damage through loss of the hepatoprotective bicarbonate umbrella (Hohenester, S et al., Biliary bicarbonate secretion constitutes a protective mechanism against bile acid-induced injury in man, Dig Dis 29:62-65 (2011); Hohenester, S et al., A biliary HCO3-umbrella constitutes a protective mechanism against bile acid-induced injury in human cholangiocytes, Hepatology 55:173-183 (2012)).

It is largely known that late stage PBC patients have increased biliary apoptosis when compared to controls, and this may contribute to bile duct loss during advanced disease. When looking at in the mouse model, we found decreased biliary apoptosis in the early stage PBC mouse model, which is typical during ductular reaction. Biliary apoptosis was increased in the early stage PBC model following SR antagonist treatment, but further decreased following Sct administration. However, our late stage PBC model showed a large increase in biliary apoptosis, which was decreased following Sct treatment but increased following treatment with an SR antagonist. Previously, it has been shown that knockout of SR is associated with increased biliary apoptosis. Therefore, during early stage PBC, increased Sct/SR signaling reduces biliary apoptosis, whereas loss of Sct/SR signaling during late stage PBC increases biliary apoptosis. This imbalance of Sct/SR signaling contributes to the changes in biliary apoptosis noted in early and late stage PBC.

Cellular senescence is an irreversible growth arrest that is associated with telomere shortening and DNA damage. (See, Campisi, J et al., Cellular senescence: when bad things happen to good cells, Nat Rev Mol Cell Biol 8:729-740 (2007)). As well, senescent cells can enter a SASP phenotype and begin to secrete various cytokines, chemokines and growth factors. Increased biliary senescence and SASP has been shown in patients with PBC and has been suggested to be the mechanism driving bile duct loss. Regardless of mechanism, the early stage PBC mouse model had increased biliary senescence, which was reduced following SR antagonist treatment. However, the early stage PBC mouse model treated with Sct had increased biliary senescence. The late stage PBC mouse model demonstrated a further increase in biliary senescence, which was reduced by Sct treatment but increased by SR antagonist treatment. Specifically, increased biliary expression of p21 has been shown in patients with PBC and correlates with progressive bile duct loss. (See, Sasaki, M et al., Activation of ATM signaling pathway is involved in oxidative stress-induced expression of mito-inhibitory p21WAF1/Cip1 in chronic non-suppurative destructive cholangitis in primary biliary cirrhosis: an immunohistochemical study, J Autoimmun 31:73-78 (2008)). As well, upregulation of CCL2 in cholangiocytes has been noted in PBC patients; this upregulation of CCL2 in cholangiocytes is indicative of SASP and may promote the infiltration of inflammatory cells. (See, Sasaki, M et al., Chemokine-chemokine receptor CCL2-CCR2 and CX3CL1-CX3CR1 axis may play a role in the aggravated inflammation in primary biliary cirrhosis, Dig Dis Sci 59:358-364 (2014)). Based on our findings, manipulation of the Sct/SR axis contributes to biliary senescence during early and late stage PBC.

Early stage PBC is characterized by extensive fibrosis, which can progress to bridging fibrosis during is late stage PBC. Increased hepatic fibrosis and HSC activation was noted in our early stage PBC mouse model, which were reduced following treatment with an SR antagonist. Oppositely, the early stage PBC mouse model treated with Sct showed increased hepatic fibrosis and HSC activation. A previous publication from our group found that loss of Sct/SR signaling reduced hepatic fibrosis via reduced TGFβ1 signaling, which may be the same mechanism through which hepatic fibrosis is reduced in our early stage PBC mouse model treated with the SR antagonist. The late stage PBC mouse model presented with bridging fibrosis and increased HSC activation, which were ameliorated by treatment with Sct; however, treatment with SR antagonist increased both of these parameters in the late stage PBC mouse model. Considering that increased Sct/SR signaling is associated with increased fibrosis via TGFβ1 signaling, it was interesting to note that increasing Sct levels reduced fibrosis in the late stage PBC model. While the claimed invention is not dependent on a particular mechanism, in other models of cholestasis, there is a positive correlation between increased biliary senescence and increased hepatic fibrosis/HSC activation; therefore, we postulate that restoration of the Sct/SR signaling pathway during the model of late stage PBC reduces biliary senescence which in turn decreases hepatic fibrosis.

The discovery of a differential expression of Sct/SR signaling during early and late stage PBC is novel and can be a diagnostic and/or therapeutic tool for this disease. Considering that SR is only expressed by large cholangiocytes in the liver, and late stage PBC primarily affects small cholangiocytes, further work is necessary to evaluate how Sct/SR signaling in large cholangiocytes affects small cholangiocyte function. Our data identify that the Sct/SR pathway regulates biliary senescence, and it may be that manipulation of this pathway decreases senescence/SASP in PBC to decrease small cholangiocyte damage. As well, cholangiocytes have been shown to act as antigen presenting cells to prime the cholangiocyte as a target for immune-mediated injury (Barnes, B H et al., *Cholangiocytes as immune modulators in rotavirus-induced murine biliary atresia*, Liver Int 29:1253-1261 (2009)). Therefore, the Sct/SR axis can play a role in large cholangiocyte immunomodulatory activity, which in turn affects the surrounding inflammatory environment.

Example 2. The Secretin/Secretin Receptor Axis Modulates Ductular Reaction and Liver Fibrosis Through Changes in TGF-β1-Mediated Biliary Senescence Materials and Methods.

Reagents were purchased from Sigma-Aldrich Co. (St. Louis, Mo.) unless otherwise indicated. The RNeasy Mini Kits for RNA isolation and mouse PCR primers were purchased from Qiagen (Valencia, Calif.). The antibody for cytokeratin-19 (CK-19) was purchased from Abcam (Cambridge, Mass.). The polyclonal antibody against cystic fibrosis transmembrane regulator (CFTR) was purchased from Cell Signaling Technology (Danvers, Mass.). The polyclonal antibody against chloride bicarbonate anion exchanger 2 (AE2) was purchased from LifeSpan Biosciences, Inc. (Seattle, Wash.). The antibodies against phospho-SMAD2/3 (small mothers of decapentaplegic 2 and 3) were purchased from Cell Signaling Technology. Enzyme-linked immunosorbance assay (ELISA) kits to measure TGF-β1 levels in serum and biliary supernatants were obtained from Affymetrix Inc. (Santa Clara, Calif.).

We used the following mouse primers: proliferating cell nuclear antigen (PCNA, NM_011045); Ki 67 (NM_001081117); transforming growth factor-β1 (TGF-β1, NM_011577); transforming growth factor-β1 receptor (TGF-β1R, NM_009370); α-smooth muscle actin (α-SMA, NM_007392); fibronectin-1 (Fn-1, NM_010233); collagen, type I, alpha (Col1a1 NM_007742); p16 (NM_009877); CCL2 (NM_011333); p21 (NM_007669); and glyceraldehyde-3-phosphate dehydrogenase (GAPDH, NM_008084). For real-time PCR analysis in human hepatic stellate cell lines (HHSteCs) we used the following primers: TGF-β1 (NM_000660), TGF-β1R (NM_004612); α-SMA (NM_001613); Fn-1 (NM_212482); Col1a1 (NM_000088); p16 (NM_000077); CCL2 (NM_002982); p21 (NM_078467); and GAPDH (NM_078467).

Animal Models.

The animal experiments were performed according to protocols approved by the Baylor Scott & White IACUC Committee. C57/BL6 wild-type (WT) mice (25-30 gm) were purchased from Charles River (Wilmington, Mass.). Male mice were used in these studies. Both the $Sct^{-/-}$ and $SR^{-/-}$ mouse colonies are established in our animal facility. The established mouse strains, $Sct^{-/-}$ and $SR^{-/-}$, were bred together until the homozygous double knockout ($Sct^{-/-}/SR^{-/-}$) mice were obtained after several five generations. The genotype of each $Sct^{-/-}/SR^{-/-}$ mouse was confirmed by PCR amplification of genomic DNA extracted from the tail. Genotyping was performed by Charles River Laboratories. The $Sct^{-/-}$ genotype was identified using three primers: Sct-WT-Forward: 5'-GAGTGCCACCTTGCCCTG-3'// (SEQ ID NO:4), Sct-KO-Forward: 5'-GATTT-GAGTTTCGGTGCTGG-3'//(SEQ ID NO:5), Sct-COM-Reverse: 5'-GGTTTGGGGAGCCAGTATCT-3'//(SEQ ID NO:6), with migration positions for WT at 508 bp and Sct at 743 bp, respectively. The sequence of primers for identification of $SR^{-/-}$ SR-WTForward: 5'-CAAGCCTGCATT-CATCAAGA-3'//(SEQ ID NO:7), Sct-KO-Forward: 5'-GCCAGAGGCCACTTGTGTAG-3'//(SEQ ID NO:8), Sct-COM-R: 5'-TCATACTCAGGCCCAGTTCC-3'//(SEQ ID NO:9), with migration positions for WT at 536 bp and $SR^{-/-}$ at 240 bp, respectively. Animals were maintained in a temperature-controlled environment (20-22° C.) with 12:12-h light/dark cycles and fed ad libitum standard chow with free access to drinking water. The experiments were performed in normal (sham) and BDL (1 week) WT and $Sct^{-/-}$, $SR^{-/-}$ and $Sct/SR^{-/-}$ mice. Before each procedure, animals were treated with euthasol (200-250 mg/kg BW). In all groups, we measured liver and body weight and liver to body weight ratio (index of liver cell growth).

Purified Cholangiocytes and S Cells and Laser Capture Microdissection (LCM)-Isolated HSCs.

Cholangiocytes were obtained by immunoaffinity separation as described herein above, using a monoclonal antibody (a gift from Dr. R. Faris, Brown University, Providence, R.I.) that is expressed by all intrahepatic cholangiocytes. HSCs from the selected groups of mice were isolated by LCM as described previously in Wu, N et al., *The secretin/secretin receptor axis modulates liver fibrosis through changes in transforming growth factor-beta1 biliary secretion in mice*, Hepatology (Baltimore, Md.) 64(3):865-879 (2016). Briefly, frozen liver sections (n=3, 10 μm thick) were incubated overnight with an anti-desmin (a marker of stellate cells) antibody. Then, desmin-positive cells were dissected from the slides using a LCM system Leica LMD7000 (Buffalo Grove, Ill.) and were collected before RNA extraction with the Arcturus PicoPure RNA isolation kit (Thermo Fisher Scientific CO, Mountain View, Calif.). The in vitro studies were performed in: (I) immortalized murine cholangiocyte lines derived from large cholangiocytes lining large ducts (IMCLs); and (ii) human hepatic stellate cell lines (HHSteCs; ScienCell Research Laboratories, Carlsbad, Calif.).

Measurement of Secretin Levels in Serum and Supernatant of Cholangiocytes and S Cells.

To validate our models, we measured by semiquantitative immunohistochemistry the immunoreactivity of Sct and SR in paraffin-embedded liver sections (4-5 μm thick, 10 different fields analyzed from 3 samples from 3 different animals); sections were examined with a Leica Microsystems DM 4500 B Microscopy (Weltzlar, Germany) equipped with a JenoptikProg Res C10 Plus Videocam (Jena, Germany). Observations were processed with an Image Analysis System (IAS; Delta Sistemi, Rome, Italy) in a blinded fashion. We also evaluated secretin levels in serum as well as in short-term (6 hr) cultures of isolated cholangiocytes and S cells (1×10⁷) from the selected groups of animals by enzyme immunoassay (ELISA) kits (Phoenix Pharmaceuticals, Inc., Burlingame, Calif.).

Immunoreactivity for Sct and SR in Liver Sections and Measurement of Secretin Levels in Serum and Bile and Bicarbonate Levels in Bile The immunoreactivity of Sct and SR was measured by immunohistochemistry in liver sections incubated overnight at 4° C. with the selected primary antibody; Following washes in 1× phosphate buffered saline (PBS), sections were incubated for 20 min with a secondary biotinylated antibody (Dako Cytomation LSAB Plus System-HRP, Glostrup, Denmark), then with Dako ABC for 20 min and developed with 3-3'-diaminobenzidine (Dako Cytomation Liquid DAB Plus Substrate Chromogen System). All immunohistochemical reactions include antigen unmasking, blocking endogenous peroxidase activity and avidin/biotin blocking; appropriate negative controls were included. Sections were examined with a Leica Microsystems DM 4500 B Microscopy (Weltzlar, Germany) equipped with a JenoptikProg Res C10 Plus Videocam (Jena, Germany). Observations were processed with an Image Analysis System (IAS; Delta Sistemi, Rome, Italy) in a blinded fashion by a board-certified pathologist. Secretin levels in serum and bile were measured by ELISA kits (Phoenix Pharmaceuticals, Inc., Burlingame, Calif.) Intrahepatic Bile Duct Mass. Bile was collected from sham or BDL mice as described 26. Bile bicarbonate levels were measured by the National Mouse Metabolic Phenotyping Centers (Yale University School of Medicine, New Haven, Conn.).

Evaluation of Liver Histology and Serum Chemistry (IBDM), Immunoreactivity for CFTR and AE2 and Liver Fibrosis in Liver Sections.

Measurement of TGF-$\beta$1 Levels in Serum and Biliary Supernatant.

The architecture of liver, stomach, small and large intestine, pancreas, lung, spleen and kidney was evaluated in paraffin-embedded sections (4-5 µm) by hematoxylin and eosin (H&E) staining. Slides were evaluated in a blinded fashion by a board-certified pathologist (ABS, Baylor Scott & White health Care).

Ductular reaction was evaluated in frozen liver sections (4-5 µm thick, 10 fields evaluated from 3 samples from 3 animals) as the area occupied by CK-19 positive-bile ducts/ total area×100. Sections were examined with a Leica Microsystems DM 4500 B Microscopy (Weltzlar, Germany). The immunoreactivity of CFTR and AE2 (functional markers of biliary growth) whose expression is enhanced following cholangiocyte hyperplasia but decreased during biliary damage/loss was evaluated in paraffin-embedded liver sections (4-5 µm thick, 10 fields were evaluated from 3 samples from 3 animals). A negative score was assigned when 0-5% of bile ducts were positive for Sct, SR, CFTR or AE2; a +/− score was assigned when 6-10% of bile ducts were positive; a + score was assigned when 11-30% of bile ducts were positive; a ++ score was assigned with 31-60% of intrahepatic bile ducts positive; and a score +++ was assigned when more than 61% of bile ducts were positive. The evaluations were performed independently by a board-certified pathologist in a blinded fashion (EG, Sapienza, Rome, Italy).

Hepatic fibrosis was evaluated by Sirius Red staining in paraffin-embedded liver sections (4-5 µm thick, 10 fields analyzed from 3 samples from 3 animals) and immunofluorescence for Col1a1 (co-stained with CK-19) in frozen liver sections (8 µm thick, 10 fields analyzed from 3 samples from 3 animals). Liver sections stained with Sirius Red were evaluated with a Leica Microsystems DM 4500 B Microscopy (Weltzlar, Germany) equipped with a JenoptikProg Res C10 Plus Videocam (Jena, Germany). Immunofluorescent staining was visualized using Leica AF 6000 Modular Systems (Leica Biosystems Newcastle Ltd.). Liver fibrosis was measured in total liver samples by the Hydroxyproline Assay Kit (MAK008; Sigma-Aldrich). The mRNA expression of TGF-$\beta$1, TGF-$\beta$1R, Col1a1, $\alpha$-SMA and Fn1 was measured by real-time PCR in total liver as well as isolated cholangiocytes and HSCs. The levels of TGF-$\beta$1 were measured by ELISA kits in serum and short-term (6-hour) cultures of isolated cholangiocytes.

Cellular senescence was assessed in frozen liver sections (10 µm thick) by staining for SA-$\beta$-galactosidase (SA-$\beta$-gal) by commercially available kits (MilliporeSigma, Billerica, Mass.). Observations were performed in a blinded fashion. We also performed double immunofluorescence for p16 co-stained with CK-19 was performed in frozen serial liver sections (10 µm thick); 10 fields were analyzed from 3 different liver samples from 3 animals. We also measured cellular senescence by real-time PCR for p16 and p21 in cholangiocytes and HSCs.

Measurement of TGF-$\beta$1 Levels and Fibrosis and Cellular Senescence in WT Mice and Large IMCLs Treated with Secretin.

WT mice were treated for 1 wk with saline or secretin (Sct; 2.5 nmoles/kg body weight per day) before collecting cholangiocytes, HSCs and cholangiocyte supernatants. The levels of TGF-$\beta$1 were measured in short-term (6-hour) cultures of cholangiocytes by ELISA kits. Subsequently, we measured: (i) liver fibrosis by immunofluorescence for Col1a1 in liver sections and real-time PCR for TGF-$\beta$1, TFG-$\beta$1R, Col1a1, $\alpha$-SMA and Fn1 in cholangiocytes and HSCs; and (ii) cellular senescence by immunofluorescence in liver sections for p16 and real-time PCR for p16 and p21 in cholangiocytes and HSC. To determine if secretin affects cholangiocyte senescence through the autocrine release of TGF-$\beta$1, large IMCLs were treated with secretin (10 nM) for 12 hr in the absence/presence of LY2109761, a small-molecule inhibitor selectively targeting both TGF-$\beta$ receptor type I and II with Ki of 38 nM and 300 nM, respectively (10 nM, Cayman Chemical Company, Ann Arbor, Mich.) before measuring the expression of fibrosis and/or senescence genes by real-time PCR.

Paracrine Effect of Secretin-Stimulated Biliary TGF-☐1 on the Expression of Fibrosis and Senescence Genes in HHSteCs.

We performed experiments to demonstrate that biliary TGF-$\beta$1 levels (modulated by the Sct/SR axis) alter fibrosis and cellular senescence of HHSteCs by a paracrine mechanism. Biliary supernatants were obtained from normal and BDL WT mice and Sct$^{-/-}$, SR$^{-/-}$ and Sct$^{-/-}$/SR$^{-/-}$ BDL mice as well as normal WT mice treated with saline or secretin. HHSteCs were incubated with the aforementioned biliary supernatants (containing different levels of TGF-$\beta$1) for 24 hr (in the absence or presence of LY2109761) before measuring the expression of senescence and fibrosis genes by real-time PCR. Furthermore, HHSteCs were incubated with the supernatant of large IMCLs treated for 0.2% bovine serum albumin (basal) or secretin (10 nM) with/without LY2109761 for 6 hr before measuring the mRNA expression of fibrosis and senescence genes. To provide direct evidence that TGF-$\beta$1 directly modulates fibrosis and senescence of IMCLs and HHSteCs, these cells were stimulated with TGF-β1 (10 nM) for 24 hr before measuring the expression of PCNA as well as fibrosis and senescence genes by real-time PCR.

The goal of the experiments in IMCLs was to demonstrate that the effects of the Sct/SRTGF-β1 axis on cellular senescence are mediated by a direct interact with cholangiocytes rather that in vivo non-specific effects. HHSteCs are suitable for our in vitro study to provide direct evidence for changes in fibrogenic activity and cellular senescence after incubation with the selected cholangiocyte supernatant.

Expression of the Sct-Dependent microRNA 125b/VEGF-A Axis.

To begin to determine the signaling mechanisms by which the Sct/SR axis modulates liver fibrosis by a paracrine mechanism through changes in TGF-β1-mediated biliary senescence, we evaluated the expression of the miRNA125b/VEGF-A axis, that is a key signaling pathway in secretin induction of ductular reaction. This was accomplished by measuring the: (i) expression miRNA125b and VEGF-A by real-time PCR analysis in isolated cholangiocytes; and (ii) immunoreactivity of VEGF-A in liver sections from the selected groups of animals.

Statistical Analysis.

Data are expressed as mean±SEM. Differences between groups were analyzed by Student's unpaired t-test when two groups were analyzed and ANOVA when more than two groups were analyzed, followed by an appropriate post hoc test.

Results

Immunoreactivity of Sct and SR in Liver Sections and Secretin Serum and Bile Levels.

The immunoreactivity of Sct and SR was higher in liver sections from BDL WT compared to WT mice but was absent in their respective knock-out mice (data not shown). Secretin levels were higher in both serum and bile from BDL compared to WT mice but decreased significantly to background levels in both serum and bile from $Sct^{-/-}$, $SR^{-/-}$ and $Sct^{-/-}/SR^{-/-}$ BDL mice compared to BDL WT mice. The background Sct levels in serum and bile (observed in $Sct^{-/-}$ and $Sct^{-/-}/SR^{-/-}$ mice) is likely due to cross-reactivity of the antibodies present in the ELISA kit with other peptides.

Evaluation of Liver Histology and Serum Chemistry, IBDM, Immunoreactivity for CFTR and AE2 and Liver Fibrosis in Liver Sections.

Liver Sections.

Liver to body weight ratio increased in BDL WT compared to normal mice but decreased in $Sct^{-/-}$, $SR^{-/-}$ and more remarkably in $Sct^{-/-}/SR^{-/-}$ mice compared to the corresponding WT mice (data not shown); also, no significant differences were observed between normal WT and $Sct^{-/-}$, $SR^{-/-}$ and $Sct^{-/-}/SR^{-/-}$ mice. By H&E staining we demonstrated that there were no significant differences in the degree of necrosis, lobular damage, and portal inflammation among the normal liver samples, except for a low degree of lobular damage in $Sct^{-/-}/SR^{-/-}$ normal mice (data not shown). In BDL liver, we found an increase in necrosis, inflammation and lobular damage in all the samples compared to the corresponding WT mice (data not shown). The structure of stomach, small and large intestine, pancreas, lung, spleen and kidney from WT and $Sct^{-/-}/SR^{-/-}$ mice after sham and BDL appear comparable and did not show pathological alterations.

Serum levels of transaminases, ALP and bilirubin increased in BDL WT compared to normal mice but decreased in $Sct^{-/-}$, $SR^{-/-}$ and at higher extend in $Sct^{-/-}/SR^{-/-}$ mice compared to the corresponding WT mice (data not shown); also, no significant differences were observed between normal WT and $Sct^{-/-}$ $SR^{-/-}$ and $Sct^{-/-}/SR^{-/-}$ mice.

Figure 5:
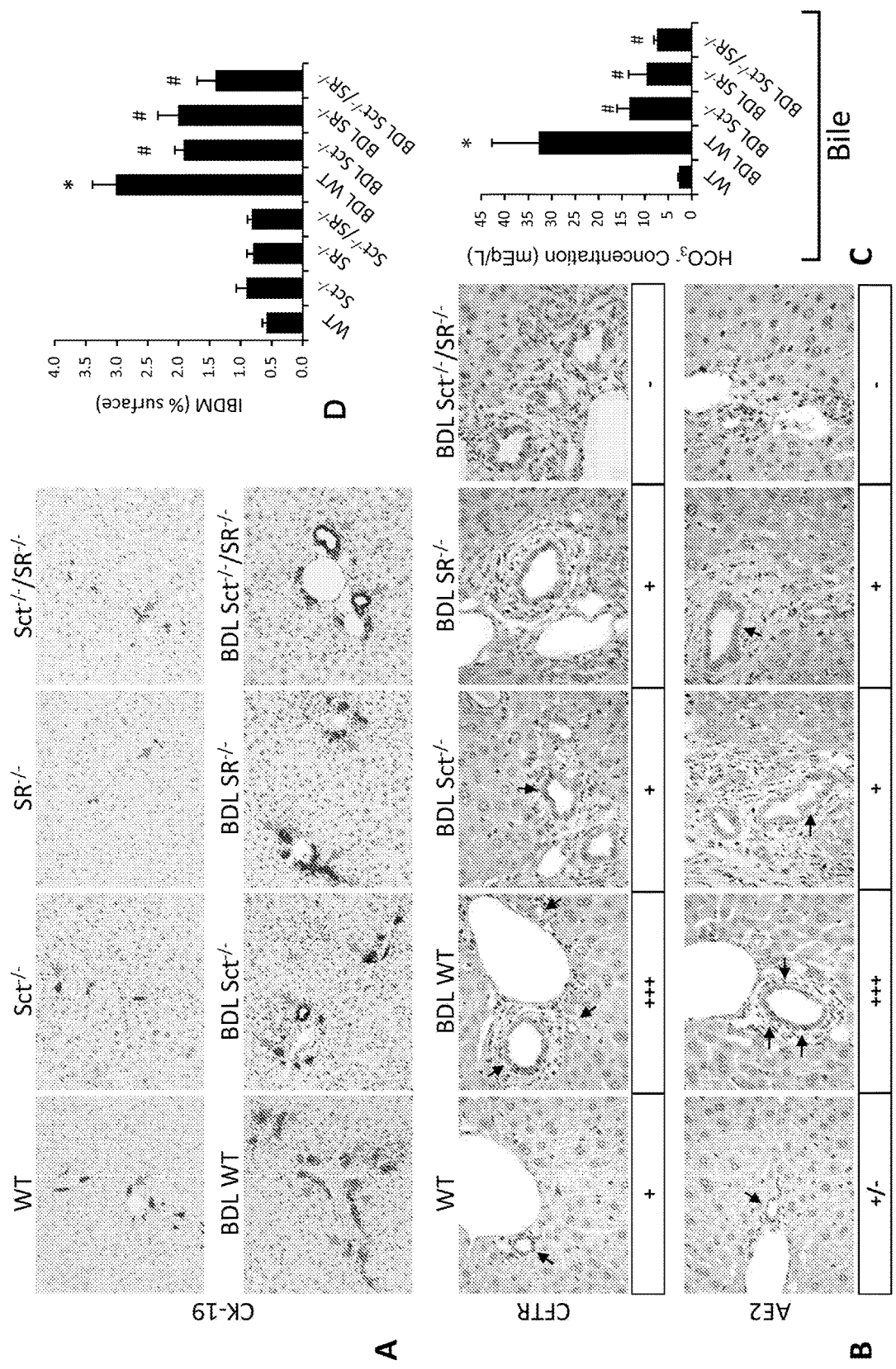
FIG. 5A shows ductular reaction (IBDM) was higher in BDL WT compared to normal WT mice but decreased in $Sct^{-/-}$, SR–/– and $Sct^{-/-}/SR^{-/-}$ BDL compared to BDL WT mice; no significant differences in IBDM were observed between normal WT and $Sct^{-/-}$, $SR^{-/-}$ and $Sct^{-/-}/SR^{-/-}$ mice; green arrows indicate bile ducts positive for CK-19. Orig. magn., ×20. $*p<0.05$ vs normal WT mice; $\#p<0.05$ vs. BDL WT mice.
FIG. 5B shows the immunoreactivity of CFTR and AE2 (black arrows) increased in liver sections from BDL WT compared to WT mice but decreased in $Sct^{-/-}$, $SR^{-/-}$ and $Sct^{-/-}/SR^{-/-}$ BDL mice compared to BDL WT mice. Orig. magn., ×40.
FIG. 5C shows bicarbonate concentration was higher in BDL WT mice compared to normal WT mice but decreased in $Sct^{-/-}$, $SR^{-/-}$ and $Sct^{-/-}/SR^{-/-}$ BDL mice compared to BDL WT mice. Data are mean±SEM of 3 evaluations from 3 individual mice. $*p<0.05$ vs. normal WT mice; $\#p<0.05$ vs. BDL WT mice.
FIG. 5D shows the bar graph of the ductular reaction (IDBM) data from FIG. 5A.

IBDM was higher in BDL WT compared to WT mice but decreased in $Sct^{-/-}$, $SR^{-/-}$ and at higher extend in $Sct^{-/-}/SR^{-/-}$ mice compared to the corresponding WT mice (FIG. 5A). At the functional level, the immunoreactivity of CFTR and AE2 increased in liver sections from BDL WT compared to WT mice but decreased in $Sct^{-/-}$, $SR^{-/-}$ and at higher extend in $Sct^{-/-}/SR^{-/-}$ mice compared to the corresponding WT mice (FIG. 5B). Bicarbonate concentration was higher in BDL WT compared to normal WT mice, but significantly decreased in $Sct^{-/-}$, $SR^{-/-}$ and $Sct^{-/-}/SR^{-/-}$ BDL mice compared to BDL WT mice (FIG. 5C).

Figure 6:
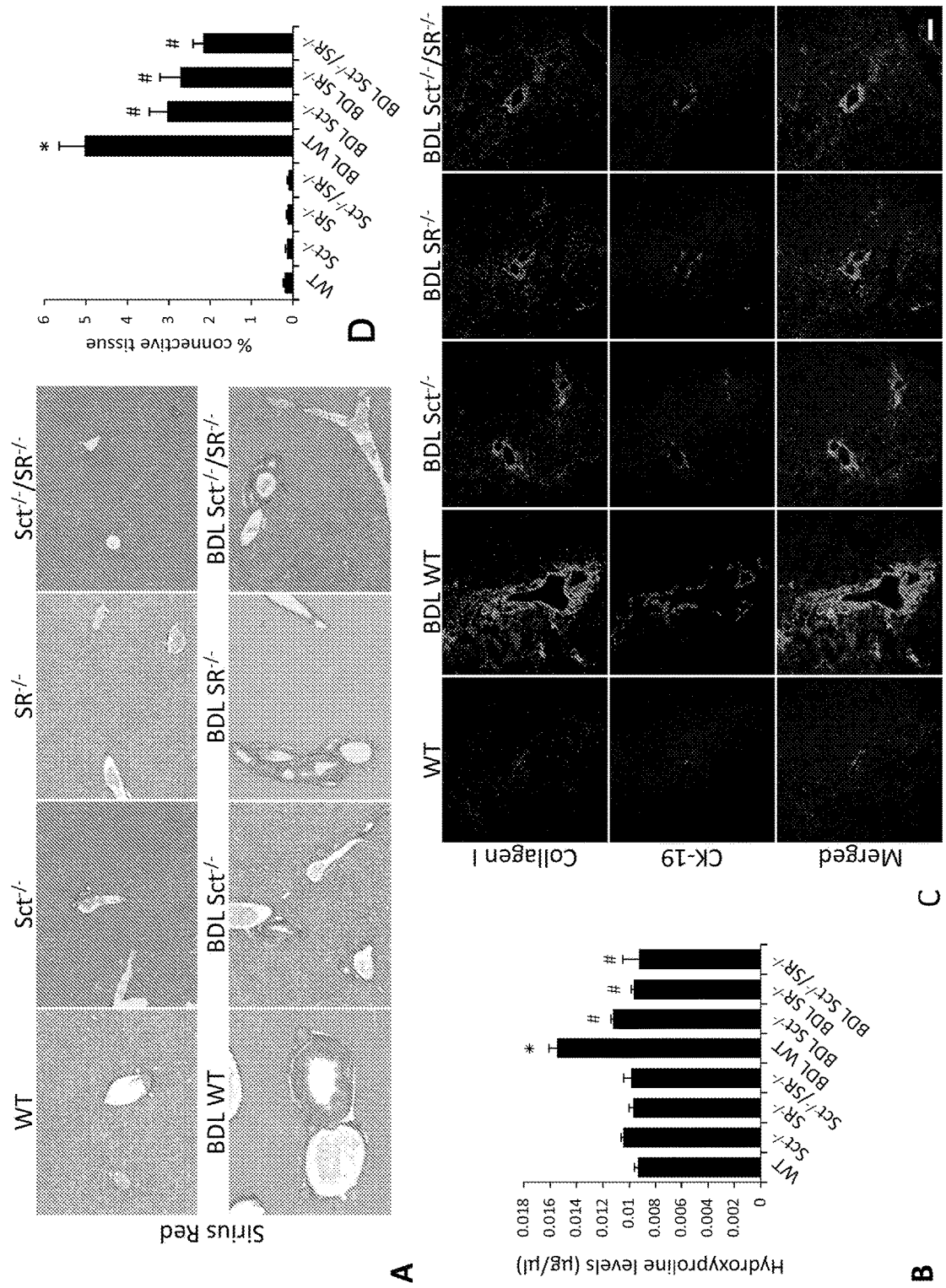
FIG. 6A shows BDL WT mice displayed higher collagen deposition compared to normal WT mice. There was reduced collagen deposition In $Sct^{-/-}$, $SR^{-/-}$ and $Sct^{-/-}/SR^{-/-}$ BDL mice compared to BDL WT mice; knockout of Sct or/and SR did not alter fibrosis in normal mice.
FIG. 6B shows that similar changes in liver fibrosis were observed by measurement of hydroxyproline levels in liver samples. We used 3 different liver samples from three different mice. $*p<0.05$ vs. normal WT mice. $\#p<0.05$ versus BDL WT mice.
FIG. 6C shows BDL WT mice have increased immunoreactivity for Collagen I (green color) in bile ducts (co-stained for CK-19, red color) and periductal region compared to normal WT mice, which returned to values similar to that of normal WT mice in $Sct^{-/-}$, $SR^{-/-}$ and $Sct^{-/-}/SR^{-/-}$ BDL mice. Scale bar=100 µm.
FIG. 6D shows the bar graph of the collagen deposition data from FIG. 6A.

BDL WT mice displayed higher collagen deposition compared to normal WT mice (FIG. 6A). In both normal and BDL $Sct^{-/-}$ and $SR^{-/-}$ mice there was reduced collagen deposition compared to the corresponding WT mice (FIG. 6A). While in normal Sct and $SR^{-/-}$ mice the reduction in collagen deposition was observed in both periportal and pericentral areas, in BDL Sct and $SR^{-/-}$ mice there was higher reduction in collagen deposition in the periportal spaces compared the pericentral regions. The decrease in collagen deposition was more evident in $Sct^{-/-}/SR^{-/-}$ mice compared to $Sct^{-/-}$ and $SR^{-/-}$ mice.

Similar changes in liver fibrosis were observed by measurement of hydroxyproline levels in liver samples (FIG. 6B). BDL WT mice have increased collagen expression in bile ducts and the periductal region compared to WT mice, which was reduced in $Sct^{-/-}$, $SR^{-/-}$ and $Sct^{-/-}/SR^{-/-}$ BDL mice compared to BDL WT mice (FIG. 6C). Furthermore, there was enhanced expression of TGF-β1, TFG-β1R, Col1a1, α-SMA and Fn1 in total liver, isolated cholangiocytes and HSCs from BDL WT mice that was reduced in Sct-/-, $SR^{-/-}$ and $Sct^{-/-}/SR^{-/-}$ BDL compared to BDL WT mice (data not shown). There were increased levels of TGF-β1 in serum as well as cholangiocyte supernatant from BDL WT compared to WT mice, while the increases were reduced in $Sct^{-/-}$, $SR^{-/-}$ and $Sct^{-/-}/SR^{-/-}$ BDL compared to BDL WT mice.

Measurement of Cellular Senescence in Liver Sections and Cholangiocytes and HSCs.

In BDL WT mice, there was increased biliary senescence (by SA-β-gal staining) as well as immunoreactivity for p16 in cholangiocytes (stained with CK-19) compared to WT mice (data not shown). The increased cholangiocyte senescence observed in BDL WT mice was reduced in $Sct^{-/-}$, $SR^{-/-}$ and $Sct^{-/-}/SR^{-/-}$ BDL mice (FIG. 5A-B). A similar profile was observed in isolated cholangiocytes by PCR analysis for p16 and p21 (data not shown). There was reduced expression of p16 and p21 in HSCs from BDL WT compared to WT mice (data not shown), but enhanced cellular senescence in HSCs from Sct-/-, SR-/- and Sct-/-/SR-/- BDL mice compared to BDL WT mice (data not shown).

Measurement of TGF-β1 Levels and Fibrosis and Cellular Senescence in WT Mice and Large IMCLs Treated with Secretin.

There were enhanced levels of TGF-β1 in cholangiocyte supernatant from WT mice treated in vivo with secretin compared to saline-treated mice (data not shown). Treatment of WT mice with secretin increased the biliary immunoreactivity of Collagen I in liver sections as well as mRNA expression of TGF-β1, TFG-β1R, Col1a1, α-SMA and Fn1 in isolated cholangiocytes and HSCs (due a paracrine interaction with cholangiocytes synthesizing more TGF-β1) compared to WT mice (data not shown). We also observed: (i) enhanced p16 immunoreactivity in liver sections as well as p16 and p21 expression in cholangiocytes from secretin-treated WT mice; the stimulatory effect of secretin on biliary senescence is likely due to enhanced release of TGF-β1 that induces cholangiocyte senescence by an autocrine loop; and (ii) reduced p16 and p21 mRNA expression in isolated HSCs (likely due a paracrine interaction with cholangiocytes synthesizing more TGF-β1) from secretin-treated WT mice compared to saline-treated mice (data not shown).

Paracrine Effect of Secretin-Stimulated Biliary TGF-β1 on the Expression of Fibrosis and Senescence Genes in HHSteCs.

When HHSteCs were treated with cholangiocyte supernatants from BDL WT mice (containing higher levels of TGF-β1 compared normal mice, there was enhanced expression of fibrosis genes and reduced expression of senescence genes compared to HHSteCs treated with normal cholangiocyte supernatant (data not shown); the changes in fibrosis and senescence gene expression were reversed in HHSteCs that were treated with cholangiocyte supernatant from $Sct^{-/-}$, $SR^{-/-}$ and $Sct^{-/-}/SR^{-/-}$ BDL mice (data not shown). When HHSteCs were treated with cholangiocyte supernatant from secretin-treated WT mice (containing higher levels of TGF-β1) there was increased expression of fibrosis but reduced expression of senescence genes in HHSteCs (data not shown); these effects were reversed by preincubation of HHSteCs with LY2109761 before incubation with cholangiocyte supernatant from secretin-treated WT mice; no effect was observed with normal cholangiocyte supernatant (data not shown). TGF-β1 stimulates fibrosis gene expression but reduces senescence gene expression in HHSteCs (data not shown). The next in vitro experiments demonstrated that: (i) secretin increased the secretion of TGF-β1 of large IMCLs and the expression of fibrosis and senescence genes, effects that were prevented by preincubation with LY2109761 (data not shown); (ii) TGF-β1 decreased PCNA mRNA expression and increased the expression of fibrosis and senescence genes of large IMCLs (data not shown); and (iii) the supernatant of large IMCLs (containing higher levels of TGF-β1 after secretin treatment) increases fibrosis gene expression but decreases the expression of senescence genes of HHSteCs, effects that were reversed by preincubation with LY2109761 (data not shown).

Expression of the Sct-Dependent microRNA 125b/VEGF-A Axis.

In BDL mice there was reduced expression of miRNA125b and enhanced mRNA expression (in isolated cholangiocytes) as well immunoreactivity (in liver sections) of VEGF-A in BDL WT compared to normal mice, values that returned to values similar to that of normal mice in Sct $SR^{-/-}$ and $Sct^{-/-}/SR^{-/-}$ BDL mice.

Discussion.

Ductular reaction, cellular senescence and liver fibrosis are key hallmarks of chronic cholestatic liver diseases including PSC. We have previously shown that: (i) the Sct/SR axis plays a key role in the enhancement of biliary mass and liver fibrosis in animal models of cholestasis such as BDL and $Mdr2^{-/-}$; and (ii) the Sct/SR axis is upregulated in liver samples from $Mdr2^{-/-}$ mice as well as PSC patients. Our study extends prior observations by elucidating a more in-depth evaluation of the coordinated factors by which the Sct/SR axis stimulates liver fibrosis by: (i) increased cellular senescence in cholangiocytes through an autocrine loop involving decreased expression of microRNA125b and enhanced TGF-β1 biliary secretion and VEGF-A expression following Sct stimulation; and (ii) secretin-mediated paracrine inhibition of HSCs senescence (by secretin-mediated increase of TGF-β1 secretion from cholangiocytes) in BDL WT mice.

Here, we demonstrated that: (i) both biliary mass and hepatic fibrosis are significantly reduced in $Sct^{-/-}$, $SR^{-/-}$ and $Sct^{-/-}/SR^{-/-}$ BDL compared to BDL WT mice, (ii) the reduction of biliary mass (ductular reaction) in $Sct^{-/-}$, $SR^{-/-}$ and $Sct^{-/-}/SR^{-/-}$ BDL mice was coupled with decreased expression of functional markers of the secretory and pro-liferative processes such as CFTR and AE2, and biliary bicarbonate concentration compared to BDL WT mice; (iii) the reduction of hepatic fibrosis observed in $Sct^{-/-}$, $SR^{-/-}$ and $Sct^{-/-}/SR^{-/-}$ BDL mice was associated with reduced TGF-β1 levels in both serum and cholangiocyte supernatant as well as decreased expression of biliary senescence in contrast to increased expression of HSCs senescence compared to the expression levels observed in BDL WT mice; (iv) concomitant with increased ductular reaction and liver fibrosis, secretin directly stimulates cellular senescence in a subset of large cholangiocytes and decreases cellular senescence of HSCs by a paracrine TGF-β1-dependent mechanism; and (v) the supernatants of cholangiocytes (containing higher levels of TGF-β1) activates HSCs through decreased cellular senescence.

There is close relationship between cholangiocyte proliferation/ductular reaction and the expression of the Sct/SR/CFTR/AE2 axis. We have shown that the expression of the Sct/SR axis (present only by cholangiocytes in the liver) is significantly increased in animal models of cholestasis such as BDL and $Mdr2^{-/-}$ mice and in liver samples from patients with PSC. Conversely, the damage of cholangiocytes and the decrease in ductular reaction (for example after acute administration of $CCl_4$ and chronic treatment with γ-aminobutyric acid) is associated with decreased expression of the Sct/SR/CFTR/AE2 axis. Secretin stimulates biliary bicarbonate secretion via cAMP/PKA-dependent activation of CFTR and AE2 exchanger activity and bicarbonate secretion is enhanced in BDL mice. Supporting these previous findings, in our study we demonstrated that knockdown of the Sct/SR axis reduced bicarbonate levels in bile compared to BDL WT mice. Since the studies were performed in mice with BDL for 1 week, the levels of bicarbonate reduction in the mice lacking the Sct/SR axis were not completely reduced to normal basal levels, but remain slightly elevated but significantly decreased compared to BDL wild-type. This may be due to the short time period and/or the remaining stimulus from extrahepatic cholestasis induced by BDL that activates alternative $Ca^{2+}$-dependent $Cl^-$ efflux channels.

The Sct/SR axis has been shown to play a key role in modulating biliary damage, ductular reaction and liver fibrosis during cholestasis through a paracrine interaction with HSCs mediated by secretin-induced increase in TGF-β1 biliary secretion. Cholestasis and hepatic fibrosis are hallmark features observed during the pathogenesis of PSC, which are mimicked in both BDL and $Mdr2^{-/-}$ mice. Recent evidence also implicates a role for cellular senescence in cholestatic liver injury and the pathogenesis of PSC. We demonstrated herein that the reduction of hepatic fibrosis observed $Sct^{-/-}$, $SR^{-/-}$ and $Sct^{-/-}/SR^{-/-}$ BDL mice was associated with reduced levels of TGF-β1 in serum and cholangiocyte supernatant and decreased expression of markers of cellular senescence in cholangiocytes, which was in contrast to increased expression of markers of cellular senescence in HSCs compared to those observed in BDL WT mice. Surprisingly, the decrease in biliary senescence observed in $Sct^{-/-}$, $SR^{-/-}$ and $Sct^{-/-}/SR^{-/-}$ BDL mice was associated with reduced ductular reaction that may likely be due to lack of the proliferative stimulus of the Sct/SR axis that increases biliary senescence likely through an autocrine TGF-β1 secretory loop. The unexpected enhanced biliary senescence observed in BDL WT mice (that are characterized by increased ductular reaction) is likely to due to enhanced biliary TGF-β1 secretion (mediated by secretin) that in addition to induce the activation of HSCs (by a paracrine pathway) reduces biliary proliferation while triggering cholangiocyte senescence as well. The increase in biliary senescence observed after BDL may be limited to a subset of large cholangiocytes damaged in this hyperplastic model. This concept is also supported by data (not shown) showing that large are more senescent compared to small, undifferentiated cholangiocytes as well by the findings that TGF-β1 increases senescence while decreasing PCNA expression of large IMCLs. It is important to note that only large cholangiocytes express SR in the BDL model. However, further studies are necessary to pinpoint the specific subpopulations of large cholangiocytes undergoing senescence in the BDL model of biliary hyperplasia. In support of our findings, inhibition of the proliferative substance P/neurokinin-1 receptor axis in cholangiocytes during cholestasis has been shown to reduce biliary senescence and trigger senescence of HSCs reducing hepatic fibrosis. This concept is further supported by a previous study showing that atorvastatin inhibits proliferation and apoptosis but induces senescence of rat hepatic myofibroblasts decreasing liver fibrosis. Furthermore, another study demonstrated that cholangiocyte senescence is elevated in human PSC samples as well as in experimentally induced biliary senescence that was dependent upon the activation of N-Ras. In fact, targeting senescent cholangiocytes with a Bcl-xL-specific inhibitor reduced hepatic fibrosis in cholestatic Mdr2$^{-/-}$ mice via a dual effect on activated HSCs and senescent cholangiocytes. In support of our findings and the association between enhanced biliary damage (such as in the BDL model) and cellular senescence, a recent study demonstrated: (i) a link between biliary injury (observed during early chronic liver allograft rejection) and senescence; and (ii) the role of TGF-β1 in promoting senescence of bile ducts. Another recent study provides further support for the role of TGF-β1 in regulating cellular senescence of hepatic cells by demonstrating that sirtuin 6 promotes TGF-β1-mediated increases of hepatocellular carcinoma (HCC) cell tumorigenicity by reducing cellular senescence of malignant hepatocytes. Furthermore, TGF-β1 has been shown to inhibit the proliferation of HCC cells by increased cellular senescence of HCC cells. Finally, a number of studies demonstrate that TGF-β phosphorylates Smad2/3 to mediate p16 or p21 to induce the senescence in several cell types including fibroblasts, colon cancer cells and hepatoma cells, which supports the concept that TGF-β-signaling regulates the cellular senescence of cholangiocytes and HSCs in our study.

Our study introduces the novel concept that secretin-induced biliary TGF-β1 secretion increase cellular senescence of cholangiocytes by an autocrine loop, which in turn releases proinflammatory factors (i.e., senescence-associated secretory phenotypes, SASP) including TGF-β1, triggering liver fibrosis through reduced senescence of HSCs. In contrast, the knockdown of the Sct/SR axis limits ductular reaction and compensatory cholangiocyte senescence and reduces the levels of TGF-β1 that limits the activation of HSCs through increased senescence of HSCs. This balance between cholangiocyte and HSCs senescence plays a critical role in the progression of fibrosis in cholestatic liver diseases.

In summary, we demonstrated that the Sct/SR axis plays a key role in the pathogenesis of ductular reaction and hepatic fibrosis during cholestatic liver injury that involved differential regulation of cellular senescence in cholangiocyte and HSCs that was likely mediated by changes in biliary TGF-β1 secretion. Our findings indicate that a balance between cholangiocyte and HSC senescence plays a key role in the regulation of ductular reaction and hepatic fibrosis and implies that targeting senescent cholangiocytes by modification of the Sct/SR can provide a key pharmacological approach for reducing hepatic fibrosis during the progression of cholestatic liver diseases.

Example 3. Secretin Knockout Reduces Liver Damage in Alcoholic Liver Disease

Introduction:

Alcoholic liver disease (ALD) is a chronic disease that is widespread and culminates in cirrhosis and ultimately hepatocellular carcinoma. Cholangiocytes are the target cells of cholangiopathies but their role in ALD is undefined. A hallmark of biliary damage/repair is ductular response in response to liver injury during ALD. Proliferating cholangiocytes display a neuroendocrine phenotype characterized by the activation of the Sct/SR axis that is expressed only by cholangiocytes in the liver. We tested the hypothesis that inhibition of the Sct/SR axis ameliorated liver damage caused by ALD.

Methods.

Human patient liver samples from normal and steatohepatitis heavy drinkers (SHD) were obtained from Xenotech (Kansas City, Kans.). Immunohistochemistry was performed for H&E, collagen1A1 (Col1A1), cytokeratin-19 (CK-19, to measure intrahepatic biliary mass, IBDM), Sct, SR and cellular senescence evaluated by SA-β-galactosidase (SA-β-gal) staining and qPCR for p16 and p21. qPCR was performed for Sct and SR and TFG1. C57BL6 (WT) and Sct$^{-/-}$ mice were fed 5% ethanol ad libitum for 8 weeks with a weekly ethanol gavage of 5 g/kg BW. Livers were stained for H&E, Oil Red O, Sirius Red, Col1A1, α-SMA, CK-19, Sct and SR. qPCR was performed for the fibrotic markers, Col1A1, desmin, MMP1, fibronectin (Fn-1) and TIMP1/4. Hepatic stellate cells (HSCs) were isolated from liver sections by laser capture microdissection (LCM), mRNA was extracted, and qPCR was performed for markers of fibrosis. qPCR was performed on isolated cholangiocytes from WT or Sct$^{-/-}$ mice for Col1A1, VEGF-A and SR.

Table 1 (below) shows the characteristics of healthy controls and patients with alcohol-induced steatohepatitis.

TABLE 1

Characteristics of healthy controls and patients with alcohol-induced steatohepatitis.
Human samples were obtained from Sekisui XenoTech Company.

| Diagnosis | Samples ID | Macro fat % | Age | Sex | Ethnicity | BMI | Alcohol Use | Alcohol Use Frequency | Diabetes |
|---|---|---|---|---|---|---|---|---|---|
| Normal | H1255 | 1-2 | 56 | F | African American | 25 | No | N/A | No |
|  | H1293 | 0 | 52 | F | Caucasian | 29.1 | No | N/A | No |
|  | H1296 | 0 | 46 | M | Caucasian | 21.1 | No | N/A | No |
|  | H1299 | 0 | 17 | F | Caucasian | 20.6 | Yes | Occasional | No |
| Steatohepatitis | H0959 | 40 | 48 | M | Caucasian | 32.2 | Yes | Heavy | No |
|  | H1063 | 80 | 43 | M | Hispanic | 19.5 | Yes | Heavy | No |
|  | H1259 | 20 | 64 | M | Caucasian | 33.2 | Yes | Heavy | Yes |

Results.

Figure 4:
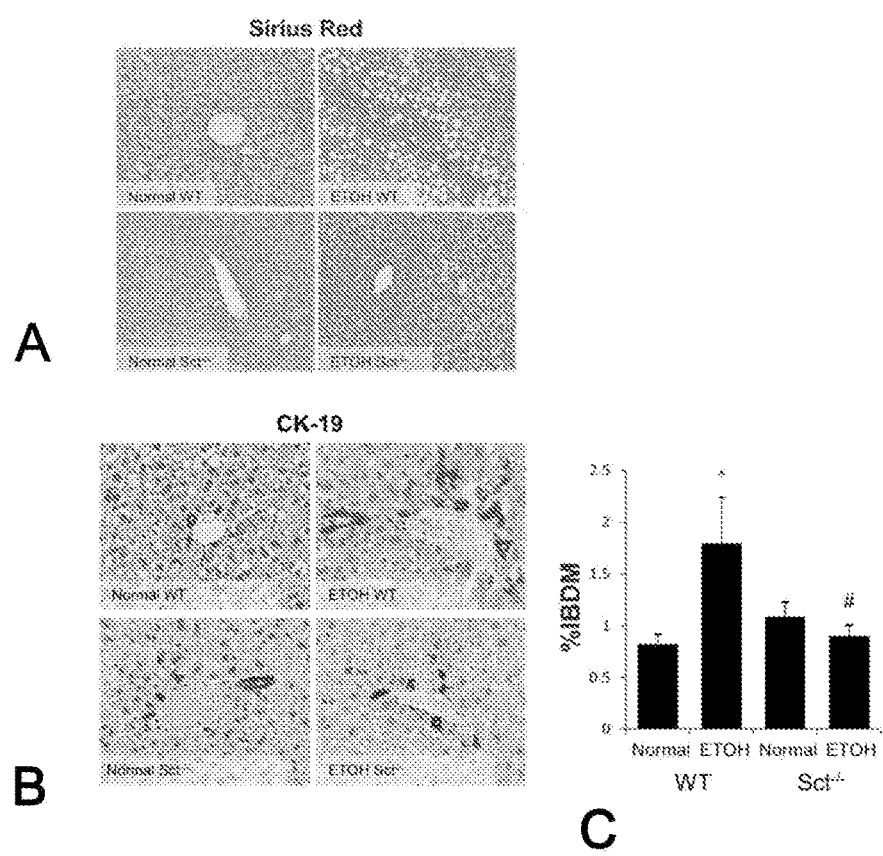
FIG. 4A-C shows that biliary proliferation and hepatic fibrosis are increased in ethanol fed wild-type (WT) mice. Both biliary proliferation and hepatic fibrosis are ablated in ethanol fed secretin ($Sct^{-/-}$) knockout mice.

Patient SHD samples showed increased IBDM, liver fibrosis and steatosis compared to normal (see, FIG. 4A-C). These samples had also increased levels of liver fibrosis markers Col1A1 and TGFβ1. Secretin and SR were increased in the cholangiocytes of SHD patients. (See, FIG. 3A-D). There were enhanced SA-β-gal staining and increased levels of p16 and p21 in cholangiocytes in SHD patients compared to normal (data not shown). $Sct^{-/-}$ mice fed with an ethanol diet showed decreased ALT and AST levels, IBDM, liver fibrosis, steatosis, Col1A1, and TIMP1/4 compared to WT ethanol fed mice. Isolated cholangiocytes from ethanol fed $Sct^{-/-}$ mice showed decreased levels of Col1A1 and VEGF-A compared to WT controls. Cholangiocytes from ethanol fed Sct mice also had decreased levels of SR. LCM-isolated HSCs derived from WT mice showed increased levels of α-SMA, Col1A1 and Fn-1 that were reduced in $Sct^{-/-}$ mice.

Conclusion.

The Sct/SR axis plays an important role during ALD-induced liver injury. Downregulation of the Sct/SR biliary axis through repression of Sct secretion can be an important approach to ameliorate liver damage in ALD patients.

Example 4. Knockout of Secretin Receptor Reduces Biliary Damage and Liver Fibrosis in $Mdr2^{-/-}$ Mice by Diminishing Senescence of Cholangiocytes Materials.

Unless otherwise stated, reagents were purchased from Sigma-Aldrich Co. (St. Louis, Mo.) unless otherwise indicated. The RNeasy Mini Kits for RNA isolation and the selected mouse and human PCR primers were purchased from Qiagen (Valencia, Calif.). PCR primers were the following: PCNA (NM_011045); Ki67 (NM_001081117); TGF-β1 (NM_011577); fibronectin-1 (FN-1, NM_010233); collagen, type I, alpha (Col1a1, NM_007742); cyclin-dependent kinase inhibitor 2A (CDKN2A/p16INK4a, p16, NM_009877); CCL2 (NM_011333); interleukin 6 (IL-6, NM_031168); tumor necrosis factor alpha (TNF-α, NM_013693); vascular endothelial growth factor-A (VEGF-A, NM_009505); VEGFR-2 (NM_010612); platelet endothelial cell adhesion molecule 1 (PECAM-1, AKA CD31, NM_008816); Von Willebrand factor (vWF, NM_011708); and glyceraldehyde-3-phosphate dehydrogenase (GAPDH, NM_008084). List of human PCR primers: p16 (NM_000077); CCL2 (NM_002982); Col1a1 (NM_000088); FN-1 (NM_002026); VEGFA (NM_001025360; and GAPDH (NM_001256799).

Antibodies.

The antibody for SR was obtained from Bioss (Woburn, Mass.). The antibodies foSMA, CD31, cytokeratin-19 (CK-19), Col1a1, desmin, IL-6, p16, TNF-α, VEGF-A and VEGFR-2 were obtained from Abcam (Cambridge, Mass.). Enzyme-linked immunosorbent assay (ELISA) kits to measure TGF-β1 levels were purchased from Affymetrix Inc. (Santa Clara, Calif.).

Animal Models.

The animal experiments were performed according to protocols approved by the Baylor Scott & White IACUC Committee. Male C57BL/6 wild-type (WT) mice (control for $SR^{-/-}$ mice) were purchased from Charles River (Wilmington, Mass.). Male FVB/NJ WT mice (25-30 gm, control for $Mdr2^{-/-}$ mice) were purchased from Jackson Laboratories (Bar Harbor, Me.). C57/FVB WT mice were obtained after breeding C57BL/6 with FVB/NJ mice. Both $SR^{-/-}$ and $Mdr2^{-/-}$ mouse colonies are established in our animal facility. The established mouse strains (having different backgrounds), $SR^{-/-}$ and $Mdr2^{-/-}$, were crossed until the homozygous double knockout ($SR^{-/-}/Mdr2^{-/-}$) mice were obtained.

Genotyping.

The genotype of each $SR^{-/-}/Mdr2^{-/-}$ mouse was confirmed by PCR amplification of genomic DNA extracted from the tail. Genotyping was performed by Charles River Laboratories. The SR–/– genotype was identified using three primers: SR-WT-Forward: 5'-GAG TGC CAC CTT GCC CTG-3'//SEQ ID NO:4, SR-KO-Forward: 5'-CCC ATG GCT CAG GCA AG-3'//SEQ ID NO:10, Sct-COM-Reverse: 5'-GTG CCT GAG GTT TCA TAC TCA G-3'//SEQ ID NO:11, with migration positions for WT at 551 bp and SR–/– at 240 bp, respectively. The sequence of primers for identification of Mdr2–/– is Mdr2-WT-s: 5'-CAA CAC GCG CTG GAA GTT CA-3'//SEQ ID NO:12, Mdr2_WT_as: 5'-GAT GCT GCC TAG TTC AAA GTC G-3'//SEQ ID NO:13; Mdr2_Neo_s: 5'-TGT CAA GAC CGA CCT GTC CG-3'//SEQ ID NO:14; Mdr2_Neo_as: 5'-TAT TCG GCA AGC AGG CAT CG-3'//SEQ ID NO:15; with migration positions for WT at 276 bp and Mdr2–/– at 400 bp, respectively.

Western Blot.

The protein of liver samples was extracted with lysis buffer and quantified by the bicinchoninic acid method (Pierce Biotechnology, Inc., Rockford, Ill.). Then, the protein expression of Col1a1, Fn1, p16, PCNA, TGF-β1 receptor (TGF-β1R), TNF-α and VEGF-A was evaluated by immunoblots. Protein expression was visualized and quantified using the LI-COR Odyssey Infrared Imaging System (LI-COR Bioscience, Lincoln, Nebr.). Animals were maintained in a temperature-controlled environment (20-22° C.) with 12:12-hr light/dark cycles and fed ad libitum standard chow with free access to drinking water. The experiments were performed in the corresponding WT mice as well as $SR^{-/-}$, $Mdr2^{-/-}$ and $SR^{-/-}/Mdr2^{-/-}$ mice (all 12 wk age). Before liver perfusion, animals were treated with euthasol (200-250 mg/kg BW). In all groups, we measured liver and body weight and liver to body weight ratio, an index of liver cell growth.

Isolated Cholangiocytes and Laser Capture Microdissection (LCM)-Isolated HSCs.

Cholangiocytes were obtained by immunoaffinity separation, Cholangiocytes were obtained by immunoaffinity separation as described herein above, using a monoclonal antibody (a gift from Dr. R. Faris, Brown University, Providence, R.I.) that is expressed by all intrahepatic cholangiocytes. Cell viability (greater than 97%) was assessed by trypan blue exclusion. HSCs were isolated by LCM as described herein above. Frozen liver sections (n=3, 10 μm thick) were incubated overnight with an antibody against desmin (marker of stellate cells). Following staining, desmin-positive HSCs were dissected from the slides by a LCM system Leica LMD7000 (Buffalo Grove, Ill.) and collected into a PCR tube before being analyzed. The RNA from HSCs was extracted with the Arcturus PicoPure RNA isolation kit (Thermo Fisher Scientific CO, Mountain View, Calif.). The in vitro studies were performed in our immortalized murine biliary cell lines (IMCLs) and human hepatic stellate cell lines (HHSteCs, Sciencell, Carlsbad, USA).

SR Immunoreactivity in Liver Sections and Sct Levels in Serum and Cholangiocyte Supernatant.

The immunoreactivity of SR was measured by immunohistochemistry in paraffin-embedded liver sections (4-5 μm thick, 10 different fields from 3 samples from 3 animals). Observations were processed by Image-Pro Plus software (Media Cybernetics, Silver Springs, Md.) in a blinded fashion by one board-certified pathologist. Sct levels were measured in serum and cholangiocyte supernatant by ELISA kits (Phoenix Pharmaceuticals, Inc., Burlingame, Calif.).

Measurement of Liver Histology, Serum Chemistry and Intrahepatic Ductal Mass (IBDM).

The histology of liver, pancreas, heart, spleen, lung, kidney, stomach, small and large intestine was evaluated in paraffin-embedded liver sections (4-5 μm thick) by hematoxylin and eosin staining. Observations were processed by Image-Pro Plus software (Media Cybernetics) in a blinded fashion by a board-certified pathologist. Serum levels of glutamate pyruvate transaminases (SGPT), glutamic oxaloacetic transaminase (SGOT) and alkaline phosphatase (ALP) were measured by IDEXX Catalyst One Chemistry Analyzer and VetLab Station (Westbrook, Me.). IBDM in paraffin-embedded liver sections (4-5 μm thick, 10 fields evaluated from 3 samples from 3 animals) was measured. Sections were examined by the Olympus Image Pro-Analyzer software (Olympus, Tokyo, Japan). Biliary proliferation was evaluated by measurement of PCNA and Ki67 expression in cholangiocytes by immunoblots and/or qPCR. qPCR was performed using $RT^2$ SYBR Green/ROX quantitative PCR master mix for the Applied Biosystems ViiA7 real-time PCR system (Life Technologies; Carlsbad, Calif.) according to the manufacturer's protocol.

Measurement of Liver Fibrosis in Liver Sections, Cholangiocytes and HSCs, and TGF-β1 Levels in Serum and Cholangiocyte Supernatant.

Liver fibrosis was evaluated by Sirius Red staining in paraffin-embedded liver sections (4-5 μm thick, 10 different fields analyzed from 3 samples from 3 animals). Collagen content was quantified by Image-Pro Plus software (Media Cybernetics, Silver Springs, Md.). Immunofluorescence double staining was performed for Col1a1 (co-stained with CK-19) or α-SMA (costained with desmin) in frozen liver sections (10 μm thick). Immunofluorescent staining was visualized using Leica TCS SP5 X system (Leica Microsystems Inc.). The mRNA expression of Col1a1 and FN-1 was evaluated in cholangiocytes and/or HSCs by qPCR and/or immunoblots. TGF-β1 levels in serum and cholangiocyte supernatant were measured by ELISA kits.

Measurement of Cellular Senescence in Liver Sections, Isolated Cholangiocytes and HSCs.

Biliary senescence was evaluated in frozen liver sections (10 μm thick) by staining for SA-β-gal using commercially available kits (MilliporeSigma, Billerica, Mass.); all the experiments were performed in 3 different liver samples from 3 animals. By immunofluorescence for p16 (co-stained with CK-19) senescence was measured in frozen liver sections (10 μm thick) for cholangiocytes. The expression of the senescent genes p16 and CCL2 were evaluated in cholangiocytes and HSCs by immunoblots and/or qPCR. The genes related to senescence, fibrosis and angiogenesis were analyzed using Ingenuity pathway analysis (IPA) software (Ingenuity System, Qiagen, Redwood City, Calif.) for the functionally relevant pathway[1,2]. IPA is a web-based functional analysis software that helps researchers to search for targeted information on genes, proteins, chemicals, diseases, and drugs, as well as building custom biological models in life science research.

Expression of microRNA 125b, VEGF-A, VEGFR-2, CD31 and vWF.

The expression of Sct-dependent microRNA 125b (that regulates IBDM and liver fibrosis through changes in the expression of biliary VEGF-A) was measured by qPCR[9]. By immunohistochemistry, we evaluated the semiquantitative immunoreactivity for VEGF-A in liver sections (4-5 μm thick, 10 different fields analyzed from 3 different samples). When 0-5% of bile ducts were positive for VEGF-A, a negative score was assigned; a +/- score was assigned when 6-10% of bile ducts were positive; a + score was assigned when 11-30% of bile ducts were positive; a ++ score was assigned with 31-60% of bile ducts positive; and a score +++ was assigned when more than 61% of bile ducts were positive. The mRNA expression of: (i) VEGF-A/R-2 in cholangiocytes and total liver; and (ii) CD31 and vWF in total liver was evaluated by immunoblots and/or qPCR. Immunofluorescence for the expression of CD31 was performed in frozen liver sections (10 μm thick). Immunofluorescent staining was visualized using Leica TCS SP5 X system (Leica Microsystems Inc.).

In Vitro Effect of Cholangiocyte Supernatant on the Expression of Senescent and Fibrosis Genes in HHSteCs.

We performed experiments to demonstrate that cholangiocyte supernatant (displaying different levels of TGF-β1 depending on the expression of the Sct/SR axis) differentially affect the expression of senescence and fibrosis of HHSteCs. In biliary supernatants, the levels of TGF-β1 were measured by ELISA kits. HHSteCs were incubated with cholangiocyte supernatants from the selected groups of animals for 12 hr (in the absence or presence of LY2109761, 10 μM, a TGF-β1 receptor antagonist, Cayman Chemical, Ann Arbor, Mich.) before measuring the expression of VEGF-A and senescent and fibrosis genes by qPCR. To determine that Sct increases TGF-β1 levels by a microRNA 125b-dependent mechanism, IMCLs were treated with Sct (10 nM in the absence/presence of a microRNA 125b mimic precursor, 5 μM) for 12 hr before measuring TGF-β1 mRNA expression (by qPCR) and secretion by ELISA kits. To provide conclusive evidence that TGF-β1 directly modulates the function IMCLs and HHSteCs, these cells were stimulated with TGF-β1 (10 nM) for 12 hr before measuring the expression of VEGF-A and senescent and fibrosis genes by qPCR. IMCLs and HHSteCs were treated with r-VEGFA (100 nM) for 12 hr at 37° C. before measuring the expression of senescent and fibrosis markers by qPCR. We also evaluated by immunofluorescence the expression of VEGFR-2 in cell smears of IMCLs and HHSteCs. Immunofluorescent staining was visualized using Leica TCS SP5 X system (Leica Microsystems Inc.).

Statistical Analysis.

Data are expressed as mean±SEM. Differences between groups were analyzed by Student's unpaired t-test when two groups were analyzed and ANOVA when more than two groups were analyzed, followed by an appropriate post hoc test.

Results.

Validation of the $SR^{-/-}/Mdr2^{-/-}$ Mouse Model: Expression of SR in Liver Sections.

To validate SR and Mdr2 deletion in $SR^{-/-}/Mdr2^{-/-}$ homozygous mice, genomic DNA was extracted from tail and subjected to PCR genotyping analysis. DNA from $SR^{-/-}/Mdr2^{-/-}$ mice showed bands corresponding to the mutant alleles of both SR and Mdr2. There was enhanced immunoreactivity of SR in liver sections from $Mdr2^{-/-}$ compared to the corresponding WT mice (data not shown); no immunoreactivity for SR was observed in $SR^{-/-}$ and $SR^{-/-}/Mdr2^{-/-}$ mice compared to WT mice (data not shown).

Loss of SR in $Mdr2^{-/-}$ mice Ameliorates Liver Damage.

$Mdr2^{-/-}$ mice display typical features of PSC such as increased connective tissue deposition and higher inflammatory infiltration, phenotypes that were improved in $SR^{-/-}/Mdr2^{-/-}$ mice; no significant changes were noted in $SR^{-/-}$ compared to WT mice. No significant changes were observed in the morphology of pancreas, heart, kidney, stomach, small and large intestine in all animal groups. The spleen of $Mdr2^{-/-}$ mice showed a higher presence of white pulp compared to red pulp, probably due to an increase in the inflammatory reaction. There was enhanced inflammatory infiltration in the pulmonary parenchyma of the lungs of $Mdr2^{-/-}$ mice that was reduced in $SR^{-/-}/Mdr2^{-/-}$ mice. Liver to body weight ratio increased in $Mdr2^{-/-}$ compared to the corresponding WT mice but decreased in $SR^{-/-}/Mdr2^{-/-}$ compared to $Mdr2^{-/-}$ mice (Table 1). Serum levels of SGPT, SGOT and ALP increased in $Mdr2^{-/-}$ compared to WT mice but decreased in $SR^{-/-}/Mdr2^{-/-}$ compared to $Mdr2^{-/-}$ mice (data not shown). There were enhanced TGF-β1 serum levels in $Mdr2^{-/-}$ compared to WT mice, levels that returned to values similar to that of normal values in $SR^{-/-}/Mdr2^{-/-}$ mice (data not shown).

Decreased IBDM and Liver Fibrosis in $SR^{-/-}/Mdr2^{-/-}$ Mice.

Figure 7:
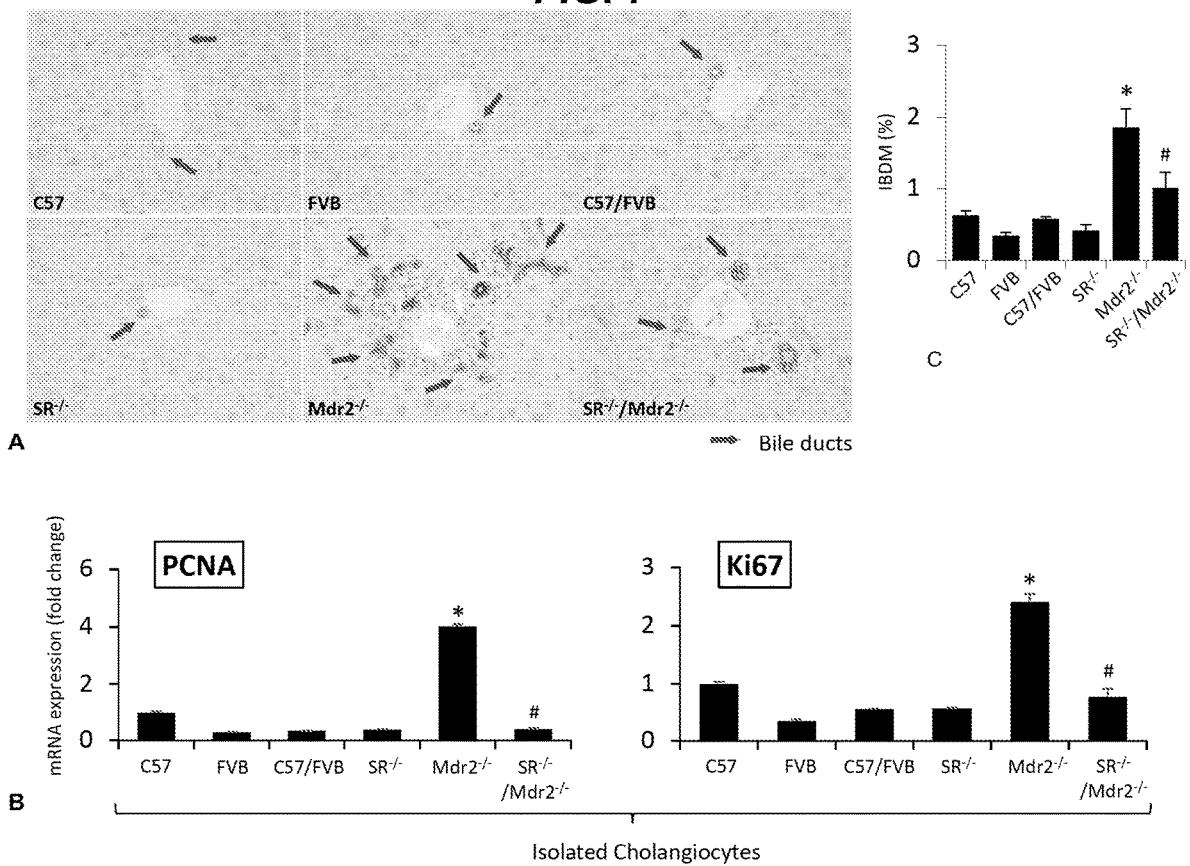
FIG. 7A-B shows measurement of ductular reaction.
FIG. 7C is a bar graph of the ductular reaction data in FIG. 7A.
Figure 8:
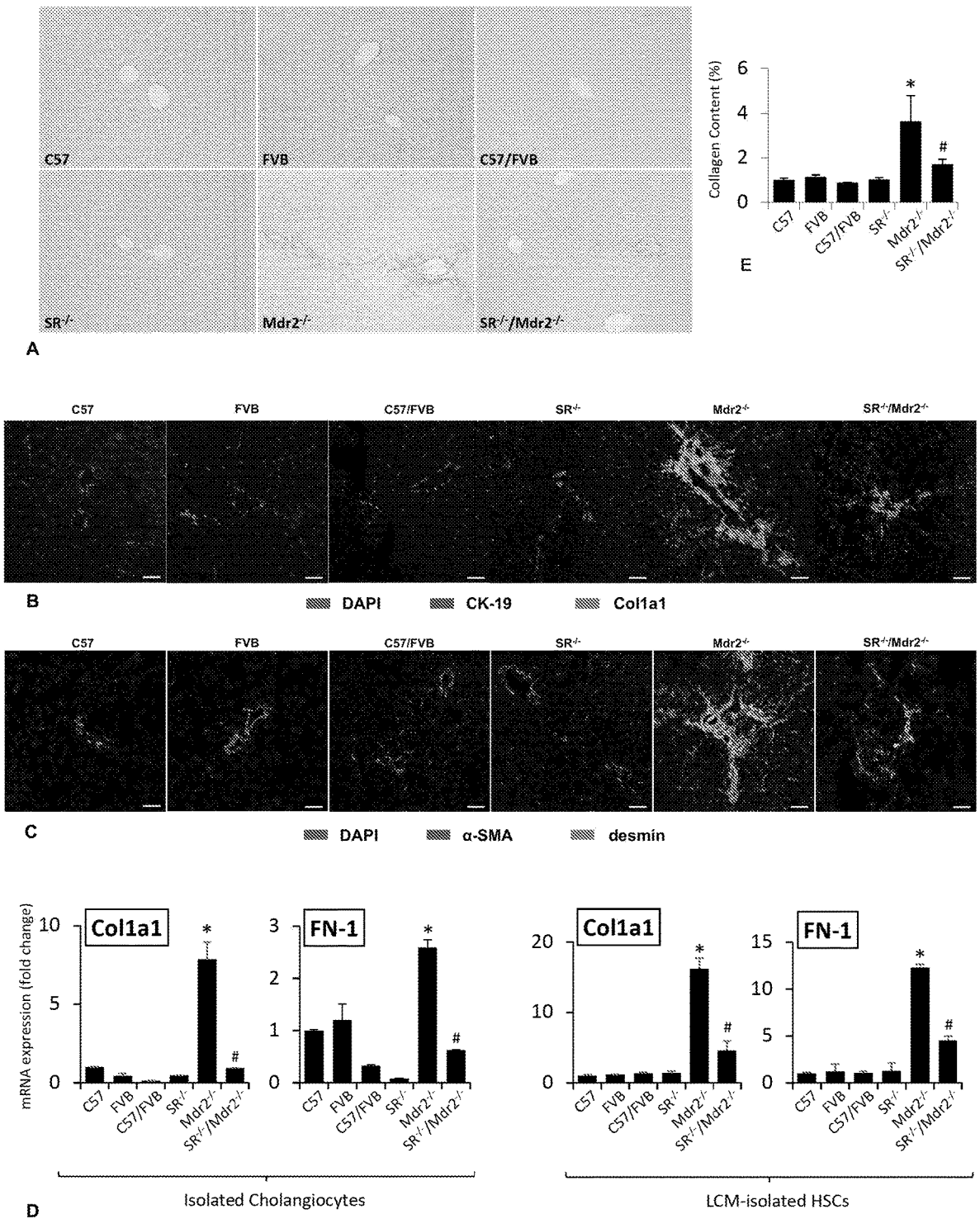
FIGS. 8A-D illustrates collagen deposition in liver sections.
FIG. 8E shows the graph of the collagen deposition data form FIG. 8A.

In $Mdr2^{-/-}$ mice, there was increased IBDM compared to WT mice, which was reduced in $SR^{-/-}/Mdr2^{-/-}$ compared to $Mdr2^{-/-}$ mice (FIG. 7A); no significant changes in IBDM were noted in SW compared to WT mice (FIG. 7A). There was increased expression of PCNA and Ki67 in cholangiocytes from $Mdr2^{-/-}$ mice, which was decreased in $SR^{-/-}/Mdr2^{-/-}$ compared to $Mdr2^{-/-}$ mice (FIG. 7B); no significant changes were observed in the biliary expression of PCNA and Ki67 in $SR^{-/-}$ mice compared to WT mice (FIG. 7B). There was enhanced collagen deposition in liver sections from $Mdr2^{-/-}$ compared to WT mice, which was significantly decreased in $SR^{-/-}/Mdr2^{-/-}$ compared to $Mdr2^{-/-}$ mice (FIG. 8A). By immunofluorescence in liver sections, there was enhanced immunoreactivity for Col1a1 (green color costained with CK-19, red) in $Mdr2^{-/-}$ compared to WT mice, which was reduced in $SR^{-/-}/Mdr2^{-/-}$ compared to $Mdr2^{-/-}$ mice (FIG. 8B). Similarly, there was enhanced co-localization of α-SMA (red) and desmin (green) in HSCs from $Mdr2^{-/-}$ compared to WT mice, immunoreactivity that was decreased in $SR^{-/-}/Mdr2^{-/-}$ compared to $Mdr2^{-/-}$ mice (FIG. 8C). In addition, there was enhanced expression of Col1a1 and FN-1 in isolated cholangiocytes and HSCs from $Mdr2^{-/-}$ mice compared to the corresponding WT mice, increase that was significantly reduced in $SR^{-/-}/Mdr2^{-/-}$ mice compared to $Mdr2^{-/-}$ mice (FIG. 8D).

Loss of SR in $Mdr2^{-/-}$ Mice Decreases Biliary Senescence but Increases Cellular Senescence of HSCs.

IPA was performed to ascertain the cellular context of the differentially expressed signaling mechanisms related to the Sct/SR axis mediated liver injury. IPA analysis demonstrated that the cellular senescence pathway was the altered signaling through p16 and CCL2-related pathological mechanisms (related by the Sct/SR/micro RNA 125b/TGF-β1/VEGF-A axis). To evaluate the underlying mechanisms by which the modulation of SR expression regulates liver fibrosis, we evaluated the effect of SR knock-out on cellular senescence in liver sections, isolated cholangiocytes and HSCs. By SA-β-gal staining in liver sections there was enhanced biliary senescence from $Mdr2^{-/-}$ compared to WT mice, which was significantly decreased in $SR^{-/-}/Mdr2^{-/-}$ when compared to $Mdr2^{-/-}$ mice (data not shown). By immunofluorescence in liver sections from $Mdr2^{-/-}$ mice, there was enhanced immunoreactivity for p16 (costained with CK-19) in cholangiocytes compared to WT mice, immunoreactivity that was reduced in $SR^{-/-}/Mdr2^{-/-}$ compared to $Mdr2^{-/-}$ mice (data not shown). There was enhanced expression of p16 and CCL2 in cholangiocytes from $Mdr2^{-/-}$ mice compared to WT mice, which decreased in $SR^{-/-}/Mdr2^{-/-}$ compared to $Mdr2^{-/-}$ mice (data not shown). Conversely, the expression of p16 and CCL2 was significantly decreased in HSCs from $Mdr2^{-/-}$ compared to WT mice, changes that returned to values similar to that of normal WT group in $SR^{-/-}/Mdr2^{-/-}$ mice (data not shown).

Loss of SR in $Mdr2^{-/-}$ Mice Decreases Sct Levels, the Expression of MicroRNA 125b and Angiogenesis Genes.

Sct levels in serum and cholangiocyte supernatant were increased in $Mdr2^{-/-}$ mice compared to WT mice, which was decreased in $SR^{-/-}/Mdr2^{-/-}$ compared to $Mdr2^{-/-}$ mice (data not shown). Consistent with our previous study[2], the expression of microRNA 125b decreased in cholangiocytes from $Mdr2^{-/-}$ compared to WT mice, expression that returned to values similar to that of normal WT group in $SR^{-/-}/Mdr2^{-/-}$ mice (data not shown). We also demonstrated: (i) enhanced expression of VEGF-A and VEGFR-2 in cholangiocytes and total liver as well as CD31 and vWF in total liver from $Mdr2^{-/-}$ mice compared to WT mice, changes that returned to values similar to that of normal WT group in $SR^{-/-}/Mdr2^{-/-}$ mice (data not shown); and (ii) increased immunoreactivity for VEGF-A and CD31 in liver sections from $Mdr2^{-/-}$ compared to relative WT mice, which was reduced in $SR^{-/-}/Mdr2^{-/-}$ compared to $Mdr2^{-/-}$ mice (data not shown).

In Vitro Paracrine Effect of Cholangiocyte Supernatant on the Expression of Senescent and Fibrosis Genes in HHSteCs.

There were enhanced levels of Sct-stimulated TGF-β1 in cholangiocyte supernatant from $Mdr2^{-/-}$ mice (containing higher Sct levels compared to normal cholangiocyte supernatant), levels that returned to values similar to that of relative WT group in cholangiocyte supernatant from $SR^{-/-}/Mdr2^{-/-}$ mice. There was increased expression of VEGF-A and fibrotic markers but decreased senescence gene expression in HHSteCs treated with cholangiocyte supernatants from Mdr2$^{-/-}$ mice (containing higher levels of TGF-β1) compared to HHSteCs treated with supernatant from WT mice; these changes returned to normal levels when HHSteCs were treated with cholangiocyte supernatant from SR$^{-/-}$/Mdr2$^{-/-}$ mice (data not shown). These effects were also reversed when HHSteCs were preincubated with LY2109761 before treatment with the cholangiocyte supernatants from Mdr2$^{-/-}$ mice (data not shown). Sct increased TGF-β1 mRNA expression of IMCLs and TGF-β1 levels in IMCLs supernatant, increases that were prevented by preincubation of IMCLs with a microRNA 125b precursor before treatment with Sct. Treatment of: (i) IMCLs with TGF-β1 and r-VEGF-A, respectively, increased the expression of VEGF-A, fibrosis and senescence genes; and (ii) HHSteCs with TGF-β1 and r-VEGF-A, respectively, increased the expression of VEGF-A, fibrosis but decreased senescence genes in HHSteCs (data not shown). The effects of r-VEGF-A on IMCLs and HHSteCs are mediated by interaction with VEGFR-2 that is expressed in both cholangiocytes and hepatic stellate cells.

Discussion.

We demonstrated that the genetic knockout of SR in Mdr2$^{-/-}$ mice has significant inhibitory effects on ductular reaction as well as liver fibrosis through differential changes in the senescence of cholangiocytes and HSCs. The increase in biliary mass and liver fibrosis in Mdr2$^{-/-}$ mice was associated with enhanced senescence of cholangiocytes but decreased HSC senescence, changes that returned to normal values in SR$^{-/-}$/Mdr2$^{-/-}$ mice. The effects of knockout of the Sct/SR axis in Mdr2$^{-/-}$ mice on biliary hyperplasia and liver fibrosis were associated with: (i) decreased levels of Sct and biliary Sct-dependent TGF-β1, which we have shown to activate biliary senescence (by an autocrine Sct-dependent loop, Wu and Alpini, unpublished observations, 2018) and liver fibrosis by a paracrine pathway through decreased senescence of HSCs; and (ii) increased biliary expression of Sct-dependent microRNA 125b and subsequent reduction of microRNA 125b-dependent VEGF-A expression (that increases biliary senescence and fibrosis of IMCLs and decrease HSC senescence but increases fibrogenic activity of HHSteCs). In vitro: (i) Sct-induced TGF-β1 secretion was mediated by microRNA 125b; and (ii) treatment of HHSteCs with the supernatant of cholangiocyte lacking SR (containing lower biliary levels of TGF-β1) displayed decreased fibrosis mRNA expression and increased cellular senescence compared to HHSteCs treated with cholangiocyte supernatant from Mdr2$^{-/-}$ mice.

Changes in ductular reaction in response to cholestatic liver injury are modulated by a number of neuroendocrine/gastrointestinal factors such as gastrin, histamine, angiogenic factors (e.g., VEGF-A), neurotransmitters, melatonin, sex hormones and Sct. Among these neuroendocrine factors, Sct (that exerts its effects by selective interaction with basolateral SR expressed only by cholangiocytes) plays a key role in the autocrine modulation of biliary damage/proliferation/homeostasis in addition to the paracrine regulation of liver inflammation and fibrosis. For example, it has previously been shown that: (i) Sct increases ductular reaction both by autocrine/paracrine pathways through upregulation of cAMP-dependent protein kinase A signaling as well as microRNA 125b-dependent VEGF-A expression (See, Glaser, S et al., *Secretin stimulates biliary cell proliferation by regulating expression of microRNA 125b and microRNA let7a in mice*, Gastroenterology 146(7):1795-1808 e1712 (2014); Alvaro, D et al., Proliferating cholangiocytes: a neuroendocrine compartment in the diseased liver, Gastroenterology 132(1):415-431 (2007); Guerrier, M et al., Prolonged administration of secretin to normal rats increases biliary proliferation and secretin-induced ductal secretory activity, Hepatobiliary Surg Nutr 3(3):118-125 (2014)); and (ii) knockout of the Sct/SR axis reduces biliary hyperplasia as well as liver fibrosis by a paracrine mechanism involving microRNA 125b-dependent decrease of biliary TGF-β1 secretion and reduced VEGF-A expression. Ingenuity Pathway Analysis indicated that the Sct/SR axis is a major upstream regulator of the pathway networks under our experimental conditions, may be suggesting a central role of Sct in regulating liver senescence, angiogenesis and fibrosis. However, our previous studies have limitation because we did not evaluate the potential role of the Sct/SR/microRNA 125b/TGF-β1/VEGF-A axis on the modulation of cellular senescence that may affect both the senescence of cholangiocytes (by an autocrine loop) as well as the senescence of HSCs by a paracrine mechanism mediated by the release of SASP (e.g., in addition to TGF-β1, interleukin-6 (IL-6), IL-8, CCL2, p16/21, SA-β-gal, PAI-1 and substance P), biliary SASP that play a key role in the activation of HSCs and liver fibrosis. Supporting this finding, a recent in vitro study in the human cholangiocyte line, MMNK-1, has identified by microarray analysis differentially regulated genes in response to lysophosphatidylcholine, which included IL-6/8, TGF-β1 and PAI-1 (Shimizu, R et al., *Cholangiocyte senescence caused by lysophosphatidylcholine as a potential implication in carcinogenesis*, J Hepatobiliary Pancreat Sci 22(9):675-682 (2015)). Parallel to this line of research, we have not only demonstrated that TGF-β1, induces the activation of HSCs through decreased cellular senescence by a paracrine mechanism, but also provided novel evidence that TGF-β1 increases biliary senescence by an autocrine loop, thus further increasing the paracrine activation of HSCs by cholangiocytes. Moreover, supporting the key role of TGF-β1 in modulating biliary homeostasis and liver fibrosis, Mdr2$^{-/-}$ mice treated with the SR antagonist (Sec 5-27) displayed reduced biliary mass and HSCs activation, which correlates with decreased TGF-β1/TGF-β1 receptor axis expression.

The observation that attenuated liver fibrosis is associated with decreased senescence of cholangiocytes (associated with reduced Sct-dependent TGF-β1 expression/secretion) is consistent with the finding by Moncsek et al. (Moncsek, A et al., *Targeting senescent cholangiocytes and activated fibroblasts with Bcl-xL inhibitors ameliorates fibrosis in Mdr2(-/-) mice*, Hepatology (Baltimore, Md.) (2017)), who demonstrated that senescent cholangiocytes promote the development of liver fibrosis by secretion of Bcl-XL, which is a key survival factor for several senescent cell types. Inhibition of Bcl-XL in Mdr2$^{-/-}$ mice depletes senescent cholangiocytes and reduces liver fibrosis.

Since it has previously been demonstrated that Sct increases liver fibrosis by: (i) downregulation of microRNA 125b leading to upregulation of VEGF-A; and (ii) stimulation of biliary TGF-β1 secretion, we performed in vitro experiments to demonstrate that: (a) Sct-stimulation of TGF-β1 biliary expression/secretion in IMCLs is mediated by microRNA 125b; and (b) upregulation of VEGF-A in IMCLs (which also increases proliferation and cellular senescence of cholangiocytes by an autocrine loop) is mediated by the Sct-modulation of TGF-β1 expression. (See, Gaudio E et al., *Vascular endothelial growth factor stimulates rat cholangiocyte proliferation via an autocrine mechanism*, Gastroenterology 130(4):1270-1282 (2006)). In support of this concept, microRNA 125b has been shown to play an important role in the regulation of TGF-β1/Smads signaling. For example, microRNA 125b has been shown to be negatively correlated with TGF-β1/Smads signaling pathway in a model of peribiliary fibrosis caused by *Clonorchis sinensis* (Yan, C et al., *Characterization and identification of differentially expressed microRNAs during the process of the peribiliary fibrosis induced by Clonorchis sinensis*, Infect Genet Evol 43:321-328 (2016)). Furthermore, other studies have shown that the downstream targets of miRNA 125b include STAT3, IL-6 as well as TGF-β/Smads signaling. Also, microRNA 125b has been shown to potentiate early neural specification of human embryonic stem cells by a Smad4-dependent mechanism, since reduced microRNA 125b expression leads to upregulation of Smad4. (See, Yin, H et al., Progress on the relationship between miR-125 family and tumorigenesis, Exp Cell Res 2015; 339(2):252-260 (2015); Boissart, C et al., *miR-125 potentiates early neural specification of human embryonic stem cells*. Development 139(7):1247-1257 (2012)).

Taken together, our findings support the hypothesis that the Sct/microRNA 125b/TGF-β1 axis plays a key role in the autocrine modulation of biliary senescence as well as the paracrine regulation of liver fibrosis through decreased HSCs senescence. Since we have shown that Sct increases biliary proliferation by microRNA 125b-dependent increase in VEGF-A, we performed experiments that demonstrated that r-VEGF-A increases (in addition to biliary proliferation)[25] fibrosis and senescence mRNA expression of IMCLs but increases fibrosis and decreases cellular senescence in HHSteCs. Although VEGF has been shown to: (i) decrease the expression of the senescent genes, p16/p21, in human dermal microvascular endothelial cells; and (ii) to increase biliary proliferation and periductular fibrosis (Gaudio, E et al., *Administration of r-VEGF-A prevents hepatic artery ligation-induced bile duct damage in bile duct ligated rats*, Am J Physiol Gastrointest Liver Physiol 291(2):G307-31 (2006)) and fibrogenesis of HSCs (Yoshiji, H et al., *Vascular endothelial growth factor and receptor interaction is a prerequisite for murine hepatic fibrogenesis*, Gut 52(9): 1347-1354 (2003)), no information exists regarding the effect of VEGF-A on biliary and HSC senescence. On this basis, our study provides novel information that VEGF-A is an important SASP that increases biliary senescence (that subsequently activates HSCs by a paracrine pathway) as well as directly HSC fibrogenic activity through decreased HSC senescence. The data introduce the key concept that the Sct/microRNA 125b/TGF-β1/VEGF-A axis is an important mediator of biliary and HSC fibrogenic activity through different changes in biliary (autocrine loop) and HSC (paracrine loop) senescence. Since HSCs secrete VEGF (Zhao, Y et al., *Hepatic stellate cells produce vascular endothelial growth factor via phospho-p44/42 mitogen-activated protein kinase/cyclooxygenase-2 pathway*, Mol Cell Biochem 2012; 359(1-2):217-22 (2012)), we have to also consider in our models the possibility that changes of VEGF-A signaling affects the fibrogenic activity and cellular senescence of HSCs by an autocrine pathway.

Example 5. NAFLD/NASH Studies

Animal Model of NAFLD/NASH.

To obtain preliminary data, male C57BL/6 (Wild-type, WT) mice and SR knockout mice (SR KO) were fed either standard chow (Control Diet, CD) or a high-fat, trans-fat diet plus 0.2% cholesterol (HFD). The diet derives 45% of calories from fat, with 30% of the fat in the form of partially hydrogenated vegetable oil (28% saturated fatty acids, 57% monounsaturated fatty acids, 13% polyunsaturated fatty acids). The mice were given high fructose corn syrup (HFCS) equivalents in the drinking water at 42 g/L (55% fructose, 45% glucose w/w). The mice were fed the HFD for 20 weeks. This diet model was previously established by Anania and colleagues. (See, Mells, J E et al., *Saturated fat and cholesterol are critical to inducing murine metabolic syndrome with robust nonalcoholic steatohepatitis*, J Nutr Biochem 2015; 26:285-92 The model is characterized by murine metabolic syndrome with nonalcoholic steatohepatitis and significant liver fibrosis.[43] These reported findings were replicated in our studies.

SCT/SR Axis is Upregulated in Cholangiocytes Isolated from an Animal Model of NAFLD and in Human Liver Samples with Steatosis and Steatohepatitis.

In the mouse model, the expression of SR was increased in bile ducts in WT+HFD mice compared to control by semi-quantitative analysis of IHC (data not shown). In addition, there was a significant increase in SCT serum levels in WT+HFD mice compared to control (data not shown). In human liver samples (purchased from Sekisui XenoTech, Kansas City, Kans.), there was a similar increase in SR expression in patients with steatosis and steatohepatitis compared to normal liver by semi-quantitative analysis of IHC (data not shown). There was also a significant increase in the gene expression for SCT and SR in total liver samples from patients with steatosis and steatohepatitis by real-time PCR (data not shown). The increase in gene expression is modest since the evaluation was performed in a total liver sample; more analysis is undergoing. The SCT/SR axis is only expressed by cholangiocytes in the liver. We will further evaluate SCT/SR expression in isolated cholangiocytes.

Knockout of SR Prevents HFD-Induced Hepatic Steatosis and Fibrosis.

Figure 9:
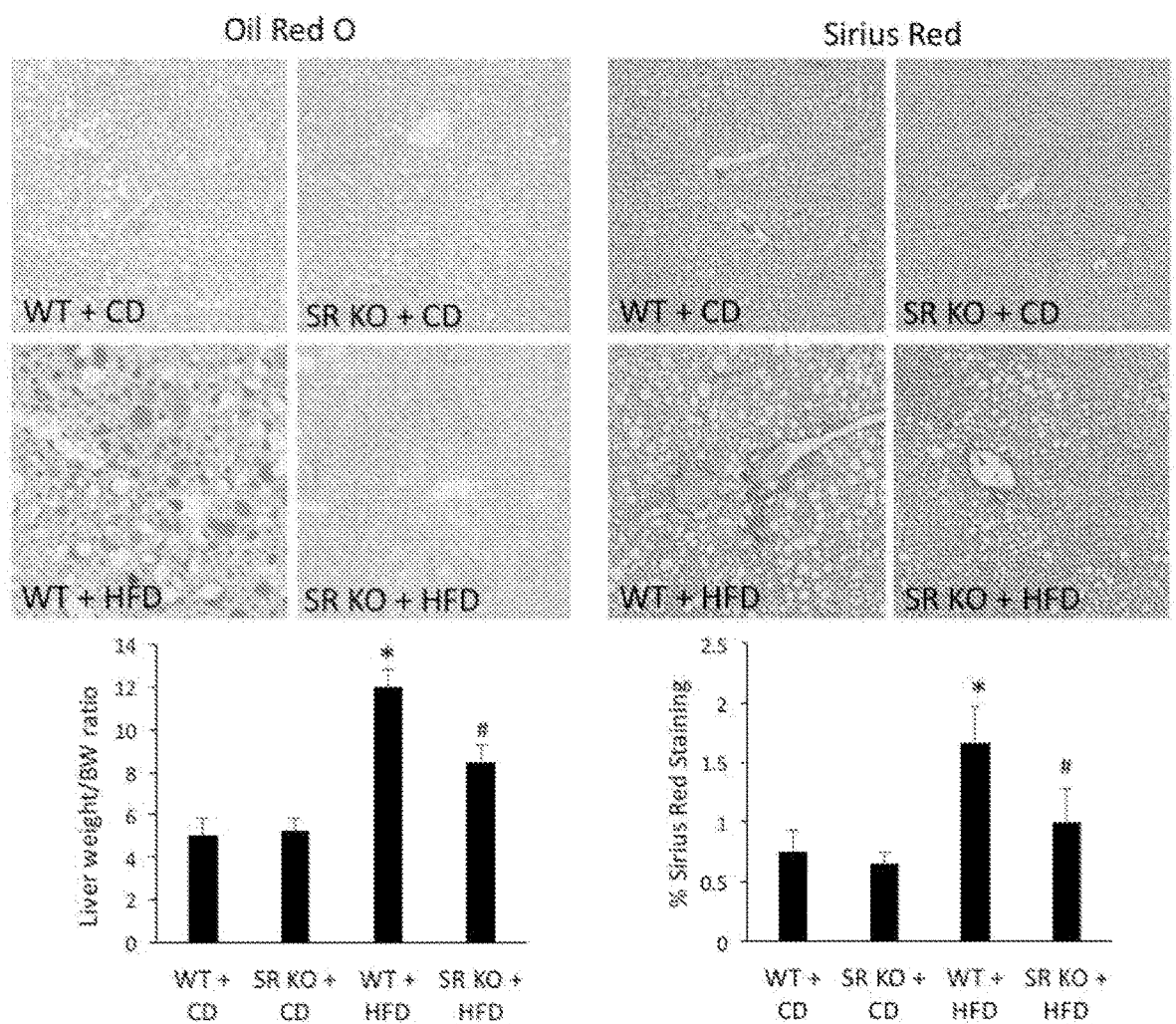
FIG. 9 shows knockdown of SR reduces HFD-induced hepatic steatosis and hepatic fibrosis. [Left top] Hepatic steatosis was evaluated by Oil Red O staining in liver sections. There is a significant reduction in lipid accumulation in hepatocytes in SR KO+HFD compared to WT+HFD. [Left bottom] There was also a significant reduction in liver to body weight ratio in the SR KO+HFD compared to the WT+HFD. Data is presented as mean±SEM (n=6). *$p<0.05$ vs normal. #$p<0.05$ vs WT+HFD. [Right top/bottom] Hepatic fibrosis was evaluated by Sirius Red staining. There is a significant reduction in lipid accumulation in hepatocytes in SR KO+HFD compared to WT+HFD. Data is presented as mean±SEM (n=6). *$p<0.05$ vs WT+CD. #$p<0.05$ vs WT+HFD.

WT and SR KO mice were fed HFD or CD for twenty weeks. SR KO mice exhibited reduced body weight gain and body fat content compared to WT mice when chronically fed HFD (not shown). WT mice fed a high fat diet developed insulin resistance and glucose intolerance consistent with their obese phenotype. Hepatic steatosis was apparent by Oil Red O histochemistry in WT+HFD mice compared to WT+CD. There is a significant reduction in Oil Red O staining in SR KO+HFD compared to WT+HFD (FIG. 9, left panel top). There was also a significant reduction in liver to body weight ratio in the SR KO+HFD compared to the WT+HFD (FIG. 9, left panel bottom). By Sirius Red staining, there was a significant reduction in hepatic fibrosis in the SR KO+HFD compared to the WT+HFD (FIG. 9, right panel). The expression of fibrotic markers (TGF-β1, Col1a1, α-SMA and Fn1) by real-time PCR in total liver, isolated cholangiocytes and HSCs. There was a trend across the cell types (cholangiocytes and HSCs) with a significant increase in the expression of all fibrotic markers in WT+HFD compared to WT+CD (data not shown). There was a significant reduction in the expression of fibrotic markers in both cell types in the SR KO+HFD compared to the WT+HFD treatment group (data not shown). Since cholangiocytes are the only cell type in the liver to express SR, the effects observed in isolated HSCs are due to a paracrine effect presumably due to the activation of cholangiocytes. A similar profile was observed for total liver (not shown). Serum TGF-β1 levels were evaluated by ELISA. There was a significant increase in TGF-β1 levels in WT+HFD compared to WT+CD (216.1±32.7 vs. 83.6±6.87 pg/ml, p<0.01).

TGF-β1 levels were significantly reduced in SR KO+HFD compared to the WT+HFD treatment group (12.1±7.6 vs. 216.1±32.7 pg/ml, p<0.01).

HFD Stimulates Biliary Proliferation in WT Mice that is Blocked by SR Knockout.

Figure 10:
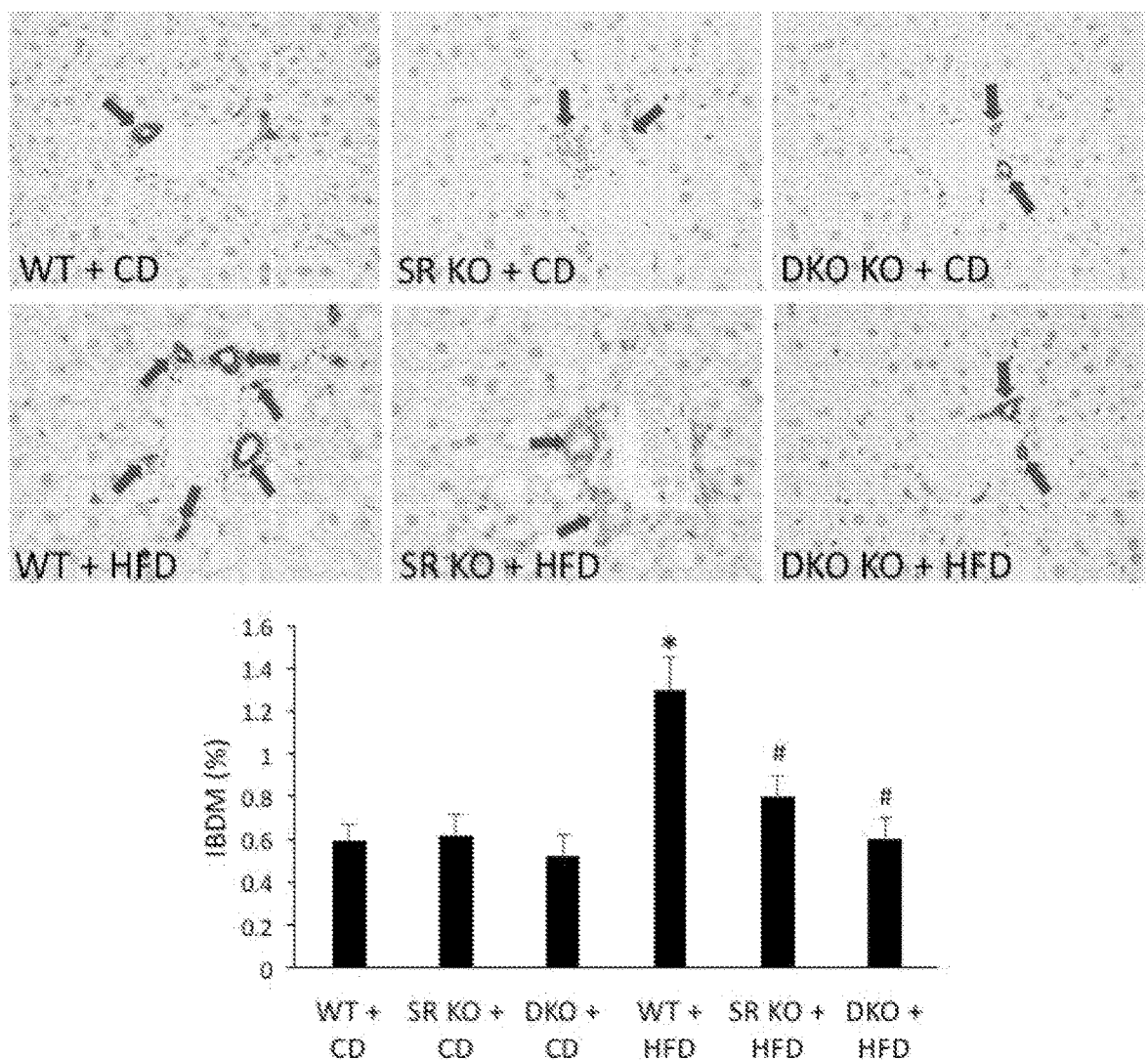
FIG. 10 shows that HFD induces biliary proliferation and small ductular reaction that is prevented by SR and DKO (SCT/SR) knockout. IBDM was evaluated by analysis of CK-19 IHC. There was a significant increase in IBDM in WT+HFD mice compared to WT+CD mice. There was a significant reduction in IBDM in the SR KO+HFD and DKO+HFD compared to the WT+HFD mice. Data is presented as mean±SEM (n=6). *$p<0.05$ vs normal. #$p<0.05$ vs WT+HFD. Bile ducts are indicated by red arrows.

Biliary proliferation was evaluated by analysis of immunohistochemistry for CK-19 (a specific marker of cholangiocytes). There was a significant increase in intrahepatic bile duct mass (IBDM, %) in WT+HFD mice compared to WT+CD mice (FIG. 10). There was a significant reduction in IBDM in the SR KO+HFD and DKO (SCT/SR double knockout)+HFD mice compared to the WT+HFD treatment group (FIG. 10). Small ductular reaction can be observed in the WT+HFD liver (FIG. 10).

HFD Induces Apoptosis in Cholangiocytes from WT Mice that is Blocked by SR Knockout.

We have previously shown that there is a fine balance between biliary proliferation and apoptosis during the pathogenesis of extrahepatic cholestasis in rodent models. In particular, we have observed that during the damage (apoptosis) of large there is increased de novo proliferation of normally mitotically dormant small cholangiocytes. This proliferation is associated with increased expression of the SCT/SR axis in small cholangiocytes. (See, LeSage, G D et al., Acute carbon tetrachloride feeding induces damage of large but not small cholangiocytes from BDL rat liver, Am J Physiol 276:G1289-301 (1999); Mancinelli, R et al., *After damage of large bile ducts by gamma-aminobutyric acid, small ducts replenish the biliary tree by amplification of calcium-dependent signaling and de novo acquisition of large cholangiocyte phenotypes*, Am J Pathol 2010; 176: 1790-800 (2010)).

We infer that the activation of biliary proliferation and small ductular reaction observed in the WT+HFD is due to biliary injury such as lipoapoptosis. A previous report has demonstrated that FFAs trigger cholangiocyte lipoapoptosis. Apoptosis was evaluated in liver sections by TUNEL staining and by real-time PCR for Bax (Bcl-2-like protein 4, a pro-apoptotic member of the Bcl-2 protein family) expression in isolated cholangiocytes. There was a significant increase in TUNEL staining in the bile ducts of the liver sections as well as an increase in Bax expression in cholangiocytes isolated from WT+HFD compared to WT+CD mice (data not shown). The HFD-induced increase in TUNEL positive cholangiocytes and Bax expression was ablated in SR KO+HFD mice (data not shown).

miR-125b and Let-7a Expression Levels are Downregulated with Concomitant Upregulation of VEGF-A and NGF Expression in WT Mice Fed HFD.

It was shown that following liver injury, secretin produced by cholangiocytes and S cells reduces miR-125b and let-7a levels in cholangiocytes, resulting in upregulation of VEGF and NGF, respectively. (See, Glaser, S et al., *Secretin stimulates biliary cell proliferation by regulating expression of microRNA 125b and microRNA let7a in mice*, Gastroenterology 146:1795-808 e12 (2014). We have also shown that let-7a plays a key role in hepatic fibrosis as inhibition of let-7a accelerated hepatic fibrosis during cholestasis. (See, Wu, N et al., *The secretin/secretin receptor axis modulates liver fibrosis through changes in transforming growth factor-beta1 biliary secretion in mice*, Hepatology 2016; 64:865-79 (2016)). Based upon our previous studies demonstrating that the SCT/SR axis regulates biliary miR-125b and let-7a expression and that HFD upregulates the SCT/SR axis, we evaluate the effects of HFD on cholangiocyte expression of miR-125b and let-7a. We performed miRNA profiling in WT+CD and WT+HFD (UCLA Technology Center for Genomics & Bioinformatics). miRNA profiling revealed that there was a significant downregulation of miR-125b (~50% reduction) and let-7a (~60% reduction) expression levels. Since we have previous shown that miR-125b and let-7a target VEGF-A and let-7a in cholangiocytes (respectively), we evaluated VEGF-A and NGF expression levels by real-time PCR and found that there was a significant increase in both VEGF-A (2-fold increase) and NGF (1.9-fold increase) expression levels in WT+HFD group compared to WT+CD group.

In Vitro Stimulation of Mouse Cholangiocytes (MCC) with Saturated FFAs Upregulates the Expression of the SCT/SR Axis and Downregulates the Expression of miR-125b and Let-7a.

To determine if FFAs have a direct effect on cholangiocyte expression of the SCT/SR axis and miR-125b and let-7a, we used a mouse cholangiocyte cell line (MCC) and stimulated this cell line with saturated FFAs, palmitate and stearate, and the monounsaturated FFA, oleate for 24 hours. SCT and SR expression were evaluated by real-time PCR and SCT secretion in to the media by ELISA. miRNA expression levels were evaluated by TaqMan MicroRNA Assay (Thermo Fisher Scientific). There was a significant increase in SCT and SR gene expression in MCC stimulated with saturated FFAs (palmitate and stearate) but not unsaturated FFAs (oleate) (data not shown). There was also increase SCT secretion in to the media of MCC stimulated with palmitate and stearate but not oleate (data not shown). miR-125b and let-7a expression levels were also decreased in MCC stimulated with palmitate and stearate for 24 hours (data not shown). These findings indicate a direct link between saturated FFAs and the SCT/SR axis in cholangiocytes. Several reports have shown that the saturated FFAs trigger TLR4-dependent signaling mechanisms in several cell types. TLR4 is expressed by cholangiocytes and mediates cholangiocyte responses to *Cryptosporidium parvum* infection and gram-negative bacteria-derived LPS. (See, O'Hara, S P et al., *Cholangiocyte N-Ras protein mediates lipopolysaccharide-induced interleukin 6 secretion and proliferation*, J Biol Chem 2011; 286:30352-60 (2011); O'Hara, S P et al., *TLR4 promotes Cryptosporidium parvum clearance in a mouse model of biliary cryptosporidiosis*, J Parasitol 2011; 97:813-21 (2011)).

Expression of Fibrotic Marker Genes Induced by Saturated FFAs is Dependent Upon SR Expression in MCC Treated with Palmitate and Stearate.

MCC were stimulated with saturated FFAs, palmitate and stearate, and the monounsaturated FFA, oleate for 24 hours. SR expression was knocked down by transfection with shRNA for SR. Fibrotic marker gene expression and the pro-apoptotic Bax expression were evaluated by real-time PCR. There was a significant increase in the expression levels of TGF-β1, Col1a1, α-SMA and Fn1 in MCC treated with palmitate and stearate but not oleate compared to control (data not shown). The saturated FFA-induced increases in fibrotic marker gene expression that was significantly blocked by the knockdown of SR suggesting a role of the SCT/SR axis in the direct effects of FFAs on cholangiocytes (data not shown). Saturated FFAs also induced a significant increase in Bax expression levels in MCC, which was partially blocked by SR knockdown (data not shown).

HFD Alters the Expression of Genes Involved in Lipid Catabolism in Cholangiocytes.

We evaluated the gene expression of carnitine palmitoyl-transferase IA (Cpt1a), long-chain-fatty-acid CoA ligase 1

(Acsl1) and peroxisome proliferator-activated receptor (PPAR-□) in cholangiocytes isolated from CD and HFD treated mice.

There was a significant decrease in CptIa, Acsl1 and PPAR-α expression in WT+HFD compared to WT+CD cholangiocytes (data not shown). There was a significant increase CptIa, Acsl1 and PPAR-α expression in SR KO+HFD compared to all other treatment groups (data not shown). This implies that the expression levels of CptIa, Acsl1 and PPAR-α are regulated at the miRNA level in cholangiocytes; miR-200b and miR-181b are predicted to target CptIa; miR-181b is predicted to target Acsl1; and miR-506 is a predicted target for PPAR-α. In preliminary miRNA profiling, there was a significant increase in miR-200b, miR-181b and miR-506 in WT+HFD compared to WT+CD (not shown).

While the present invention does not depend on any particular mechanism, based upon our preliminary data, we have inferred an overall working hypothesis for the regulation the proliferative and activated profibrogenic biliary phenotype by the SCT/SR axis signaling that contributes to the progression of hepatic steatosis and fibrosis during the pathogenesis of NAFLD. We infer that the expression of the SCT/SR axis is upregulated during biliary damage (i.e., cholangiocyte lipoapoptosis) triggered by chronic exposure to fatty acids during HFD. SCT in turn stimulates biliary proliferation in an autocrine/paracrine fashion during the progression of NAFLD. Activation of SR triggers the downregulation of let-7a and miR-125b expression levels, which are miRNA that we have shown to target the expression of NGF and VEGF-A in cholangiocytes during animals models of biliary damage. (See, Glaser, S et al., *Secretin stimulates biliary cell proliferation by regulating expression of microRNA 125b and microRNA let7a in mice*, Gastroenterology 2014; 146:1795-808 e12 (2014); Wu, N et al., *The secretin/secretin receptor axis modulates liver fibrosis through changes in transforming growth factor-beta1 biliary secretion in mice*, Hepatology 2016; 64:865-79 (2016)). The resultant increase in NGF and VEGF-A expression/secretion by cholangiocytes plays an important role in stimulating biliary proliferation and biliary expression of fibrotic factors in an autocrine mechanism. SCT also stimulates the expression/secretion of TGF-β1, which acts both in an autocrine pathway (activating biliary proliferation and fibrogenic activity) as well as a paracrine fashion in combination with VEGF-A and NGF to activate HSCs contributing to further hepatic fibrosis during NAFLD/NASH. Our preliminary data clearly indicate that free fatty acids (FFA) have a direct effect on cholangiocytes through activation of biliary damage and the stimulation of SCT secretion and upregulation of SR expression.

We infer that the FFAs directly stimulate SCT secretion and/or SCT/SR axis expression by cholangiocytes via a TLR4-dependent mechanism (data not shown). Previous studies have shown the saturated FFAs can signal via TLR4 activating signaling pathways that promote production and release of inflammatory cytokines (IL-6 and TFN-α). In cholangiocytes activation of TLR4 has been shown to increase cholangiocyte proliferation in an N-RAS/MEK/ERK1/2-dependent mechanism that was associated with increased IL-6 secretion. Other studies have shown that TLR4 signals via a MyD88/NF□B signaling mechanism. We have previously shown that the SCT/SR axis is upregulated during cholangiocyte proliferation, which we have shown is predominantly regulated via ERK1/2-dependent signaling. NFκB signaling has been shown to play a role in ductular reaction and cholangiocyte proliferation. (See, Kim, K H et al., CCN1 induces hepatic ductular reaction through integrin alphavbeta(5)-mediated activation of NF-kappaB, J Clin Invest 2015; 125:1886-900 (2015); Onori, P et al., *Caffeic acid phenethyl ester decreases cholangiocarcinoma growth by inhibition of NF-kappaB and induction of apoptosis*, Int J Cancer 2009; 125:565-76 (2009)). We also performed miRNA profiling in cholangiocytes isolated from WT mice fed HFD compared to WT fed control diet. The profiling revealed alterations in the expression levels of multiple miRNAs including the upregulation of miR-181b, miR-200b, and miR-506, which as mentioned earlier are miRNAs that are predicted to target the expression of genes that play a key role in lipid catabolism, CptIa, Acsl1 and PPAR-α. Our preliminary findings indicate that there are alterations in the expression levels of CptIa, Acsl1 and PPAR-α with an expected decrease in WT animals fed HFD while a significant increase in expression is observed in SR KO mice fed HFD. miR-200b and miR-181b are predicted to target CptIa; miR-181b is predicted to target Acsl1; and miR-506 is a predicted target for PPAR-α, which may result in altered lipid catabolism in cholangiocytes.

Those skilled in the art will recognize, or be able to ascertain using no more than routine experimentation, numerous equivalents to the specific procedures described herein. Such equivalents are considered to be within the scope of the present invention and are covered by the claims (following a list of abbreviations hereafter). The contents of all references, patents, and patent applications cited throughout this application are hereby incorporated by reference. The appropriate components, processes, and methods of those patents, applications and other documents can be selected for the present invention and embodiments thereof.

ABBREVIATIONS USED HEREIN INCLUDE THE FOLLOWING

ALP=alkaline phosphatase;
AE2=chloride bicarbonate anion exchanger 2;
α-SMA=α-smooth muscle actin;
BDL=bile duct ligated;
BSA=bovine serum albumin;
CCL2=C—C motif chemokine ligand 2;
CFTR=cystic fibrosis transmembrane conductance regulator;
CK-19=cytokeratin-19;
Col1a1=collagen, type I, alpha 1;
dnTGFβRII=dominant negative transforming growth factor-beta receptor II;
Fn-1=fibronectin-1;
γGT=gamma-glutamyltranspeptidase;
GAPDH=glyceraldehyde-3-phosphate dehydrogenase;
H&E=hematoxylin & eosin;
hr=hour
HSC=hepatic stellate cell;
hHSC=human hepatic stellate cell;
HHSteCs=human hepatic stellate cell lines;
IBDM=intrahepatic bile duct mass;
IMCLs=immortalized murine biliary cell lines;
INR="International normalized ratio" (a blood-clotting test);
LCM=laser capture microdissection;
p16=cyclin-dependent kinase inhibitor 2A;
p18=cyclin-dependent kinase inhibitor 4C;
p21=cyclin-dependent kinase inhibitor 1;
PAI-1=plasminogen activator inhibitor-1;
PBC=primary biliary cholangitis;
PCNA=proliferating cell nuclear antigen;

PSC=primary sclerosing cholangitis;
SA-β-gal=senescence-associated-betagalactosidase;
α-SMA=alpha-smooth muscle actin;
SR=secretin receptor;
SYP-9=synaptophysin-9;
Sct=secretin;
SMAD2/3=small mothers of decapentaplegic 2 and 3;
SR=secretin receptor;
TGF-β1=transforming growth factor-β1;
TGF-β1R=transforming growth factor-β1 receptor;
TUNEL=terminal deoxynucleotidyl transferase dUTP nick-end labeling;
wk=week
WT=wild-type.

What is claimed is:

1. A method of treating an early stage cholestatic liver disease in a mammalian subject in need thereof, comprising administering an effective amount of Sec 5-27 to said subject, wherein the cholestatic liver disease is selected from the group consisting of Primary Biliary Cholangitis (PBC), Biliary Atresia, non-alcoholic steatohepatitis (NASH), non-alcoholic fatty liver disease (NAFLD), and alcohol induced liver injury.

2. The method of claim 1, wherein the mammalian subject is a human.

3. The method of claim 1, wherein the cholestatic liver disease is PBC.

4. The method of claim 3, wherein PBC is Stage I.

5. The method of claim 3, wherein PBC is Stage II.

6. The method of claim 1, wherein treating comprises inhibiting bile duct cell proliferation.

7. The method of claim 1, wherein Sec 5-27 is administered as a single active agent.

8. A method of treating Late Stage Primary Biliary Cholangitis (PBC) in a mammalian subject in need thereof, comprising administering an effective amount of secretin to said subject.

9. The method of claim 8, wherein the mammalian subject is a human.

10. The method of claim 8, wherein Late Stage PBC is Stage III.

11. The method of claim 8, wherein Late Stage PBC is Stage IV.

12. The method of claim 8, wherein the mammalian subject has a bilirubin level of >1 mg/dl.

13. The method of claim 8, wherein treating comprises ameliorating PBC-induced biliary damage.

14. The method of claim 8, wherein treating comprises ameliorating liver fibrosis.

15. The method of claim 8, wherein secretin is administered as a single active agent.

* * * * *